US009631050B2

(12) United States Patent
Coady et al.

(10) Patent No.: US 9,631,050 B2
(45) Date of Patent: Apr. 25, 2017

(54) ANTIMICROBIAL CATIONIC POLYCARBONATES

(71) Applicants: International Business Machines Corporation, Armonk, NY (US); Agency For Science, Technology and Research, Singapore (SG)

(72) Inventors: Daniel J. Coady, Bluffton, GA (US); Richard A. Dipietro, Campbell, CA (US); Amanda C. Engler, Woodbury, MN (US); James L. Hedrick, Pleasanton, CA (US); Victor W. L. Ng, Singapore (SG); Zhan-Yuin Ong, London (GB); Jeremy P. K. Tan, Singapore (SG); Yi Yan Yang, Singapore (SG)

(73) Assignees: International Business Machines Corporation, Armonk, NY (US); Agency For Science, Technology And Research, Singapore (SG)

( * ) Notice: Subject to any disclaimer, the term of this patent is extended or adjusted under 35 U.S.C. 154(b) by 0 days.

(21) Appl. No.: 15/154,948

(22) Filed: May 14, 2016

(65) Prior Publication Data
US 2016/0257782 A1 Sep. 8, 2016

Related U.S. Application Data

(63) Continuation of application No. 13/859,048, filed on Apr. 9, 2013, now Pat. No. 9,357,772.

(51) Int. Cl.
| | | |
|---|---|---|
| A61K 31/00 | (2006.01) |
| C08G 63/64 | (2006.01) |
| A01N 33/12 | (2006.01) |
| A01N 43/50 | (2006.01) |
| A01N 57/34 | (2006.01) |
| A61K 9/00 | (2006.01) |
| A61K 31/765 | (2006.01) |
| A61K 47/48 | (2006.01) |

(52) U.S. Cl.
CPC ............ *C08G 63/64* (2013.01); *A01N 33/12* (2013.01); *A01N 43/50* (2013.01); *A01N 57/34* (2013.01); *A61K 9/0019* (2013.01); *A61K 31/765* (2013.01); *A61K 47/481* (2013.01); *A61K 47/48107* (2013.01); *A61K 47/48123* (2013.01); *A61K 2800/54* (2013.01); *A61K 2800/542* (2013.01); *A61K 2800/5426* (2013.01)

(58) Field of Classification Search
None
See application file for complete search history.

(56) References Cited

U.S. PATENT DOCUMENTS

| | | |
|---|---|---|
| 2004/0115160 A1 | 6/2004 | Salamone et al. |
| 2004/0156800 A1 | 8/2004 | Brun et al. |
| 2009/0012028 A1 | 1/2009 | Chan et al. |
| 2009/0069435 A1 | 3/2009 | Whiteford |
| 2009/0138041 A1 | 5/2009 | Stopek et al. |
| 2010/0282409 A1 | 11/2010 | Hobbs et al. |
| 2011/0054064 A1 | 3/2011 | Fukushima et al. |
| 2011/0150977 A1 | 6/2011 | Hedrick et al. |
| 2011/0223202 A1 | 9/2011 | Yang et al. |
| 2012/0071525 A1 | 3/2012 | Schwarz et al. |
| 2012/0195849 A1 | 8/2012 | Tew et al. |
| 2012/0232018 A1 | 9/2012 | Hedrick et al. |
| 2012/0245218 A1 | 9/2012 | Fukushima et al. |
| 2012/0251607 A1 | 10/2012 | Coady et al. |
| 2012/0251608 A1 | 10/2012 | Coady et al. |
| 2013/0011457 A1 | 1/2013 | Hedrick et al. |
| 2014/0072607 A1 | 3/2014 | Hedrick et al. |
| 2014/0301967 A1 | 10/2014 | Chin et al. |
| 2014/0301968 A1 | 10/2014 | Coady et al. |

FOREIGN PATENT DOCUMENTS

| | | |
|---|---|---|
| CN | 102762634 A | 10/2012 |
| WO | 2008110740 A1 | 9/2008 |

OTHER PUBLICATIONS

Allison, et al., "Hemocompatibility of Hydrophilic Antimicrobial Copolymers of Alkylated 4-Vinylpyridine", Biomacromolecules, 2007, 8 (10), pp. 2995-2999; Publication Date (Web): Sep. 18, 2007.
Brogden, "Antimicrobial Peptides: Pore Formers or Metabolic Inhibitors in Bacteria?", Nature Review, 3, 2005, 238-250; Published online Feb. 10, 2005.
Cadwallader, et al., "Hemolysis of Erythrocytes by Antibacterial Preservatives II Quaternary Ammonium Salts", Journal of Pharmaceutical Sciences, vol. 54, No. 7, Jul. 1965, pp. 1010-1012.
Engler, et al., "Effects of Side Group Functionality and Molecular Weight on the Activity of Synthetic Antimicrobial Polypeptides," Biomacromolecules 2011, 12, 1666-1674; Published: Mar. 28, 2011.
Engler, et al., "Emerging trends in macromolecular antimicrobials to fight multi-drug-resistant infections," Nano Today (2012) 7, 201-222; Available online May 16, 2012.
Eren, et al., "Antibacterial and Hemolytic Activities of Quaternary Pyridinium Functionalized Polynorbornenes, " Macromol. Chem. Phys. 2008, 209, 516-524.
Gabriel, et al., "Infectious disease: Connecting innate immunity to biocidal polymers", Materials Science and Engineering R 57 (2007), pp. 28-64.

(Continued)

*Primary Examiner* — James Rogers
(74) *Attorney, Agent, or Firm* — Michael R. Roberts

(57) ABSTRACT

Antimicrobial cationic polymers having one or two cationic polycarbonate chains were prepared by organocatalyzed ring opening polymerization. One antimicrobial cationic polymer has a polymer chain consisting essentially of cationic carbonate repeat units linked to one or two end groups. The end groups can comprise a covalently bound form of biologically active compound such as cholesterol. Other antimicrobial cationic polymers have a random copolycarbonate chain comprising a minor mole fraction of hydrophobic repeat units bearing a covalently bound form of a vitamin E and/or vitamin D2. The cationic polymers exhibit high activity and selectivity against Gram-negative and Gram-positive microbes and fungi.

23 Claims, 14 Drawing Sheets

(56) References Cited

OTHER PUBLICATIONS

Lee, et al., "Injectable Hydrogels from Triblock Copolymers of Vitamin E-Functionalized Polycarbonate and Poly(ethylene glycol) for Subcutaneous Delivery of Antibodies for Cancer Therapy," Adv. Funct. Mater. 2014, 24, pp. 1538-1550.

Nederberg, et al., "Biodegradable nanostructures with selective lysis of microbial membranes" Nature Chemistry, vol. 3, 2011, 409-414; Published Online: Apr. 3, 2011.

PCT International Search Report, dated Aug. 25, 2014, PCT/US2014/032313.

PCT Written Opinion, dated Aug. 25, 2014, PCT/US2014/032313.

PCT—International Search report, dated Aug. 21, 2014, PCT/US214/31982, filed Mar. 27, 2014.

PCT—Written Opinion, dated Aug. 21, 2014, PCT/US214/31982, filed Mar. 27, 2014.

Pratt, et al., "Exploration, Optimization, and Application of Supramolecular Thiourea-Amine Catalysts for the Synthesis of Lactide (Co)polymers," Macromolecules 2006, 39, 7863-7871; Published on Web Oct. 18, 2006.

Pratt, et al., "Tagging alcohols with cyclic carbonate: a versatile equivalent of (meth)acrylate for ring opening polymerization," Chem.Commun., 2008, 114-116; publishe Oct. 25, 2007.

Qiao, et al., "Highly dynamic biodegradable micelles capable of lysing Gram-positive and Gram-negative bacterial membrane", Biomaterials 33 (2012) 1146 -1153; Available online Nov. 5, 2011.

Sambhy, et al., "Antibacterial and Hemolytic Activities of Pyridinium Polymers as a Function of the Spatial Relationship between the Positive Charge and the Pendant Alkyl Tail," Angew. Chem. Int. Ed. 2008, 47, 1250-1254.

Stratton, et al., "Biocompatibility of Quaternary Poly(Vinyl Pyridine)-Based Bactericidal Copolymers As Determined by In Vitro Assays of Human Epithelium", Polymer Preprints 2009, 50(2), pp. 176-177.

Thorsteinsson, et al., "Soft Antimicrobial Agents: Synthesis and Activity of Labile Environmentally Friendly Long Chain Quaternary Ammonium Compounds,", J. Med. Chem. 2003, 46, 4173-4181; Published on Web Aug. 5, 2003.

Tiller, et al., "Designing surfaces that kill bacteria on contact", PNAS, May 22, 2001, vol. 98, No. 11, pp. 5981-5985.

USPTO, final office action, application 13859037, mailed Mar. 18, 2015.

USPTO, non-final office action, application 13859037, mailed Oct. 23, 2014.

Wan et al., "Synthesis and Characterization of Biodegradable Cholesteryl End-Capped Polycarbonates" Biomacromolecules 2005, 6, 524-529; Published on Web Dec. 15, 2004.

ANTIMICROBIAL CATIONIC POLYCARBONATES

This invention was made under a joint research agreement between International Business Machines Corporation and the Agency For Science, Technology and Research.

BACKGROUND

The present invention relates to antimicrobial cationic polycarbonate polymers, and more specifically, to cationic polycarbonate homopolymers and random copolymers having 85 mol % to 100 mol % cationic carbonate repeat units.

The increasing presence of antibiotic resistant bacteria has caused an urgent need to develop new antibiotics. Antimicrobial peptides have high activity, biocompatibility and excellent selectivity. However, despite over 1000 antimicrobial peptides having been identified, only four peptides have successfully entered phase III clinical trials for wound healing. The primary reasons for their extremely limited use arises from challenging syntheses, high construction costs and in vivo instability due to protease degradation. Synthetic cationic polymers offer inherently lower cost alternatives that lack enzyme recognition. Synthetic polymers bearing cationic charges can analogously associate with bacterial membranes through comparable electrostatic interactions. Furthermore, synthetic cationic polymers can be readily synthesized to have hydrophobic regions capable of being integrated within bacterial membranes. However, increasing hydrophobicity in an effort to gain activity has often proved problematic because of selectivity loss as evidenced by dramatic increases in hemolytic activity and/or cytotoxicity.

Thus, synthetic antimicrobial polymers are sought having enhanced antimicrobial activity without sacrificing microbial selectivity.

SUMMARY

Accordingly, an antimicrobial cationic polymer is disclosed having a structure according to formula (12):

wherein

C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each polymer chain $P^b$ consists essentially of cationic carbonate repeat units, wherein i) the cationic polymer comprises a total of 5 to about 45 cationic carbonate repeat units, ii) each of the cationic carbonate repeat units comprises a backbone portion of the polymer chain and a cationic side chain linked to the backbone portion, and iii) the cationic side chain comprises a positive-charged heteroatom Q' of a quaternary ammonium group and/or quaternary phosphonium group, about 25% to 100% of all the cationic carbonate repeat units of the cationic polymer, designated first cationic carbonate repeat units, have a cationic side chain comprising 10 to about 25 carbons, and 0% to about 75% of the cationic carbonate repeat units of the cationic polymer, designated second cationic carbonate repeat units, have a cationic side chain comprising 6 to 9 carbons.

Also disclosed is an antimicrobial cationic polymer of formula (14):

wherein

C" is a divalent linking group joining polymer chains $P^b$, wherein C" comprises i) a first heteroatom linked to a first polymer chain $P^b$, wherein the first heteroatom is selected from the group consisting of nitrogen, oxygen, and sulfur, ii) a second heteroatom linked to a second polymer chain $P^b$, wherein the second heteroatom is selected from the group consisting of nitrogen, oxygen, and sulfur, and iii) a covalently bound form of a compound selected from the group consisting of steroids, non-steroid hormones, vitamins, and drugs, each $Z^c$ is an independent monovalent end group selected from the group consisting of hydrogen and $C_1$-$C_{15}$ moieties, each polymer chain $P^b$ consists essentially of cationic carbonate repeat units, wherein i) the cationic polymer comprises a total of 5 to about 45 cationic carbonate repeat units, ii) each of the cationic carbonate repeat units comprises a backbone portion of the polymer chain and a $C_6$-$C_{25}$ cationic side chain linked to the backbone portion, and iii) the cationic side chain comprises a positive-charged heteroatom Q' of a quaternary ammonium group and/or quaternary phosphonium group, about 25% to 100% of the cationic carbonate repeat units of the cationic polymer, designated first cationic carbonate repeat units, have a cationic side chain group comprising 10 to about 25 carbons, and 0% to about 75% of the cationic carbonate repeat units of the cationic polymer, designated second cationic carbonate repeat units, have a cationic side chain group comprising 6 to 9 carbons.

Further disclosed is an antimicrobial cationic random copolymer of formula (16):

wherein

C' is a $C_2$-$C_{15}$ divalent linking group joining polymer chains $P^c$, wherein C' comprises i) a first heteroatom linked to a first polymer chain $P^c$, wherein the first heteroatom is selected from the group consisting of nitrogen, oxygen, and sulfur, and ii) a second heteroatom linked to a second polymer chain $P^c$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each $P^c$ is a polymer chain consisting essentially of I) about 85 mol % to 99.9 mol % of cationic carbonate repeat units, and II) 0.1 mol % to about 15 mol % of a carbonate repeat unit comprising a covalently bound form of a steroid and/or a vitamin compound, wherein i) the cationic polymer has a total number of repeat units of about 5 to about 45, ii) each of the cationic carbonate repeat units comprises a polymer backbone portion and a $C_6$-$C_{25}$ cationic side chain portion linked to the polymer backbone portion, and iii) each cationic side chain portion comprises a positive-charged heteroatom Q' of a quaternary ammonium group and/or quaternary phosphonium group, about 25% to 100% of the cationic carbonate repeat units of the cationic polymer, designated first cationic carbonate repeat units, have a cationic side chain group comprising 10 to about 25 carbons, and 0% to about 75% of the cationic carbonate repeat units of the cationic polymer, designated second cationic carbonate repeat units, have a cationic side chain group comprising 6 to 9 carbons.

Another antimicrobial cationic random copolymer having a structure in accordance with formula (18):

$$Y^c\text{—}P^b\text{—}C'\text{—}P^b\text{—}Y^d \qquad (18),$$

wherein

C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, $Y^c$ is an independent monovalent first end group selected from the group consisting of hydrogen, groups comprising a covalently bound form of a steroid, and groups comprising a covalently bound form of a vitamin, $Y^d$ is an independent monovalent second end group selected from the group consisting of hydrogen, groups comprising a covalently bound form of a steroid, and groups comprising a covalently bound form of a vitamin, each polymer chain $P^b$ consists essentially of cationic carbonate repeat units, wherein i) the cationic polymer comprises a total of 5 to about 45 cationic carbonate repeat units, ii) each of the cationic carbonate repeat units comprises a backbone portion of the polymer chain and a cationic side chain linked to the backbone portion, and iii) the cationic side chain comprises a positive-charged heteroatom Q' of a quaternary ammonium group and/or quaternary phosphonium group, about 25% to 100% of all the cationic carbonate repeat units of the cationic polymer, designated first cationic carbonate repeat units, have a cationic side chain comprising 10 to about 25 carbons, and 0% to about 75% of the cationic carbonate repeat units of the cationic polymer, designated second cationic carbonate repeat units, have a cationic side chain comprising 6 to 9 carbons.

Also disclosed is a method comprising, forming a polycarbonate by an organocatalyzed ring opening polymerization (ROP) of a cyclic carbonate monomer, wherein the ROP is initiated by a di-nucleophilic compound selected from the group consisting of steroids, vitamins, compounds comprising a covalently bound form of the foregoing steroids and vitamins, and combinations thereof;

optionally endcapping the polycarbonate; and treating the polycarbonate with a quaternizing agent, thereby forming an antimicrobial cationic polymer;

and wherein the cyclic carbonate monomer has the structure formula (15):

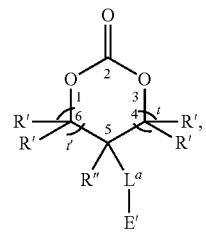

wherein the ring atoms are shown numbered 1 to 6, t is a positive integer having a value of 0 to 2, t' is a positive integer having a value of 0 to 2, t and t' cannot both be zero, $L^a$ is a divalent linking group comprising 3 or more carbons, E' is a group capable of reacting to form a cationic moiety $(Q'(R^a)_{u'})$ linked to $L^a$, wherein Q' is a tetravalent positive-charged nitrogen or phosphorus, u' has a value of 1 to 3, and each $R^a$ is an independent radical having a valency of 1 to 3, wherein each $R^a$ comprises 1 or more carbons, each R' is an independent monovalent radical selected from the group consisting of hydrogen and methyl, and R" is a monovalent radical selected from the group consisting of hydrogen, methyl and ethyl.

The above-described and other features and advantages of the present invention will be appreciated and understood by those skilled in the art from the following detailed description, drawings, and appended claims.

DETAILED DESCRIPTION

Figure 1A:
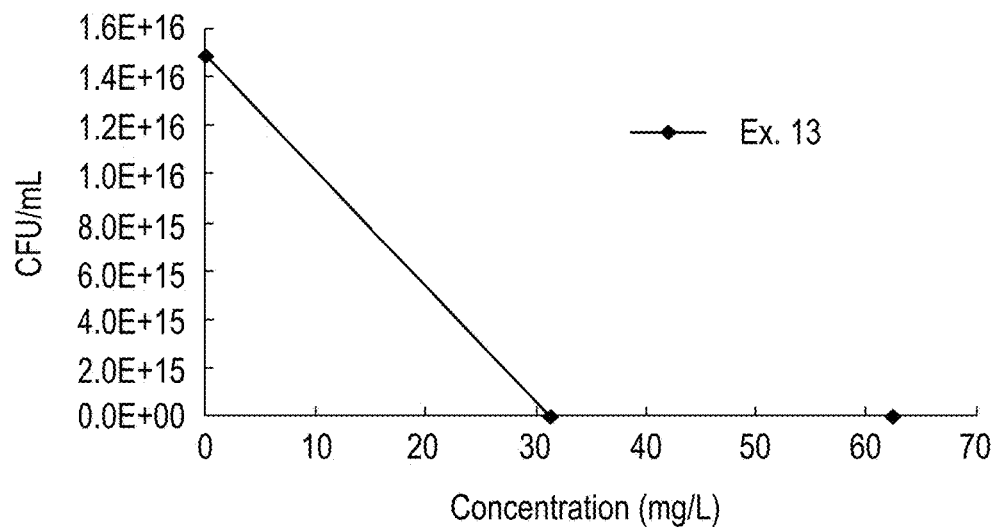
FIGS. 1A and 1B are graphs showing the number of viable *Staphylococcus aureus* (*S. aureus*) colony-forming units (CFU) after 18 hours incubation with three concentrations of cationic polymers Example 13 and Example 23, respectively. The concentrations were 0, MIC, and 2×MIC, where MIC is the minimum inhibitory concentration of about 31 mg/L.

The invention is based on antimicrobial cationic polymers in which 85% to 100% of the repeat units are cationic carbonate repeat units. The cationic polymers generally have low mass and are highly active and selective against Gram-positive microbes, Gram-negative microbes, and fungi. The activity and/or selectivity is shown to be considerably influenced by the spacing of the positive charged heteroatom from the backbone, as well as the size and type of substituent linked to the charged heteroatom. The activity and/or selectivity can also be favorably influenced using mixtures of cationic repeat units in which the positive-charged heteroatom is spaced at different lengths from the backbone. The size and type of polymer end groups can also have influence on the activity and/or selectivity. The cationic polymers are preferably formed using a process that includes an organocatalyzed ring opening polymerization (ROP) of one or more cyclic carbonate monomers capable of forming cationic carbonate repeat units after the polymerization. The polymers can be formed using a mono-nucleophilic initiator and/or a di-nucleophilic initiator.

Also disclosed are antimicrobial cationic copolymers that include a minor mole fraction of carbonate repeat units comprising a covalently bound form of a vitamin. Preferably, these repeat units are non-charged.

The cationic polymers can be biodegradable. The term "biodegradable" is defined by the American Society for Testing and Materials as degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

The cationic polymers can be biocompatible. A "biocompatible" material is defined herein as a material capable of performing with an appropriate host response in a specific application.

Herein, a vitamin is defined as any of a group of organic compounds that are essential in small quantities for normal metabolism of a living body, and generally cannot be synthesized in the body. Exemplary vitamins include vitamin A (retinol), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12 (cobalamines), beta-carotene, vitamin C (ascorbic acid), vitamin D compounds (which include vitamin D1 (calciferol), vitamin D2 (ergocalciferol), and/or vitamin D3 (cholecalciferol)), vitamin E compounds (which include alpha-tocopherol, beta-tocopherol, gamma-tocopherol, delta-tocopherol, alpha-tocotrienol, beta-tocotrienol, gamma-tocotrienol and/or delta-tocotrienol), and vitamin K1 (phylloquinone).

The positive-charged group of the cationic repeat unit can be formed before or after the polymerization.

Cationic Polymers Having One Polymer Chain (One-Armed)

The antimicrobial cationic polymers can have a structure in accordance with formula (1):

$$Z'-P'-Z''  \quad (1),$$

wherein

Z' is a monovalent $C_1$-$C_{15}$ first end group, wherein Z' is linked to a backbone carbonyl group of P', Z" is a monovalent second end group selected from the group consisting of hydrogen and $C_1$-$C_{15}$ moieties, P' is a polymer chain consisting essentially of cationic carbonate repeat units, wherein i) P' has a degree of polymerization (DP) of about 5 to about 45, ii) each of the cationic carbonate repeat units comprises a backbone portion of the polymer chain and a $C_6$-$C_{25}$ cationic side chain linked to the backbone portion, and iii) the cationic side chain comprises a positive-charged heteroatom Q' of a quaternary ammonium group and/or quaternary phosphonium group, about 25% to about 100% of the cationic carbonate repeat units, designated first cationic carbonate repeat units, have a cationic side chain comprising 13 to about 25 carbons, and about 0% to about 75% of the cationic carbonate repeat units, designated second cationic carbonate repeat units, have a cationic side chain comprising 6 to 12 carbons.

Z' can be any suitable end group comprising 1 to 15 carbons. Z' comprises an oxygen, nitrogen or sulfur heteroatom that is linked to a backbone carbonyl of P' in the form of a carbonate, carbamate or thiocarbonate group, respectively. Z' can be a residue of an initiator used in a ring opening polymerization to form the cationic polymer. In an embodiment, Z' is a covalently bound form of $C_1$-$C_{15}$ compound. In another embodiment, Z' is a $C_1$-$C_{15}$ alkoxy or aryloxy group.

Z" is preferably linked to a backbone oxygen of P'. When Z" is hydrogen, the cationic polymer has a terminal hydroxy group. When Z" is not hydrogen, Z" can be any suitable end group comprising 1 to 15 carbons. In an embodiment, Z" is a covalently bound form of $C_1$-$C_{15}$ compound. In another embodiment, Z" is a $C_1$-$C_{15}$ acyl group.

The first cationic carbonate repeat units preferably comprise a cationic side chain having 13 to about 20 carbons, even more preferably 15 to about 20 carbons.

In an embodiment, P' consists essentially of 25 mol % to about 75 mol % of the first cationic carbonate repeat units, and about 75 mol % to about 25 mol % of the second cationic carbonate repeat units. In another embodiment, P' consists essentially of 25 mol % to about 50 mol % of the first cationic carbonate repeat units, and about 75 mol % to about 25 mol % of the second cationic carbonate repeat units.

The cationic carbonate repeat units can have a structure according to formula (2):

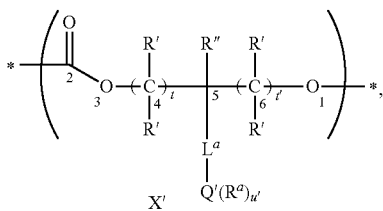

(2)

wherein $L^a$-$Q'(R^a)_{u'}$ is a $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, R'' is a monovalent radical selected from the group consisting of hydrogen, halogens, and alkyl groups comprising 1 to 6 carbons, t is a positive integer having a value of 0 to 2, t' is a positive integer having a value of 0 to 2, t and t' cannot both be zero, and X' is a negative-charged ion.

The starred bonds are attachment points to other portions of the polymer structure. The polymer backbone atoms of the cationic carbonate repeat unit are labeled 1 to 6 in formula (2). In this instance, the cationic side chain group is linked to backbone carbon 5 of the repeat unit. In an embodiment, t and t' are both 1, each R' is hydrogen, and R'' is methyl or ethyl.

In a cationic polymer of formula (1) whose cationic carbonate repeat units are of formula (2), the first cationic carbonate repeat units have a cationic side chain $L^a$-$Q'(R^a)_{u'}$ comprising 13 to about 25 carbons. The second cationic carbonate repeat units have a cationic side chain $L^a$-$Q'(R^a)_{u'}$ comprising 6 to 12 carbons.

The cationic carbonate repeat units can have a structure in accordance with formula (3):

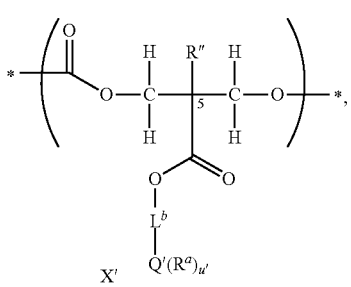

(3)

wherein $L^b$-$Q'(R^a)_{u'}$ is a $C_5$-$C_{24}$ cationic moiety comprising a quaternary ammonium group and/or quaternary phosphonium group, wherein $L^b$ is a divalent linking group comprising at least 2 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, R'' is a monovalent radical selected from the group consisting of hydrogen, halogens, and alkyl groups comprising 1 to 6 carbons, and X' is a negative-charged ion.

In this instance the cationic side chain group is C(=O)O-$L^b$-$Q'(R^a)_{u'}$, and C(=O)O-$L^b$ corresponds to divalent linking group $L^a$ of formula (2). The cationic side chain is linked to backbone carbon labeled 5.

In a cationic polymer of formula (1) whose cationic carbonate repeat units are of formula (3), the first cationic carbonate repeat units have a cationic side chain C(=O)O-$L^b$-$Q'(R^a)_{u'}$ comprising 13 to about 25 carbons. The second cationic carbonate repeat units have a cationic side chain C(=O)O-$L^b$-$Q'(R^a)_{u'}$ comprising 6 to 12 carbons.

The cationic repeat unit can have a structure in accordance with formula (4):

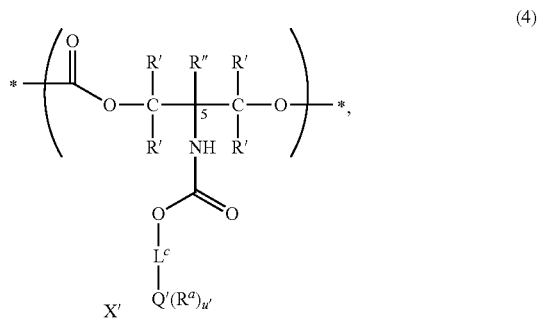

(4)

wherein $L^c$-$Q'(R^a)_{u'}$ is a $C_5$-$C_{24}$ cationic moiety comprising a quaternary ammonium group and/or quaternary phosphonium group, wherein $L^c$ is a divalent linking group comprising at least 2 carbons, Q' is a tetravalent positive-charged nitrogen or phosphorus, u' has a value of 1 to 3, and each $R^a$ is an independent radical having a valency of 1 to 3, wherein each $R^a$ comprises at least 1 carbon, each R' is an independent monovalent radical selected from the group consisting of hydrogen, halogens, methyl, and ethyl, R'' is a monovalent radical selected from the group consisting of hydrogen, halogens, and alkyl groups comprising 1 to 6 carbons, and X' is a negative-charged ion.

In this instance the cationic side chain is N(H)C(=O)O-$L^c$-$Q'(R^a)_{u'}$, and N(H)C(=O)O-$L^c$ corresponds to divalent linking group $L^a$ of formula (2). The cationic side chain is linked to backbone carbon labeled 5. Serinol and/or threoninol provide useful starting materials for the formation of repeat units of formula (4).

In a cationic polymer of formula (1) whose cationic carbonate repeat units are of formula (4), the first cationic carbonate repeat units have a cationic side chain N(H)C(=O)O-$L^c$-$Q'(R^a)_{u'}$ comprising 13 to about 25 carbons. The second cationic carbonate repeat units have a cationic side chain N(H)C(=O)O-$L^c$-$Q'(R^a)_{u'}$ comprising 6 to 12 carbons.

Using the cationic repeat unit of formula (2), the cationic polymers of formula (1) can have a structure in accordance with formula (5):

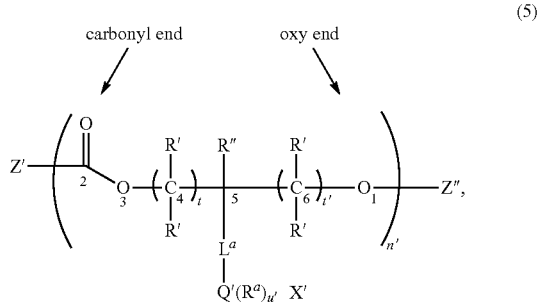

(5)

wherein:

n' represents the number of cationic carbonate repeat units, wherein n' has a value of about 5 to about 45, Z' is a monovalent $C_1$-$C_{15}$ first end group, Z" is a monovalent second end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a$-$Q'(R^a)_{u'}$ comprising 13 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 12 carbons.

As shown in formula (5), the polymer chain comprises a backbone portion comprising a oxycarbonyl group at a first end of the chain (referred to as the "carbonyl end"), and a backbone oxygen at a second end of the chain (referred to as the "oxy end"). The backbone atoms of the cationic carbonate repeat unit are shown numbered 1 to 6.

In formula (5), $L^a$ and $Q'(R^a)_{u'}$ of the first cationic carbonate repeat units can individually have 3 to about 22 carbons, with the proviso that $L^a$-$Q'(R^a)_{u'}$ has a total of 13 to about 25 carbons. Preferably, the $L^a$ group of the first cationic carbonate repeat units comprises 5 to about 12 carbons, or more preferably 8 to about 12 carbons. Preferably, $Q'(R^a)_{u'}$ of the first cationic carbonate repeat units comprise 3 to about 18 carbons, more preferably 4 to about 18 carbons.

Likewise, $L^a$ and $Q'(R^a)_{u'}$ of the second cationic carbonate repeat units of formula (5) can each have at least 3 carbons, with the proviso that $L^a$-$Q'(R^a)_{u'}$ has a total of 6 to 12 carbons.

In an embodiment, Z" is hydrogen. In another embodiment, the first cationic carbonate repeat units have a cationic side chain $L^a$-$Q'(R^a)_{u'}$ comprising 15 to about 20 carbons.

As more specific non-limiting examples, Z' can be benzyloxy and/or 4-methylbenzyloxy, and Z" can be hydrogen and/or acetyl.

The end groups Z' and/or Z", and end groups described below, can enhance antimicrobial efficacy and or stabilize the cationic polymer from potential unwanted side reactions (e.g., chain scission) caused by, for example, an unblocked nucleophilic hydroxy end group. Bulkier end groups can also provide hydrophobicity allowing control of the amphiphilic properties of the cationic polymers.

The antimicrobial cationic polymers can have a structure in accordance with formula (6):

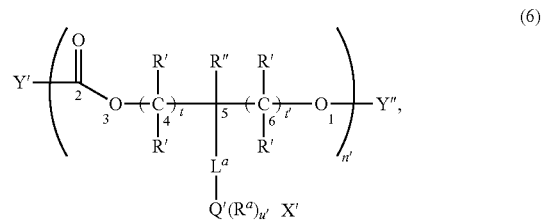

(6)

wherein n' represents the number of cationic carbonate repeat units, and n' has a value of about 5 to about 45, Y' is a monovalent first end group comprising a covalently bound form of a biologically active compound selected from the group consisting of steroids, non-steroid hormones, vitamins, and drugs, Y" is a monovalent second end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

$L^a$ and $Q'(R^a)_{u'}$ of the first cationic carbonate repeat units of formula (6) can individually have 3 to about 22 carbons, with the proviso that $L^a$-$Q'(R^a)_{u'}$ has a total of 10 to about 25 carbons. In an embodiment, the first cationic carbonate repeat units of formula (6) have a cationic side chain $L^a\text{-}Q'(R^a)_{u'}$ comprising 13 to about 25 carbons, and the second cationic carbonate repeat units have a cationic side chain $L^a\text{-}Q'(R^a)_{u'}$ comprising 6 to 12 carbons.

The biologically active compound can be stereospecific or non-stereospecific. In an embodiment, Y' comprises a covalently bound form of a steroid (e.g., cholesterol), designated S'. The steroid group can enhance biocompatibility of the cationic polymer.

In another embodiment, Y' comprises a covalently bound form of a vitamin, (e.g., alpha-tocopherol (a vitamin E compound) and/or ergocalciferol (vitamin D2)).

Y' can have a structure S'-L'-* wherein S' is a steroid group and L' is a single bond or any suitable divalent linking group comprising 1 to about 10 carbons. In this instance, L' links S' to the carbonyl end of the polycarbonate backbone.

The antimicrobial cationic polymers can have a structure in accordance with formula (7):

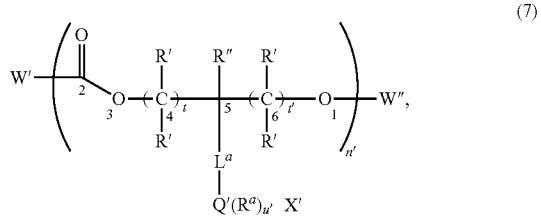

(7)

wherein n' represents the number of cationic carbonate repeat units, and n' has a value of about 5 to about 45, W' is a monovalent $C_1\text{-}C_{15}$ first end group, W" is a monovalent second end group comprising a covalently bound form of a biologically active compound selected from the group consisting of steroids, non-steroid hormones, vitamins, and drugs, each $L^a\text{-}Q'(R^a)_{u'}$ is an independent $C_6\text{-}C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a\text{-}Q'(R^a)_{u'}$ comprising 10 to about 25 carbons, and 0% to about 75% of the cationic carbonate repeat units of the cationic polymer, designated second cationic carbonate repeat units, have a cationic side chain $L^a\text{-}Q'(R^a)_{u'}$ comprising 6 to 9 carbons.

$L^a$ and $Q'(R^a)_{u'}$ of the first cationic carbonate repeat units of formula (7) can individually have 3 to about 22 carbons, with the proviso that $L^a\text{-}Q'(R^a)_{u'}$ has a total of 10 to about 25 carbons. In an embodiment, the first cationic carbonate repeat units of formula (7) have a cationic side chain $L^a\text{-}Q'(R^a)_{u'}$ comprising 13 to about 25 carbons, and the second cationic carbonate repeat units have a cationic side chain $L^a\text{-}Q'(R^a)_{u'}$ comprising 6 to 12 carbons.

W" can comprise a stereospecific or non-stereospecific form of the biologically active compound. In an embodiment, W" comprises a covalently bound form of cholesterol, alpha-tocopherol (a vitamin E compound), ergocalciferol (vitamin D2), or combinations thereof.

W" can have the general structure S'-L"-* wherein S' is a steroid group and L" is a single bond or any suitable divalent linking group comprising 1 to about 10 carbons. In this instance, L" links S' to the oxy end of the polycarbonate backbone.

The antimicrobial cationic polymer can be a random copolymer having a structure in accordance with formula (8):

(8), wherein

Z' is a monovalent $C_1\text{-}C_{15}$ first end group,

Z" is a monovalent second end group selected from the group consisting of hydrogen and $C_1\text{-}C_{15}$ moieties, P" is a polymer chain consisting essentially of I) about 85 mol % to 99.9 mol % of cationic carbonate repeat units, and II) 0.1 mol % to about 15 mol % of carbonate repeat units comprising a covalently bound form of a steroid and/or a vitamin compound, wherein i) P" has a degree of polymerization (DP) of about 5 to about 45, ii) each of the cationic carbonate repeat units comprises a polymer backbone portion and a cationic side chain portion linked to the polymer backbone portion, and iii) each cationic side chain portion comprises a positively charged heteroatom of a quaternary ammonium group and/or a quaternary phosphonium group, about 25% to 100% of the cationic carbonate repeat units of the cationic polymer, designated first cationic carbonate repeat units, have a cationic side chain $L^a\text{-}Q'(R^a)_{u'}$ comprising 10 to about 25 carbons, and 0% to about 75% of the cationic carbonate repeat units of the cationic polymer, designated second cationic carbonate repeat units, have a cationic side chain $L^a\text{-}Q'(R^a)_{u'}$ comprising 6 to 9 carbons.

$L^a$ and $Q'(R^a)_{u'}$ of the first cationic carbonate repeat units of formula (8) can individually have 3 to about 22 carbons, with the proviso that $L^a\text{-}Q'(R^a)_{u'}$ has a total of 10 to about 25 carbons. In an embodiment, the first cationic carbonate repeat units of formula (8) have a cationic side chain $L^a\text{-}Q'(R^a)_{u'}$ comprising 13 to about 25 carbons, and the second cationic carbonate repeat units have a cationic side chain $L^a\text{-}Q'(R^a)_{u'}$ comprising 6 to 12 carbons.

The antimicrobial cationic polymers of formula (8) can have a structure in accordance with formula (9):

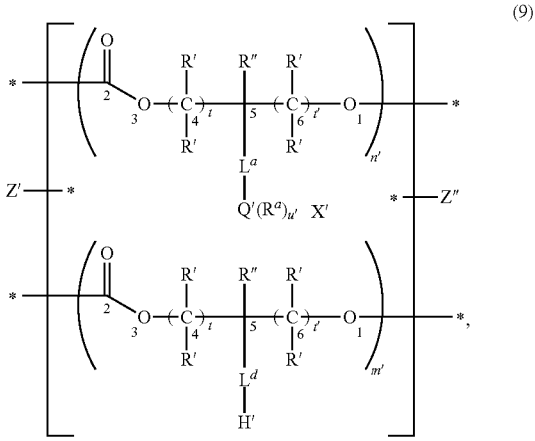

(9)

wherein n' represents the number of cationic carbonate repeat units, wherein n' has a value greater than 0, m' represents the number of carbonate repeat units, wherein m' has a value greater than 0, n'+m' has a value of about 5 to about 45, a ratio of m':n' is about 15:85 to about 0.1:99.9, Z' is a monovalent $C_1$-$C_{15}$ first end group, Z" is a monovalent second end group selected from the group consisting of hydrogen and $C_1$-$C_{15}$ moieties, each $L^d$ is an independent divalent linking group selected from the group consisting of single bond and monovalent radicals comprising 1 to about 10 carbons, each H' is an independent monovalent radical comprising a covalently bound form of a steroid and/or a vitamin compound, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

The vertical stacking of repeat units within the square brackets of formula (9) indicates a random distribution of repeat units within the polymer chain.

$L^a$ and $Q'(R^a)_{u'}$ of the first cationic carbonate repeat units of formula (9) can individually have 3 to about 22 carbons, with the proviso that $L^a$-$Q'(R^a)_{u'}$ has a total of 10 to about 25 carbons. In an embodiment, the first cationic carbonate repeat units of formula (9) have a cationic side chain $L^a$-$Q'(R^a)_{u'}$ comprising 13 to about 25 carbons, and the second cationic carbonate repeat units, have a cationic side chain $L^a$-$Q'(R^a)_{u'}$ comprising 6 to 12 carbons.

H' can comprise a covalently bound form of a vitamin E compound, vitamin D compound, or combinations thereof. Preferably, the vitamin compound is alpha-tocopherol (a vitamin E compound), ergocalciferol (vitamin D2), or a combination thereof.

The discussion that follows applies to all disclosed cationic polymer structures herein.

Exemplary non-limiting divalent $L^a$ groups include:

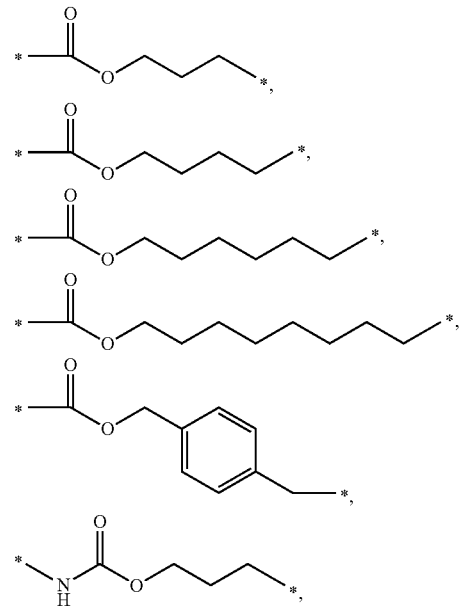

and combinations thereof. In these examples, the starred bonds of the carbonyl and carbamate nitrogen are linked to the polycarbonate backbone (e.g., the backbone carbon labeled 5 in the above cationic carbonate repeat units), and the starred bonds of the methylene groups are linked to Q'.

Together, $L^a$ and $Q'(R^a)_{u'}$ form a quaternary ammonium group or a quaternary phosphonium group, meaning the positive-charged heteroatom Q' is bonded to a carbon of $L^a$ and up to three independent $R^a$ groups.

Each $R^a$ comprises at least one carbon. Each $R^a$ can be a monovalent hydrocarbon substituent (e.g., methyl, ethyl, etc.), in which case u' is 3.

An $R^a$ can form a ring with Q', in which case the $R^a$ of the ring has a valency of 2. For example, $Q'(R^a)_{u'}$ can be:

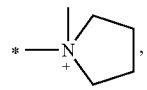

wherein the starred bond is linked to $L^a$, Q' is nitrogen, and u' is 2. In this example, a first $R^a$ is a divalent butylene group (*—$(CH_2)_4$—*), and a second $R^a$ is methyl.

$R^a$ can form a multi-cyclic moiety with Q'. For example $Q'(R^a)_{u'}$ can be:

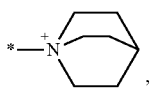

wherein the starred bond is linked to $L^a$, Q' is nitrogen, u' is 1, and $R^a$ is the fragment

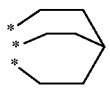

having a valency of 3.

The $R^a$ groups can also independently comprise oxygen, nitrogen, sulfur, and/or another heteroatom. In an embodiment, each $R^a$ is an independent monovalent branched or unbranched hydrocarbon substituent.

Exemplary non-limiting $R^a$ groups include methyl, ethyl, n-propyl, iso-propyl, n-butyl, iso-butyl, n-pentyl, n-hexyl, n-heptyl, n-octyl, and benzyl. The $R^a$ groups can be used in combination.

Exemplary non-limiting $Q'(R^a)_{u'}$ groups include:

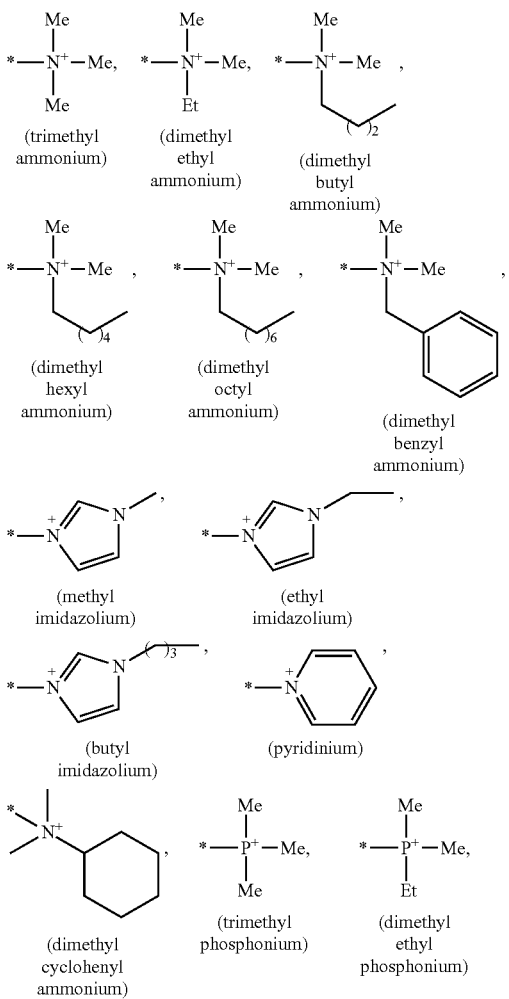

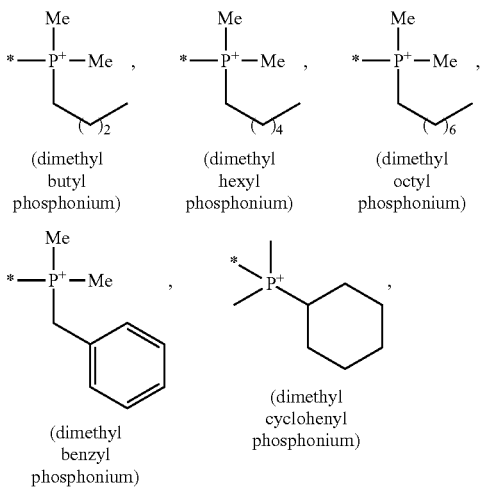

and combinations thereof.

In the foregoing examples, it should be understood that the positive-charged nitrogen and phosphorus are tetravalent, and the starred bond is linked to a carbon of $L^a$. The Q' groups can be present in the cationic polymer singularly or in combination.

Exemplary negative-charged ions X' include halides (e.g., chloride, bromide, and iodide), carboxylates (e.g., acetate and benzoate), and/or sulfonates (e.g., tosylate). The X' ions can be present singularly or in combination.

Exemplary non-limiting cationic carbonate repeat units include the following:

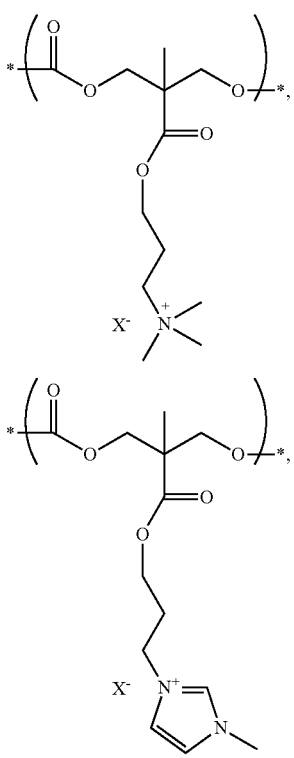

17
-continued
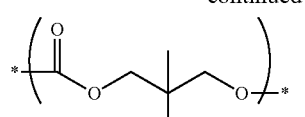
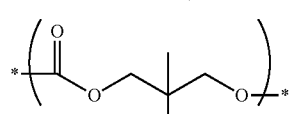
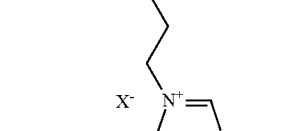
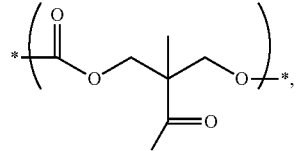
18
-continued
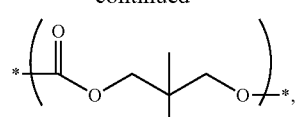
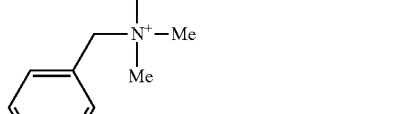
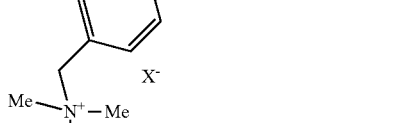
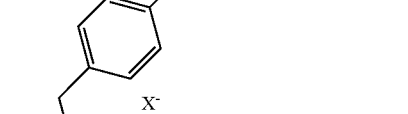

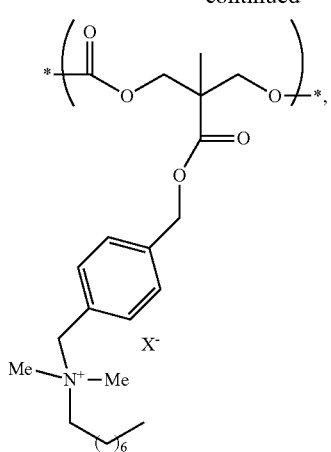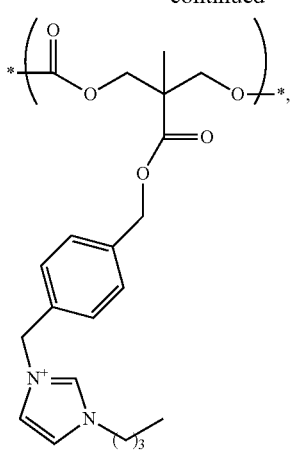

21
-continued
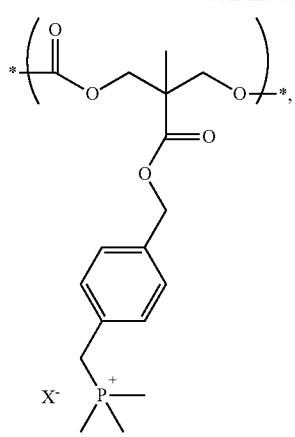
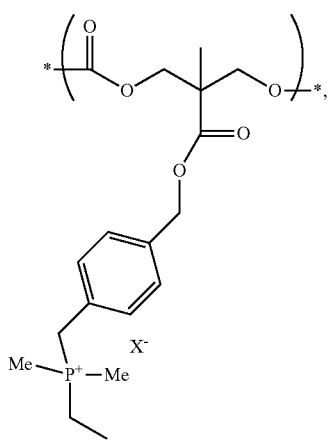
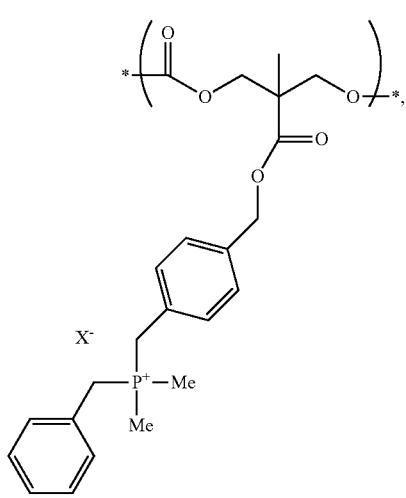
22
-continued
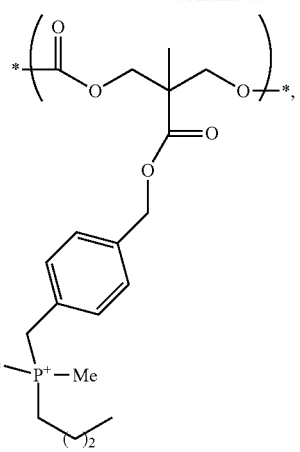
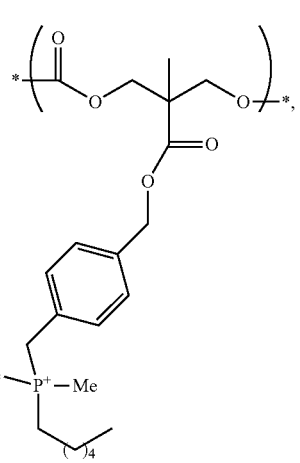
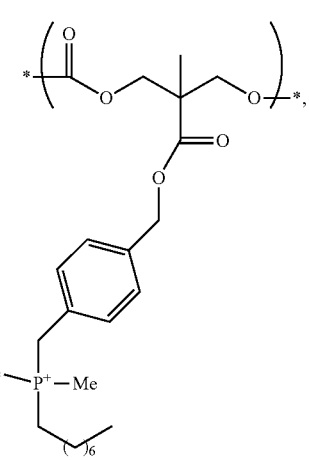

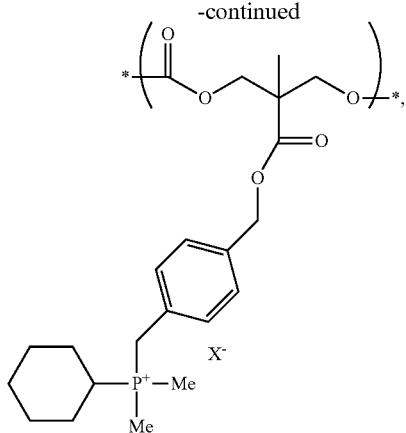

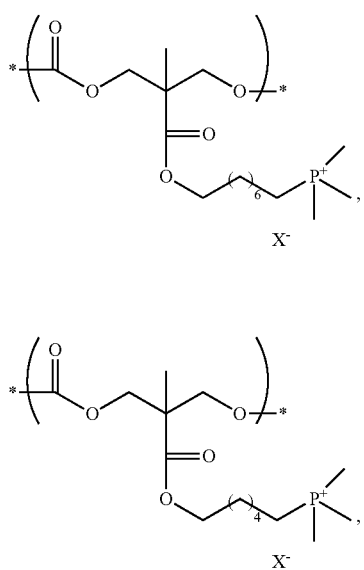

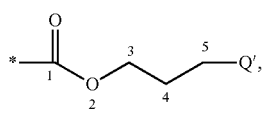

and combinations thereof, wherein $X^-$ is a negative-charged ion.

In general, antimicrobial activity of the cationic polymers is favored by spacing the positive-charged heteroatom Q' from the polycarbonate backbone in 25 mol % to 100 mol % of the cationic carbonate repeat units (first cationic carbonate repeat units) by a shortest path having 6 or more contiguously linked atomic centers from the polymer backbone. The shortest path is defined as the lowest number of contiguously linked atomic centers joining Q' to the polymer backbone. The contiguously linked atomic centers should be understood to be between the polycarbonate backbone and Q'. For example, if $L^a$-Q' is:

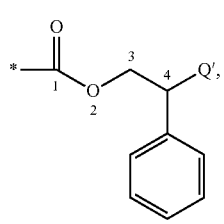

then the shortest path from the polymer backbone to Q' has 5 contiguously linked atomic centers, as numbered. The shortest path does not include the carbonyl oxygen. As another example, if $L^a$-Q' is

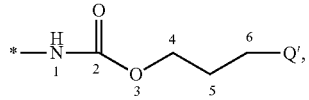

then the shortest path from the polymer backbone to Q' has 6 contiguously linked atomic centers, as numbered. The shortest path does not include the amide hydrogen and the carbonyl oxygen. As another example, if $L^a$-Q' is

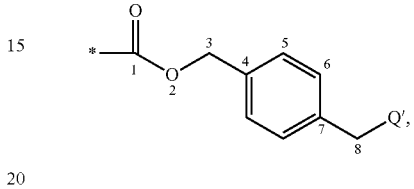

then the shortest path from the polymer backbone to Q' has 8 contiguously linked atomic centers, as numbered. The shortest path does not include two carbons of the aromatic ring and the carbonyl oxygen. As another example, if $L^a$-Q' is

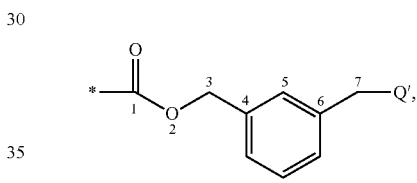

then the shortest path from the polymer backbone to Q' has 7 contiguously linked atomic centers, as numbered. The shortest path does not include three carbons of the aromatic ring and the carbonyl oxygen. Finally, as another example, if $L^a$-Q' is

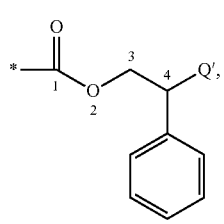

then the shortest path from the polymer backbone to Q' has 4 contiguously linked atomic centers, as numbered. The shortest path does not include the aromatic ring and the carbonyl oxygen.

Preferably, Q' of the first carbonate repeat units is spaced from the polymer backbone by a shortest path having 6 to about 18 contiguously linked atomic centers, and more preferably 8 to about 15 contiguously linked atomic centers.

The steroid group S' can originate from a naturally occurring human steroid, non-human steroid, and/or a synthetic steroid compound. Herein, a steroid group comprises a tetracyclic ring structure:

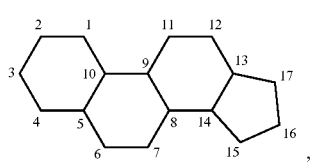

wherein the 17 carbons of the ring system are numbered as shown. The steroid group can comprise one or more additional substituents attached to one or more of the numbered ring positions. Each ring of the tetracyclic ring structure can independently comprise one or more double bonds.

Exemplary steroid groups include cholesteryl, from cholesterol, shown below without stereochemistry:

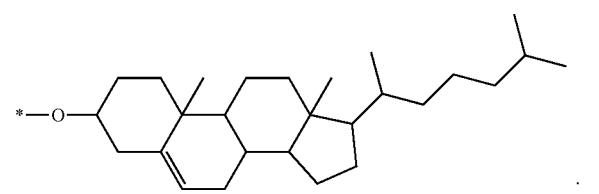 [SMILES: *OC1CCC2(C)C(=CCC3C2CCC2(C)C(C(C)CCCC(C)C)CCC32)C1]

Non-limiting stereospecific structures of cholesteryl include

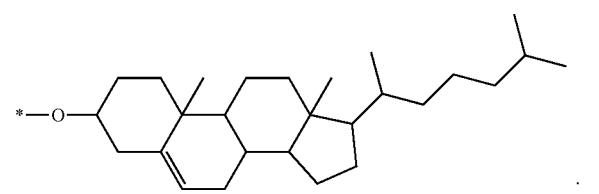 [SMILES: *OC1CCC2(C)C(=CCC3C2CCC2(C)C(C(C)CCCC(C)C)CCC32)C1]

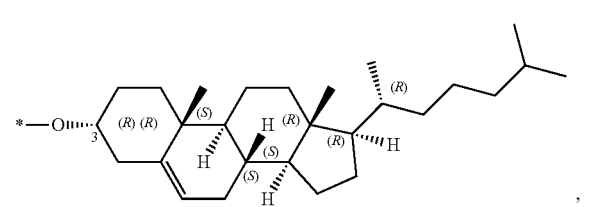, and/or

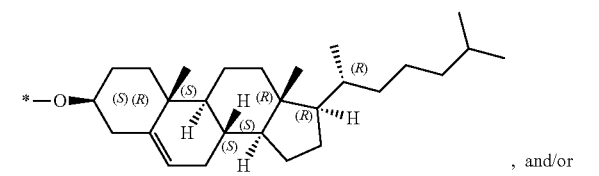

where the R,S stereoconfiguration of each stereospecific asymmetric center is labeled.

Additional non-limiting steroid groups include

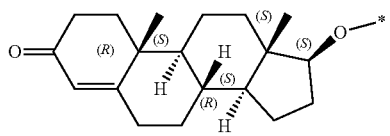

from testosterone,

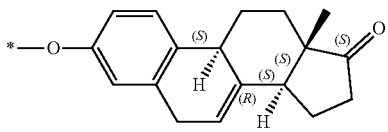

from equilin,

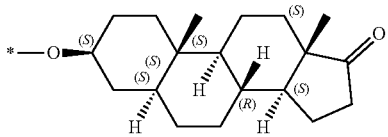

from epiandrosterone,

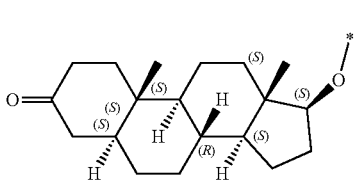

from dihydrotestosterone,

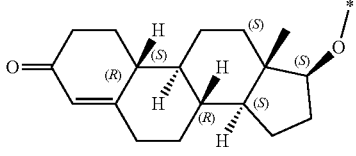

from nandrolone,

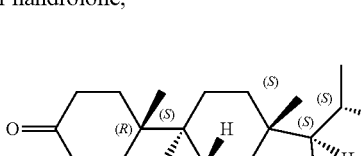

from dihydroprogesterone,

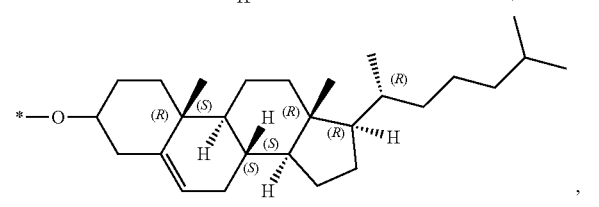

from pregnenolone,

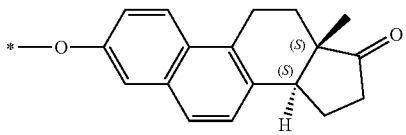

from equilenin,

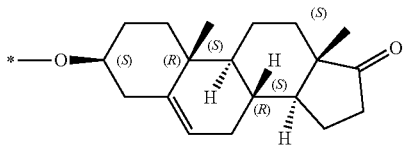

from dehydroepiandrosterone,

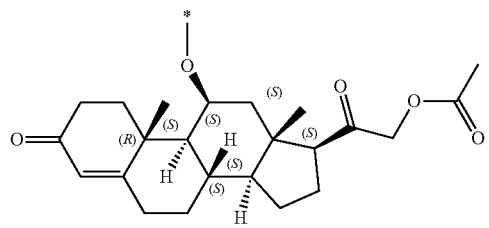

from corticosterone acetate,

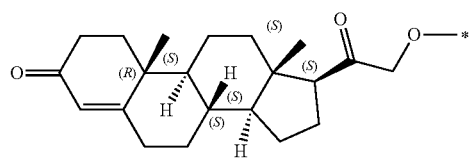

from deoxycorticosterone, and

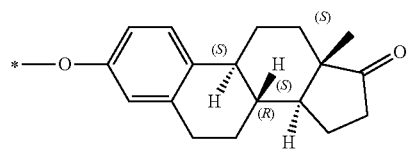

from estrone.

The starred bonds represent attachment points. For example, the starred bond of each of the above steroid groups can be linked to a terminal carbonyl group of the polycarbonate backbone by way of a divalent linking group L'. Alternatively, the starred bond of the steroid group can be directly linked to a terminal carbonyl group of the polycarbonate backbone (i.e., L' can be a single bond).

Those of skill in the art will recognize that each asymmetric center of the steroid groups can be present as the R stereoisomer, S stereoisomer, or as a mixture of R and S stereoisomers. Additional steroid groups S' include the various stereoisomers of the above structures. The cationic polymer can comprise a steroid group as a single stereoisomer or as a mixture of stereoisomers.

In an embodiment, S' is cholesteryl group, wherein the cholesteryl group is a mixture of isomers

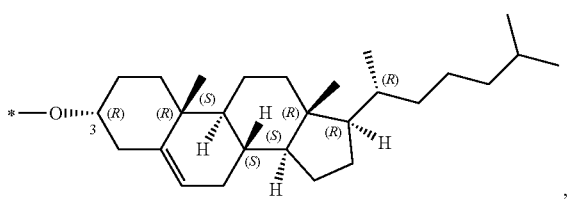

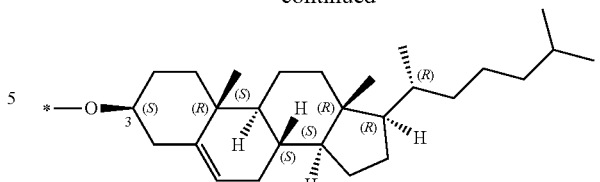

indicated by the structure

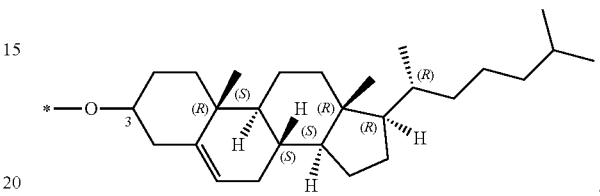

More specific steroid-containing cationic polymers have a structure in accordance with formula (10):

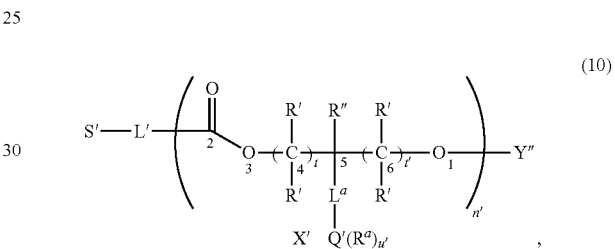

wherein n' represents the number of cationic carbonate repeat units, and has a value of about 5 to about 45, S'-L' is a first end group, wherein L' is a single bond or a divalent linking group comprising 1 to about 10 carbons, and S' comprises a covalently bound form of a steroid, Y" is a monovalent second end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

In formula (10), when L' is a single bond, S' is linked directly to the terminal carbonyl group of the polycarbonate backbone. In an embodiment, L' is a divalent linking group comprising an alkylene oxide selected from the group consisting of ethylene oxide (*—$CH_2CH_2O$—*), propylene oxide *—$CH_2CH_2CH_2O$—*, and/or tri(ethylene oxide) (*—$CH_2CH_2OCH_2CH_2OCH_2CH_2O$—*), wherein the starred bond of the oxygen is linked to the terminal carbonyl group of the polycarbonate backbone and the starred bond of the carbon is linked to S'.

$L^a$ and $Q'(R^a)_{u'}$ of the first cationic carbonate repeat units of formula (10) can individually have 3 to about 22 carbons, with the proviso that $L^a$-$Q'(R^a)_{u'}$ has a total of 10 to about 25 carbons. In an embodiment, the first cationic carbonate repeat units of formula (10) have a cationic side chain $L^a$-$Q'(R^a)_{u'}$ comprising 13 to about 25 carbons, and the second cationic carbonate repeat units, have a cationic side chain $L^a$-$Q'(R^a)_{u'}$ comprising 6 to 12 carbons.

The steroid-containing cationic polymers can comprise one or a combination of the cationic carbonate repeat units described further above.

The steroid-containing cationic polymers can have a structure in accordance with formula (11):

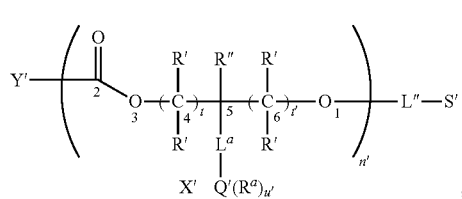

(11)

wherein n' represents the number of cationic carbonate repeat units, and has a value of about 5 to about 45, Y' is a monovalent $C_1$-$C_{15}$ first end group, S'-L" is a second end group, wherein L" is a single bond or a divalent linking group comprising 1 to about 10 carbons and S' comprises a covalently bound form of a steroid, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

The group S'-L" is linked to the oxy end of the polycarbonate backbone, and Y' is linked to the carbonyl end of the polycarbonate backbone.

$L^a$ and $Q'(R^a)_{u'}$ of the first cationic carbonate repeat units of formula (11) can individually have 3 to about 22 carbons, with the proviso that $L^a$-$Q'(R^a)_{u'}$ has a total of 10 to about 25 carbons. In an embodiment, the first cationic carbonate repeat units of formula (11) have a cationic side chain $L^a$-$Q'(R^a)_{u'}$ comprising 13 to about 25 carbons, and the second cationic carbonate repeat units, have a cationic side chain $L^a$-$Q'(R^a)_{u'}$ comprising 6 to 12 carbons.

Cationic Polymers Having Two Cationic Polymer Chains (Two-Armed Cationic Polymers)

The antimicrobial cationic polymers can have a structure in accordance with formula (12):

(12), wherein

C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each polymer chain $P^b$ consists essentially of cationic carbonate repeat units, wherein i) the cationic polymer comprises a total of 5 to about 45 cationic carbonate repeat units, ii) each of the cationic carbonate repeat units comprises a backbone portion of the polymer chain and a cationic side chain linked to the backbone portion, and iii) the cationic side chain comprises a positive-charged heteroatom Q' of a quaternary ammonium group and/or quaternary phosphonium group, about 25% to 100% of all the cationic carbonate repeat units of the cationic polymer, designated first cationic carbonate repeat units, have a cationic side chain comprising 10 to about 25 carbons, and 0% to about 75% of the cationic carbonate repeat units of the cationic polymer, designated second cationic carbonate repeat units, have a cationic side chain comprising 6 to 9 carbons.

$L^a$ and $Q'(R^a)_{u'}$ of the first cationic carbonate repeat units of formula (12) can individually have 3 to about 22 carbons, with the proviso that $L^a$-$Q'(R^a)_{u'}$ has a total of 10 to about 25 carbons. In an embodiment, the first cationic carbonate repeat units of formula (12) have a cationic side chain $L^a$-$Q'(R^a)_{u'}$ comprising 13 to about 25 carbons, and the second cationic carbonate repeat units have a cationic side chain $L^a$-$Q'(R^a)_{u'}$ comprising 6 to 12 carbons.

In an embodiment, each $Z^c$ is hydrogen. In another embodiment, the positive-charged heteroatom Q' of the first cationic carbonate repeat units is spaced from the backbone portion by a shortest path having 6 to about 15 contiguously linked atomic centers between Q' and the backbone portion.

More specific cationic polymers of formula (12) have a structure according to formula (13):

(13)

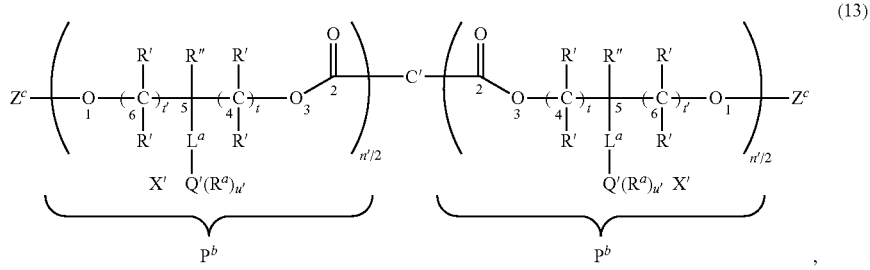

wherein n' represents the total number of cationic carbonate repeat units of the cationic polymer, and has a value of about 5 to about 45, C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, the polymer chains $P^b$ consist essentially of the cationic carbonate repeat units, each $Z^c$ is an independent monovalent end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion; and wherein about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

$L^a$ and $Q'(R^a)_{u'}$ of the first cationic carbonate repeat units of formula (13) can individually have 3 to about 22 carbons, with the proviso that $L^a$-$Q'(R^a)_{u'}$ has a total of 10 to about 25 carbons. In an embodiment, the first cationic carbonate repeat units of formula (13) have a cationic side chain $L^a$-$Q'(R^a)_{u'}$ comprising 13 to about 25 carbons, and the second cationic carbonate repeat units, have a cationic side chain $L^a$-$Q'(R^a)_{u'}$ comprising 6 to 12 carbons.

C' can be a residue of a di-nucleophilic initiator used to prepare the cationic polymer by ring opening polymerization.

In another antimicrobial polymer, the fragment linking the two cationic polymer chains comprises a covalently bound form of a biologically active compound selected from the group consisting of steroids, non-steroid hormones, vitamins, and drugs. These antimicrobial cationic polymers have a structure in accordance with formula (14):

wherein

C" is a divalent linking group joining polymer chains $P^b$, wherein C" comprises i) a first heteroatom linked to a first polymer chain $P^b$, wherein the first heteroatom is selected from the group consisting of nitrogen, oxygen, and sulfur, ii) a second heteroatom linked to a second polymer chain $P^b$, wherein the second heteroatom is selected from the group consisting of nitrogen, oxygen, and sulfur, and iii) a covalently bound form of a compound selected from the group consisting of steroids, non-steroid hormones, vitamins, and drugs, each $Z^c$ is an independent monovalent end group selected from the group consisting of hydrogen and $C_1$-$C_{15}$ moieties, each polymer chain $P^b$ consists essentially of cationic carbonate repeat units, wherein i) the cationic polymer comprises a total of 5 to about 45 cationic carbonate repeat units, ii) each of the cationic carbonate repeat units comprises a backbone portion of the polymer chain and a $C_6$-$C_{25}$ cationic side chain linked to the backbone portion, and iii) the cationic side chain comprises a positive-charged heteroatom Q' of a quaternary ammonium group and/or quaternary phosphonium group, about 25% to 100% of the cationic carbonate repeat units of the cationic polymer, designated first cationic carbonate repeat units, have a cationic side chain group comprising 10 to about 25 carbons, and 0% to about 75% of the cationic carbonate repeat units of the cationic polymer, designated second cationic carbonate repeat units, have a cationic side chain group comprising 6 to 9 carbons.

$L^a$ and $Q'(R^a)_{u'}$ of the first cationic carbonate repeat units of formula (14) can individually have 3 to about 22 carbons, with the proviso that $L^a$-$Q'(R^a)_{u'}$ has a total of 10 to about 25 carbons. In an embodiment, the first cationic carbonate repeat units of formula (14) have a cationic side chain comprising 13 to about 25 carbons, and the second cationic carbonate repeat units, have a cationic side chain comprising 6 to 12 carbons.

The positive-charged heteroatom Q' of the first cationic carbonate repeat units can be spaced from the backbone portion by a shortest path having 6 to about 18 contiguously linked atomic centers between Q' and the backbone portion.

In an embodiment, C" comprises a covalently bound form of cholesterol. In another embodiment, C" comprises a covalently bound form of a vitamin selected from the group consisting of alpha-tocopherol, ergocalciferol, and combinations thereof.

More specific cationic polymers of formula (14) have a structure according to formula (15):

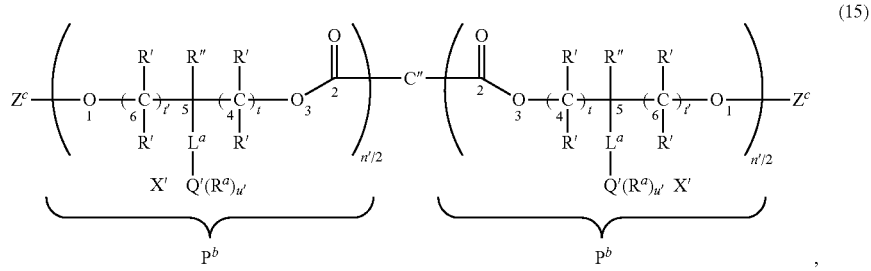

wherein
n' represents the total number of cationic carbonate repeat units of the cationic polymer, and has a value of about 5 to about 45, C" is a divalent linking group joining polymer chains $P^b$, wherein C" comprises i) a first heteroatom linked to a first polymer chain $P^b$, wherein the first heteroatom is selected from the group consisting of nitrogen, oxygen, and sulfur, ii) a second heteroatom linked to a second polymer chain $P^b$, wherein the second heteroatom is selected from the group consisting of nitrogen, oxygen, and sulfur, and iii) a covalently bound form of a compound selected from the group consisting of steroids, non-steroid hormones, vitamins, and drugs, each of the polymer chains $P^b$ consists essentially of cationic carbonate repeat units, each $Z^c$ is an independent monovalent end group selected from the group consisting of hydrogen and $C_1$-$C_{15}$ moieties, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and
each X' is an independent negative-charged ion;
and wherein
about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

$L^a$ and $Q'(R^a)_{u'}$ of the first cationic carbonate repeat units of formula (15) can individually have 3 to about 22 carbons, with the proviso that $L^a$-$Q'(R^a)_{u'}$ has a total of 10 to about 25 carbons. In an embodiment, the first cationic carbonate repeat units of formula (15) have a cationic side chain $L^a$-$Q'(R^a)_{u'}$ comprising 13 to about 25 carbons, and the second cationic carbonate repeat units, have a cationic side chain $L^a$-$Q'(R^a)_{u'}$ comprising 6 to 12 carbons.

The antimicrobial cationic polymers can have a structure in accordance with formula (16):

$$Z^c-P^c-C'-P^c-Z^c \qquad (16),$$

wherein
C' is a $C_2$-$C_{15}$ divalent linking group joining polymer chains $P^c$, wherein C' comprises i) a first heteroatom linked to a first polymer chain $P^c$, wherein the first heteroatom is selected from the group consisting of nitrogen, oxygen, and sulfur, and ii) a second heteroatom linked to a second polymer chain $P^c$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each $P^c$ is a polymer chain consisting essentially of I) about 85 mol % to 99.9 mol % of cationic carbonate repeat units, and II) 0.1 mol % to about 15 mol % of a carbonate repeat unit comprising a covalently bound form of a steroid and/or a vitamin compound, wherein i) the cationic polymer has a total number of repeat units of about 5 to about 45, ii) each of the cationic carbonate repeat units comprises a polymer backbone portion and a $C_6$-$C_{25}$ cationic side chain portion linked to the polymer backbone portion, and iii) each cationic side chain portion comprises a positive-charged heteroatom Q' of a quaternary ammonium group and/or quaternary phosphonium group, about 25% to 100% of the cationic carbonate repeat units of the cationic polymer, designated first cationic carbonate repeat units, have a cationic side chain group comprising 10 to about 25 carbons, and 0% to about 75% of the cationic carbonate repeat units of the cationic polymer, designated second cationic carbonate repeat units, have a cationic side chain group comprising 6 to 9 carbons.

$L^a$ and $Q'(R^a)_{u'}$ of the first cationic carbonate repeat units of formula (16) can individually have 3 to about 22 carbons, with the proviso that $L^a$-$Q'(R^a)_{u'}$ has a total of 10 to about 25 carbons. In an embodiment, the first cationic carbonate repeat units of formula (16) have a cationic side chain comprising 13 to about 25 carbons, and the second cationic carbonate repeat units have a cationic side chain comprising 6 to 12 carbons.

The cationic polymers of formula (16) can have a structure according to formula (17):

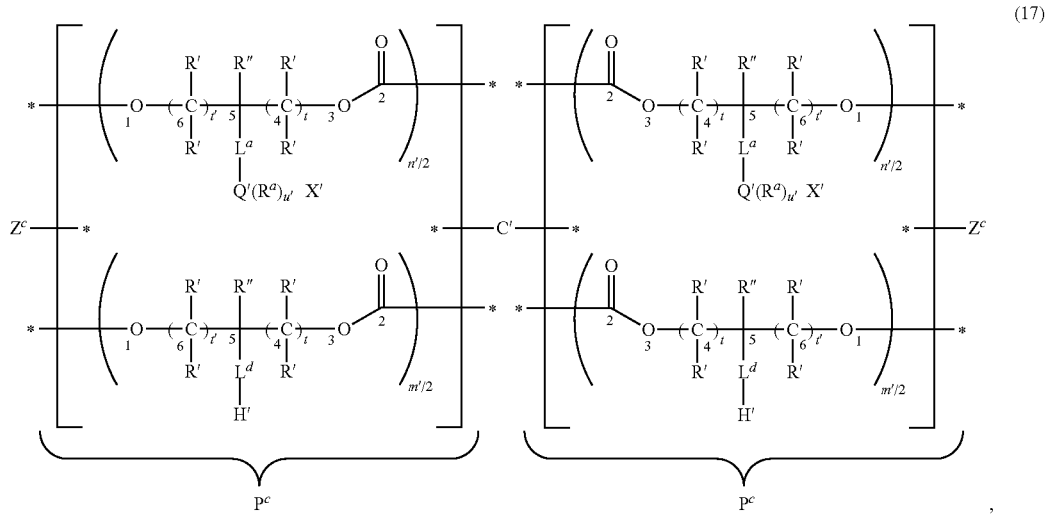

(17)

wherein n' represents the total number of cationic carbonate repeat units, wherein n' has a value greater than 0, m' represents the total number of carbonate repeat units, wherein m' has a value greater than 0, n'+m' has a value of about 5 to about 45, and a ratio m':n' is about 15:85 to about 0.1:99.9, C' is a $C_2$-$C_{15}$ non-polymeric divalent linking group joining polymer chains $P^c$, wherein C' comprises i) a first heteroatom linked to a first polymer chain $P^c$, wherein the first heteroatom is selected from the group consisting of nitrogen, oxygen, and sulfur, and ii) a second heteroatom linked to a second polymer chain $P^c$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each $L^d$ is an independent divalent linking group selected from the group consisting of single bond and monovalent radicals comprising 1 to about 10 carbons, each H' is an independent monovalent radical comprising a covalently bound form of a steroid and/or a vitamin compound, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

$L^a$ and $Q'(R^a)_{u'}$ of the first cationic carbonate repeat units of formula (17) can individually have 3 to about 22 carbons, with the proviso that $L^a$-$Q'(R^a)_{u'}$ has a total of 10 to about 25 carbons. In an embodiment, the first cationic carbonate repeat units of formula (17) have a cationic side chain $L^a$-$Q'(R^a)_{u'}$ comprising 13 to about 25 carbons, and the second cationic carbonate repeat units have a cationic side chain $L^a$-$Q'(R^a)_{u'}$ comprising 6 to 12 carbons.

H' can comprise a covalently bound form of a vitamin E compound, vitamin D compound, or combinations thereof. In an embodiment, H' comprises a covalently bound form of a vitamin compound selected from the group consisting of alpha-tocopherol (a vitamin E compound), ergocalciferol (vitamin D2), and combinations thereof.

The antimicrobial cationic polymers can have a structure in accordance with formula (18):

$$Y^c-P^b-C'-P^b-Y^d \qquad (18),$$

wherein

C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, $Y^c$ is an independent monovalent first end group selected from the group consisting of hydrogen, groups comprising a covalently bound form of a steroid, and groups comprising a covalently bound form of a vitamin, $Y^d$ is an independent monovalent second end group selected from the group consisting of hydrogen, groups comprising a covalently bound form of a steroid, and groups comprising a covalently bound form of a vitamin, each polymer chain $P^b$ consists essentially of cationic carbonate repeat units, wherein i) the cationic polymer comprises a total of 5 to about 45 cationic carbonate repeat units, ii) each of the cationic carbonate repeat units comprises a backbone portion of the polymer chain and a cationic side chain linked to the backbone portion, and iii) the cationic side chain comprises a positive-charged heteroatom Q' of a quaternary ammonium group and/or quaternary phosphonium group, about 25% to 100% of all the cationic carbonate repeat units of the cationic polymer, designated first cationic carbonate repeat units, have a cationic side chain comprising 10 to about 25 carbons, and 0% to about 75% of the cationic carbonate repeat units of the cationic polymer, designated second cationic carbonate repeat units, have a cationic side chain comprising 6 to 9 carbons.

$L^a$ and $Q'(R^a)_{u'}$ of the first cationic carbonate repeat units of formula (18) can individually have 3 to about 22 carbons, with the proviso that $L^a$-$Q'(R^a)_{u'}$ has a total of 10 to about 25 carbons. In an embodiment, the first cationic carbonate repeat units of formula (18) have a cationic side chain $L^a$-$Q'(R^a)_{u'}$ comprising 13 to about 25 carbons, and the second cationic carbonate repeat units have a cationic side chain $L^a$-$Q'(R^a)_{u'}$ comprising 6 to 12 carbons.

$Y^c$ and/or $Y^d$ can comprise a covalently bound form of a steroid and/or a vitamin.

More specific cationic polymers of formula (18) have a structure according to formula (19):

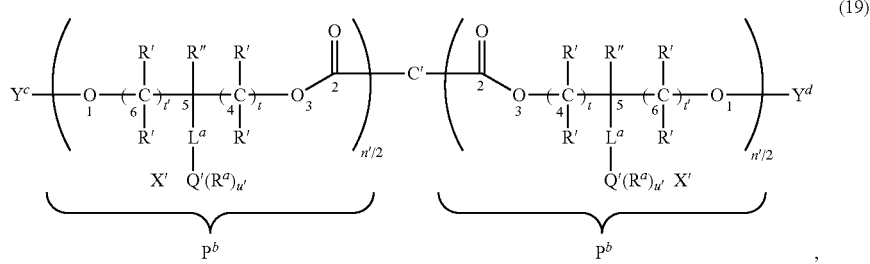

wherein n' represents the total number of cationic carbonate repeat units of the cationic polymer, and has a value of about 5 to about 45, C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, the polymer chains $P^b$ consist essentially of the cationic carbonate repeat units, $Y^c$ is an independent monovalent end group selected from the group consisting of hydrogen, groups comprising a covalently bound form of a steroid, and groups comprising a covalently bound form of a vitamin, $Y^d$ is an independent monovalent end group selected from the group consisting of hydrogen, groups comprising a covalently bound form of a steroid, and groups comprising a covalently bound form of a vitamin, each $L^a$-$Q'(R^a)_{u'}$ is an independent $C_6$-$C_{25}$ cationic side chain comprising a quaternary ammonium group and/or quaternary phosphonium group, wherein $L^a$ is a divalent linking group comprising at least 3 carbons, Q' is a tetravalent positive-charged nitrogen or phosphorus, u' has a value of 1 to 3, each $R^a$ is an independent radical having a valency of 1 to 3, and each $R^a$ comprises at least 1 carbon, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, no cationic carbonate repeat unit has t=0 and t'=0, and each X' is an independent negative-charged ion;

and wherein about 25% to 100% of the cationic carbonate repeat units of the cationic polymer, designated first cationic carbonate repeat units, have a cationic side chain $L^a$-$Q'(R^a)_{u'}$ comprising 10 to about 25 carbons, and 0% to about 75% of the cationic carbonate repeat units of the cationic polymer, designated second cationic carbonate repeat units, have a cationic side chain $L^a$-$Q'(R^a)_{u'}$ comprising 6 to 9 carbons.

$L^a$ and $Q'(R^a)_{u'}$ of the first cationic carbonate repeat units of formula (19) can individually have 3 to about 22 carbons, with the proviso that $L^a$-$Q'(R^a)_{u'}$ has a total of 10 to about 25 carbons. In an embodiment, the first cationic carbonate repeat units of formula (19) have a cationic side chain $L^a$-$Q'(R^a)_{u'}$ comprising 13 to about 25 carbons, and the second cationic carbonate repeat units, have a cationic side chain $L^a$-$Q'(R^a)_{u'}$ comprising 6 to 12 carbons.

Cation-Forming Cyclic Carbonate Monomers

A preferred method of preparing the disclosed cationic polymers utilizes a cyclic carbonate monomer capable of forming a cationic moiety before or after the polymerization. These are referred to as cation-forming monomers, which have the formula (20):

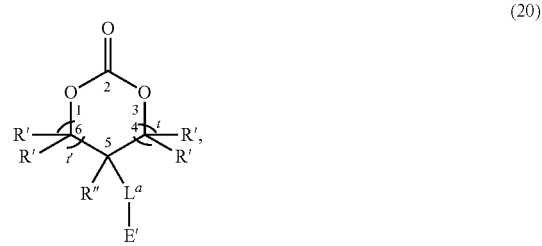

wherein the ring atoms are shown numbered 1 to 6, $L^a$ is a divalent linking group comprising at least 3 carbons, E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises 1 or more carbons, and together $Q'(R^a)_{u'}$ and $L^a$ comprise 6 to about 25 carbons, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, t is a positive integer having a value of 0 to 2, t' is a positive integer having a value of 0 to 2, and t and t' cannot both be zero.

The cation-forming monomers of formula (20) have a ring substituent $L^a$-E'. This ring substituent $L^a$-E' becomes a side chain of the initial polymer formed by the ring opening polymerization of the cation-forming monomer. E' can be an electrophilic and/or nucleophilic group so long as the side chain $L^a$-E' is capable of reacting to produce a $C_6$-$C_{25}$ cationic side chain $L^a$-$Q'(R^a)_{u'}$ of the cationic polymer. Preferably, E' is a leaving group capable of reacting with a tertiary amine to form a quaternary ammonium group, and/or reacting with a tertiary phosphine to form a quaternary phosphonium group.

The cation-forming monomers can be stereospecific or non-stereospecific.

In an embodiment, t and t' of formula (20) are each 1, each R' at carbon 4 is hydrogen, each R' at carbon 6 is hydrogen, and R" at carbon 5 is selected from the group consisting of hydrogen, methyl, and ethyl.

Ring opening polymerization of cation-forming monomers of formula (20) produces an initial polycarbonate having a repeat unit according to formula (21):

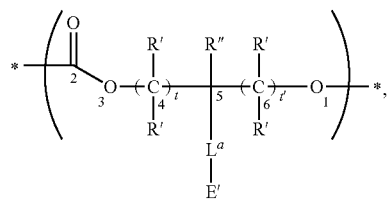

wherein backbone atoms are shown numbered 1 to 6, $L^a$ is a divalent linking group comprising at least 3 carbons, E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^a$ comprise 6 to about 25 carbons, each R' is an independent monovalent radical selected from the group consisting of hydrogen, halogens, methyl, and ethyl, R" is a monovalent radical selected from the group consisting of hydrogen, halogens, and alkyl groups comprising 1 to 6 carbons, t is a positive integer having a value of 0 to 2, t' is a positive integer having a value of 0 to 2, and t and t' cannot both be zero.

More specific cation-forming monomers have the formula (22):

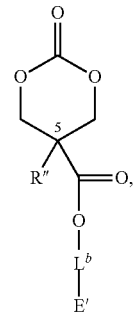

wherein ring atom 5 is labeled, $L^b$ is a divalent linking group comprising at least 2 carbons, E' is a substituent capable of reacting to produce a cationic moiety $Q'(R^a)_{u'}$ linked to $L^b$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^b$ comprise 5 to about 24 carbons, and R" is a monovalent radical selected from the group consisting of hydrogen, halogens, and alkyl groups comprising 1 to 6 carbons.

Ring opening polymerization of cation-forming monomers of formula (22) produces a polycarbonate having a repeat unit according to formula (23):

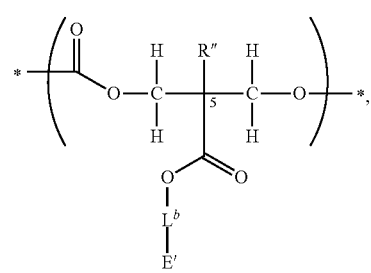

wherein backbone atom 5 is labeled, $L^b$ is a divalent linking group comprising at least 2 carbons, E' is a substituent capable of reacting to produce a cationic moiety $Q'(R^a)_{u'}$ linked to $L^b$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^b$ comprise 5 to about 24 carbons, and R" is a monovalent radical selected from the group consisting of hydrogen, halogens, and alkyl groups comprising 1 to 6 carbons.

The cation-forming monomers can have the formula (24):

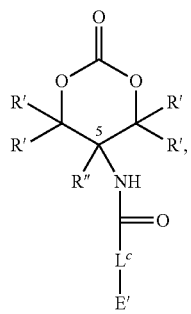
(24)

wherein
ring atom 5 is labeled,
$L^c$ is a divalent linking group comprising at least 2 carbons,
E' is a substituent capable of reacting to produce a cationic moiety $Q'(R^a)_{u'}$ linked to $L^c$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^c$ comprise 5 to about 24 carbons,
each R' is an independent monovalent radical selected from the group consisting of hydrogen, halogens, methyl, and ethyl, and
R" is a monovalent radical selected from the group consisting of hydrogen, halogens, and alkyl groups comprising 1 to 6 carbons.

Ring opening polymerization of cation-forming monomers of formula (24) produces an initial polycarbonate having a repeat unit according to formula (25):

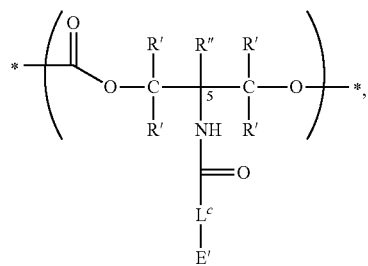
(25)

wherein
backbone atom 5 is labeled,
$L^c$ is a divalent linking group comprising at least 2 carbons,
E' is a substituent capable of reacting to produce a cationic moiety $Q'(R^a)_{u'}$ linked to $L^c$, wherein Q' is a tetravalent positive-charged nitrogen or phosphorus, u' has a value of 1 to 3, each $R^a$ is an independent radical having a valency of 1 to 3, wherein each $R^a$ comprises at least 1 carbon, and together $Q'(R^a)_{u'}$ and $L^c$ comprise 5 to about 24 carbons,
each R' is an independent monovalent radical selected from the group consisting of hydrogen, halogens, methyl, and ethyl, and
R" is a monovalent radical selected from the group consisting of hydrogen, halogens, and alkyl groups comprising 1 to 6 carbons.

Exemplary cation-forming monomers include the cyclic carbonate monomers of Table 1.

TABLE 1

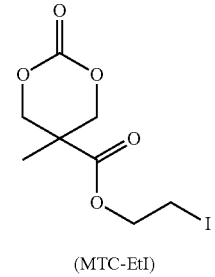
(MTC-EtI)

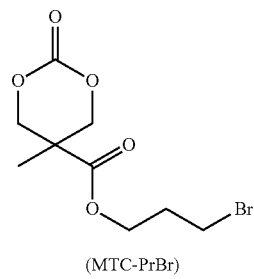
(MTC-PrBr)

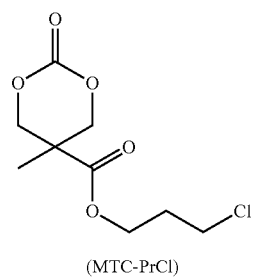
(MTC-PrCl)

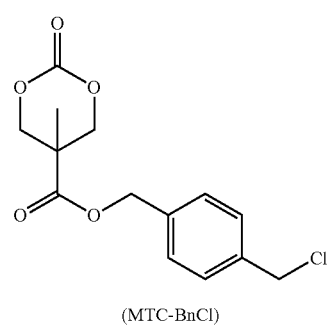
(MTC-BnCl)

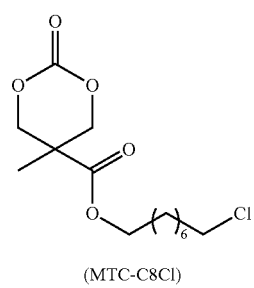
(MTC-C8Cl)

Mononucleophilic Initiators for One-Armed Cationic Polymers

Nucleophilic initiators for ROP generally include alcohols, amines, and/or thiols. For the above described cationic polymers having one cationic polymer chain (on-armed cationic polymers), the ROP initiator is a mono-nucleophilic non-polymeric initiator (e.g., ethanol, n-butanol, benzyl alcohol, and the like). In some instances, the ROP initiator can comprise a covalently bound form of a biologically active compound selected from the group consisting of steroids, non-steroid hormones, vitamins, and drugs. For example, mono-nucleophilic ROP initiators include cholesterol, alpha-tocopherol, and ergocalciferol.

More specific mono-nucleophilic ROP initiators comprise a steroid group S'. The initiator can have a structure according to formula (26):

$$S'-L^e \qquad (26),$$

wherein S' is a steroid group and $L^e$ is a monovalent group comprising i) 1 to about 10 carbons and ii) a nucleophilic initiating group for the ROP. Non-limiting examples of ROP initiators of formula (26) include Chol-OPrOH:

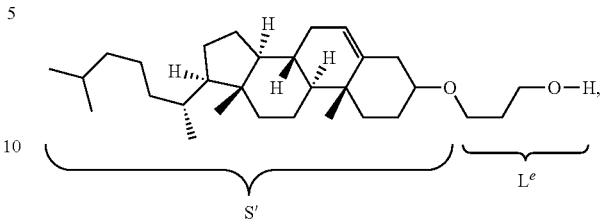

and Chol-OTEG-OH:

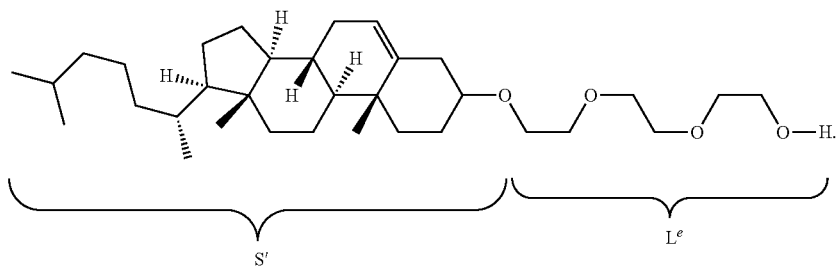

In the above examples, S' is a cholesteryl group. Using the preferred method of preparing the cationic polymers described below, the S'-L'-* fragment of the cationic polymer is a residue of the ROP initiator when linked to the carbonyl end of the polycarbonate backbone. The S'-L'-* fragment derived from Chol-OPrOH has the structure:

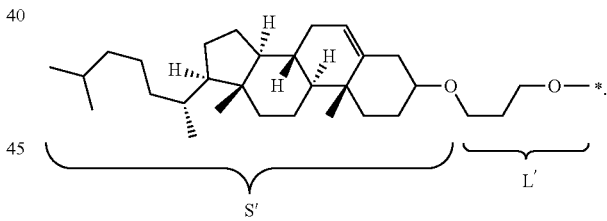

The S'-L'-* fragment derived from Chol-OTEG-OH has the structure:

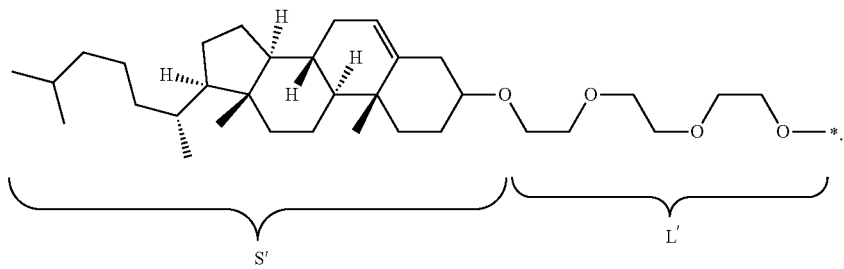

The ROP initiator can be used singularly or in combination with a different ROP initiator (e.g., initiators having different steroid groups and/or different $L^e$ groups.) The ROP initiator can be stereospecific or non-stereospecific.

Di-Nucleophilic Initiators for Two-Armed Cationic Polymers

The ROP initiator used to form the above described cationic polymers having two polymer chains (two-armed cationic polymers) is a di-nucleophilic initiator. Exemplary di-nucleophilic ROP initiators include ethylene glycol, butanediol, 1,4-benzenedimethanol, and Bn-MPA:

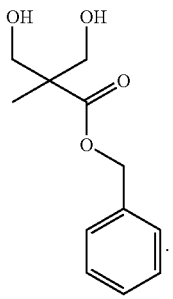 [SMILES: CC(CO)(CO)C(=O)OCc1ccccc1]

An exemplary di-nucleophilic ROP initiator comprising a steroid group is Chol-MPA:

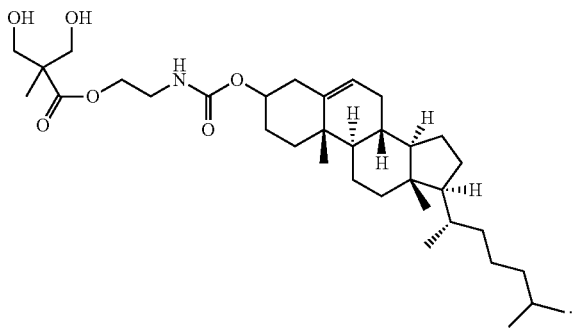

ROP Polymerization

Using a cyclic carbonate monomer of formula (20) to illustrate a method of making the disclosed cationic polymers, a reaction mixture is formed which comprises a cyclic carbonate monomer of formula (20), a catalyst, an optional accelerator, a mono-nucleophilic ROP initiator (optionally comprising a steroid group), and a solvent. Agitating the reaction mixture forms an initial polymer. Optionally the initial polymer can be endcapped to form an endcapped initial polymer. The resulting polymer has a structure according to formula (27):

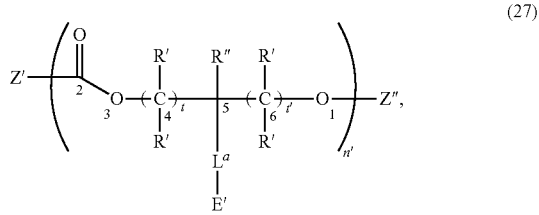

(27)

wherein n' represents the number of cationic carbonate repeat units, wherein n' has a value of about 5 to about 45, Z' is a monovalent $C_1$-$C_{15}$ first end group, Z" is a monovalent second end group selected from the group consisting of hydrogen and $C_1$-$C_{15}$ moieties, $L^a$ is a divalent linking group comprising at least 3 carbons, E' is a substituent capable of reacting to produce a cationic moiety $Q'(R^a)_{u'}$ linked to $L^a$, wherein Q' is a tetravalent positive-charged nitrogen or phosphorus, u' has a value of 1 to 3, each $R^a$ is an independent radical having a valency of 1 to 3, wherein each $R^a$ comprises 1 or more carbons, and together $Q'(R^a)_{u'}$ and $L^a$ comprise 6 to about 25 carbons, each R' is an independent monovalent radical selected from the group consisting of hydrogen, halogens, methyl, and ethyl, each R" is an independent monovalent radical selected from the group consisting of hydrogen, halogens, and alkyl groups comprising 1 to 6 carbons, each t is an independent positive integer having a value of 0 to 2, each t' is an independent positive integer having a value of 0 to 2, and no carbonate repeat unit has t=0 and t'=0.

Z' can be a residue of the ROP initiator. In an embodiment, Z' is an S'-L' group comprising a steroid moiety. In this instance, each carbonate repeat unit of the initial polymer comprises a side chain E' group.

The living end (oxy end) of the initial polymer formed by the ROP has a reactive hydroxy group (second end group Z"=H), which is capable of initiating another ROP. The living end can be treated with an endcap agent, thereby forming a second end group Z" that is capable of preventing further chain growth and stabilizing the polymer against unwanted side reactions such as chain scission. The polymerization and endcapping can occur in the same pot without isolating the initial polymer. Endcap agents include, for example, materials for converting terminal hydroxy groups to esters, such as carboxylic acid anhydrides, carboxylic acid chlorides, and reactive esters (e.g., p-nitrophenyl esters). In an embodiment, the endcap agent is an acylating agent, and the second end group Z" is an acyl group. In another embodiment the acylating agent is acetic anhydride, and the second end group Z" is an acetyl group. In another embodiment, the endcap agent comprises a covalently bound form of a steroid group, a vitamin, or a combination thereof.

The initial polymer and/or the endcapped initial polymer can be treated chemically, thermally, and/or photochemically to convert E' to a positive-charged $Q'(R^a)_{u'}$ group, thereby forming a cationic polymer. For example, E' can be an electrophilic leaving group (e.g., chloride, bromide, iodide, sulfonate ester, and the like), which is capable of undergoing a nucleophilic displacement reaction with a Lewis base (e.g., tertiary amine, trialkyl phosphine) to form a quaternary ammonium group and/or a phosphonium group. In an embodiment, E' is chloride, bromide, and/or iodide. In another embodiment, the cyclic carbonate monomer is a compound of formula (22) and the initial polymer comprises a repeat unit of formula (23). In another embodiment, the cyclic carbonate monomer is a compound of formula (24) and the initial polymer comprises a repeat unit of formula (25).

Also contemplated is a method of forming the cationic polymer using a cationic cyclic carbonate monomer that comprises a positive-charged Q' group. In this instance, the ROP forms an initial cationic polymer having a living end unit (i.e., a nucleophilic hydroxy end group capable of initiating a subsequent ROP). The living end unit can be endcapped to prevent unwanted side reactions.

Exemplary non-limiting tertiary amines for forming quaternary amines by a nucleophilic substitution reaction with electrophilic E' groups include trimethylamine, triethylamine, tri-n-propylamine, tri-iso-propylamine, tri-n-butylamine, tri-n-pentylamine, dimethylethylamine, dimethylpropylamine, dimethyl-iso-propylamine, dimethylbutylamine, dimethylpentylamine, dimethylbenzylamine, diethylmethylamine, diethylpentylamine, diethylbutylamine, N,N-dimethylcyclohexylamine, N-methylimidazole, N-ethylimidazole, N-(n-propyl)imidazole, N-isopropylimidazole, N-(n-butyl)imidazole, N,N-diethylcyclohexylamine, N,N-dimethylaniline, N,N-diethylaniline, pyridine, and combinations thereof.

Exemplary non-limiting tertiary phosphines for forming quaternary phosphonium groups by a nucleophilic substitution reaction with electrophilic E' groups include trimethylphosphine, triethylphosphine, tripropylphosphine, tributylphosphine, ethyldimethylphosphine, propyldimethylphosphine, butyldimethylphosphine, pentyldimethylphosphine, hexyldimethylphosphine, heptyldimethylphosphine, octyldimethylphosphine, methyldiethylphosphine, propyldiethylphosphine, butyldiethylphosphine, pentyldiethylphosphine, hexyldiethylphosphine, heptyldiethylphosphine, octyldiethylphosphine, pentyldipropylphosphine, pentyldibutylphosphine, dipentylmethylphosphine, dipentylethylphosphine, dipentylpropylphosphine, dipentylbutylphosphine, tripentylphosphine, hexyldipropylphosphine, hexyldibutylphosphine, cyclohexyl-dimethylphosphine, cyclohexyldiethylphosphine, dihexylmethylphosphine, dihexyl-ethylphosphine, dihexylpropylphosphine, benzyldimethylphosphine, and combinations thereof.

Exemplary non-limiting cyclic carbonate monomers bearing a covalently bound form of a steroid or vitamin are listed in Table 2.

TABLE 2

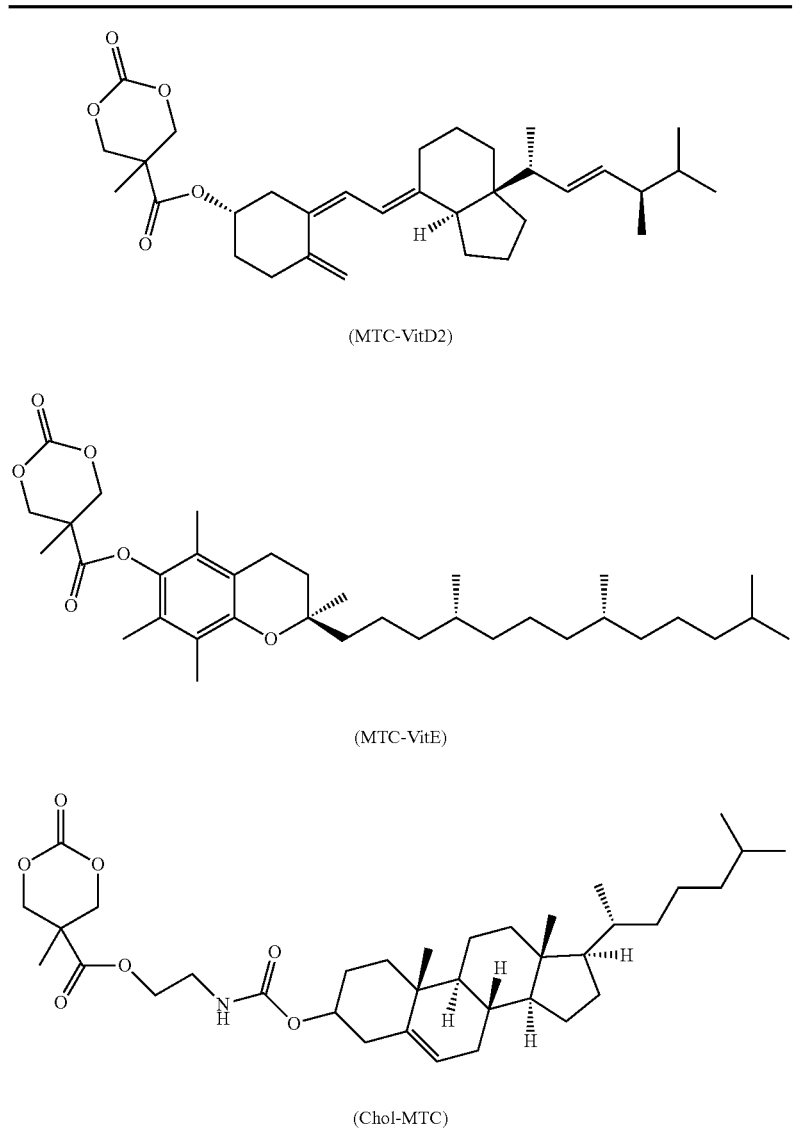

(MTC-VitD2)

(MTC-VitE)

(Chol-MTC)

The ring-opening polymerization can be performed at a temperature that is about ambient temperature or higher, more specifically 15° C. to 200° C., and even more specifically 20° C. to 80° C. Preferably, the ROP is performed at ambient temperature. Reaction times vary with solvent, temperature, agitation rate, pressure, and equipment, but in general the polymerizations are complete within 1 to 100 hours.

The ROP reaction is preferably performed with a solvent. Non-limiting solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. A suitable monomer concentration is about 0.1 to 5 moles per liter, and more particularly about 0.2 to 4 moles per liter.

The ROP polymerization is conducted under an inert dry atmosphere, such as nitrogen or argon, and at a pressure of 100 MPa to 500 MPa (1 atm to 5 atm), more typically at a pressure of 100 MPa to 200 MPa (1 atm to 2 atm). At the completion of the reaction, the solvent can be removed using reduced pressure.

Less preferred catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

Preferably, the chemical formula of the catalyst used for the ring opening polymerization does not include an ionic or nonionic form of a metal selected from the group consisting of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium.

Preferred catalysts are organocatalysts whose chemical formulas contain none of the above metals. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-bis(3,5-trifluoromethyl)phenyl-N'-cyclohexylthiourea (TU):

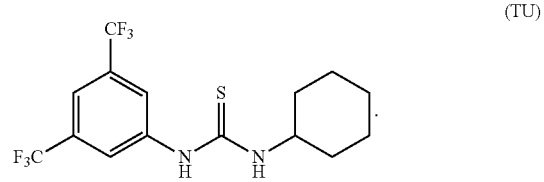 [SMILES: FC(F)(F)c1cc(NC(=S)NC2CCCCC2)cc(C(F)(F)F)c1]

Other ROP organocatalysts comprise at least one 1,1,1,3,3,3-hexafluoropropan-2-ol-2-yl (HFP) group. Singly-donating hydrogen bond catalysts have the formula (28):

$$R^2—C(CF_3)_2OH \qquad (28),$$

wherein $R^2$ represents a hydrogen or a monovalent radical having 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 3.

TABLE 3

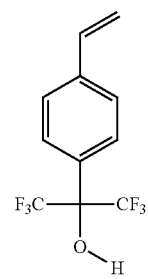 [SMILES: C=Cc1ccc(C(O)(C(F)(F)F)C(F)(F)F)cc1]

4-HFA-St

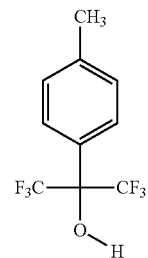

4-HFA-Tol

TABLE 3-continued

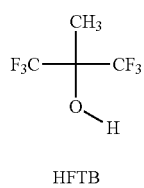

HFTB

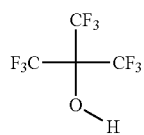

NFTB

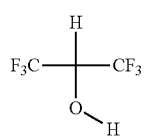

HFIP

Doubly-donating hydrogen bonding catalysts have two HFP groups, represented by the formula (29):

$$HO-\underset{CF_3}{\overset{CF_3}{\underset{|}{C}}}-R^3-\underset{CF_3}{\overset{CF_3}{\underset{|}{C}}}-OH, \quad (29)$$

wherein $R^3$ is a divalent radical bridging group comprising 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (29) include those listed in Table 4. In a specific embodiment, $R^2$ is an arylene or substituted arylene group, and the HFP groups occupy positions meta to each other on the aromatic ring.

TABLE 4

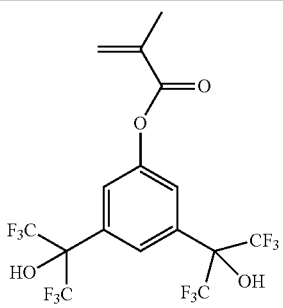 [SMILES: C=C(C)C(=O)Oc1cc(C(O)(C(F)(F)F)C(F)(F)F)cc(C(O)(C(F)(F)F)C(F)(F)F)c1]

3,5-HFA-MA

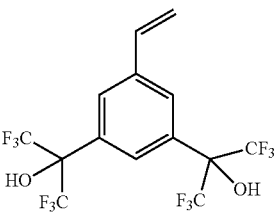 [SMILES: C=Cc1cc(C(O)(C(F)(F)F)C(F)(F)F)cc(C(O)(C(F)(F)F)C(F)(F)F)c1]

3,5-HFA-St

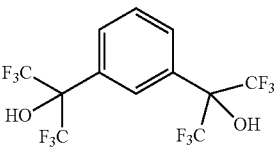

1,3-HFAB

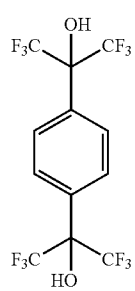

1,4-HFAB

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators.

The ROP polymerization can be conducted in the presence of an optional accelerator, in particular a nitrogen base. Exemplary nitrogen base accelerators are listed below and include pyridine (Py), N,N-dimethylaminocyclohexane (Me₂NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1, 5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-i-propylphenyl)imidazol-2-ylidene (Im-3), 1,3-bis(1-adamantyl)imidazol-2-ylidene (Im-4), 1,3-di-i-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-i-propylphenyl)-4,5-dihydroimidazol-2-ylidene, 1,3-bis(2,6-di-i-propylphenyl)-4,5-dihydroimidazol-2-ylidene (Im-8) or a combination thereof, shown in Table 5.

TABLE 5

Pyridine
(Py)

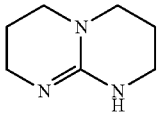

N,N-Dimethylaminocyclohexane
(Me₂NCy)

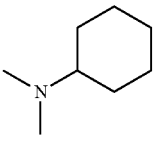

4-N,N-Dimethylaminopyridine
(DMAP)

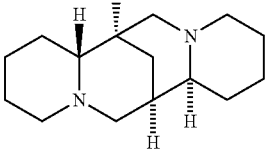

trans 1,2-Bis(dimethylamino)cyclohexane
(TMCHD)

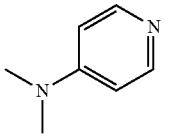

1,8-Diazabicyclo[5.4.0]undec-7-ene
(DBU)

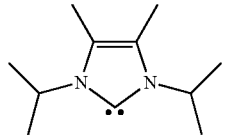

7-Methyl-1,5,7-triazabicyclo[4.4.0]dec-5-ene
(MTBD)

TABLE 5-continued

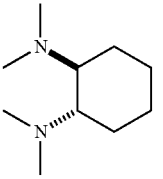

1,5,7-Triazabicyclo[4.4.0]dec-5-ene
(TBD)

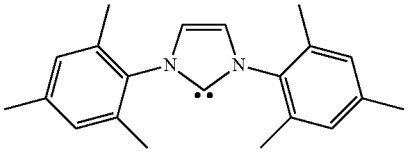

(−)-Sparteine
(Sp)

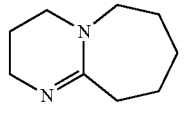 [SMILES: C1CCC2=NCCCN2CC1]

1,3-Bis(2-propyl)-4,5-dimethylimidazol-2-ylidene
(Im-1)

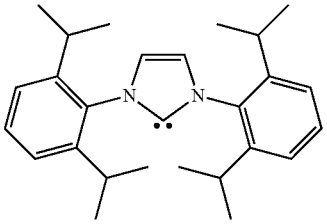

1,3-Bis(2,4,6-trimethylphenyl)imidazol-2-ylidene
(Im-2)

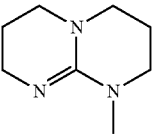

1,3-Bis(2,6-di-i-propylphenyl)imidazol-2-ylidene
(Im-3)

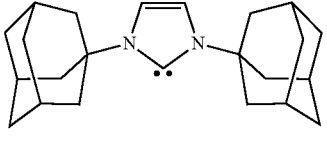

1,3-Bis(1-adamantyl)imidazol-2-yliden)
(Im-4)

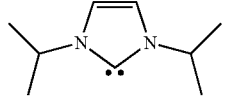

1,3-Di-i-propylimidazol-2-ylidene
(Im-5)

TABLE 5-continued

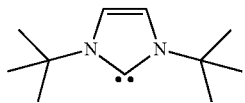

1,3-Di-t-butylimidazol-2-ylidene
(Im-6)

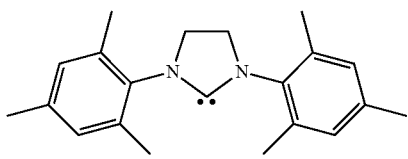

1,3-Bis(2,4,6-trimethylphenyl)-4,5-
dihydroimidazol-2-ylidene
(Im-7)

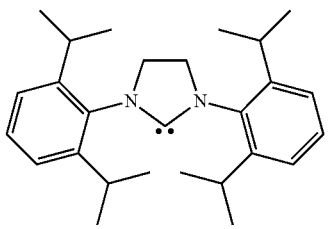

1,3-Bis(2,6-di-i-propylphenyl)-4,5-
dihydroimidazol-2-ylidene
(Im-8)

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The initiator groups are preferably present in an amount of 0.001 to 10.0 mol %, 0.1 to 2.5 mol %, 0.1 to 1.0 mol %, or 0.2 to 0.5 mol %, based on total moles of cyclic carbonyl monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on total moles of cyclic carbonate monomer.

The catalysts can be removed by selective precipitation or, in the case of the solid supported catalysts, by filtration. The catalyst can be present in an amount of 0 wt % (weight percent) to about 20 wt %, preferably 0 wt % (weight percent) to about 0.5 wt % based on the total weight of the cationic polymer and the residual catalyst. The cationic polymer preferably comprises no residual catalyst.

Average Molecular Weight.

The cationic polymers have a number average molecular weight (Mn) as determined by size exclusion chromatography of about 1500 to about 50,000, more specifically about 1500 to about 30,000. The precursor polymer to the cationic polymer and/or the cationic polymer preferably has a polydispersity index (PDI) of 1.01 to about 1.5, more particularly 1.01 to 1.30, and even more particularly 1.01 to 1.25.

In some instances the cationic polymers can self-assemble into nanoparticulate micelles in de-ionized water. The cationic polymers can have a critical micelle concentration (CMC) of about 15 mg/L to about 45 mg/L.

The micelles can have a minimum inhibitory concentration (MIC) for microbial growth of about 7 mg/L to about 500 mg/L. In some instances, the MIC is below the CMC, meaning the antimicrobial activity is not dependent on self-assembly of the cationic polymers.

Further disclosed is a method of treating a microbe, comprising contacting a microbe with a disclosed cationic polymer, thereby killing the microbe.

For the examples below, the following definitions are applicable.

HC50 is defined as the concentration (in mg/L) of cationic polymer that causes 50% of mammalian red blood cells to undergo hemolysis. HC50 values of 500 mg/L or higher are desirable.

HC20 is defined as the concentration (in mg/L) of cationic polymer that causes 20% of mammalian red blood cells to undergo hemolysis. HC20 values of 500 mg/L or higher are desirable.

Minimum inhibitory concentration (MIC) is defined as the minimum concentration (in mg/L) of cationic polymer required to inhibit growth of a given microbe for a twenty-four period. An MIC less than 500 mg/L is desirable. Even more desirable is a MIC of 250 mg/L or less. A lower MIC indicates higher antimicrobial activity.

Minimum bactericidal concentration (MBC) is defined as the minimum concentration (in mg/L) of cationic polymer required to kill a given microbe. A lower MBC indicates higher antimicrobial activity.

HC50 selectivity is defined as the ratio of HC50/MIC. An HC50 selectivity of 3 or more is desirable. Higher HC50 selectivity values indicate more activity against microbial cells and less toxicity to mammalian cells. Likewise, HC20 selectivity is defined as the ratio of HC20/MIC. An HC20 selectivity of 3 or more is desirable.

Non-limiting microbes, which were used in the examples below, include Gram-positive *Staphylococcus epidermidis* (*S. epidermidis*), Gram-positive *Staphylococcus aureus* (*S. aureus*), Gram-negative *Escherichia coli* (*E. coli*), Gram-negative *Pseudomonas aeruginosa* (*P. aeruginosa*), Gram-positive fungus *Candida albicans* (*C. albicans*), Gram-positive Methicillin-resistant *Staphylococcus aureus* (MRSA), Gram-positive Vancomycin-resistant *Enterococcus* (VRE), Gram-negative *Acinetobacter baumannii* (*A. baumannii*), Gram-positive yeast *Cryptococcus neoformans* (*C. neoformans*), and Gram-negative *Klebsiella pneumoniae* (*K. pneumoniae*).

In general, cationic polymers having a DP of 5 to about 45 in which greater than 75% of the side chain $L^a$-$Q'(R^a)_{u'}$ groups of the cationic carbonate repeat units contained 8 carbons or less were weakly active against Gram-negative and/or Gram-positive microbes and fungi. Moreover, at low DP (<10) the HC50 and/or HC20 values of the cationic polymers generally fell below 500 mg/L, indicating a trend toward biocidal properties. Higher HC50 and/or HC20 values (500 mg/L or higher) were generally favored by a DP of about 10 to about 45. The examples further below also show that when at least 25% of the side chain groups of the cationic carbonate repeat units contained 13 or more carbons and the DP was about 10 to about 30, the cationic polymers were highly active (MIC<500 mg/L) against both Gram-negative and Gram-positive microbes and fungi, and had HC50 values of 500 mg/L or higher. Increased inhibition efficacy and lower red blood cell toxicity (higher HC50 values) were obtained using a steroid end group Z'. Hemolytic selectivity (HC50/MIC) also rose. The groups Z', Z", $Z^c$, and C' can be used to further adjust antimicrobial activity, hemolytic selectivity, or to provide a secondary function (e.g., cell recognition capability, enhancement of cell membrane permeability, and so on).

The examples also show that 10 mol % or less of carbonate repeat units comprising an alpha-tocopheryl (a vitamin E compound) and/or an ergocalciferyl (vitamin D2) side chain moiety was also effective in lowering MIC (i.e., increasing toxicity to microbes) and/or increasing HC50 values (lowering toxicity to mammalian red blood cells) when 25% to 100% of the cationic carbonate repeat units comprised 10 to 25 carbons.

In some cases, cell viability of human fibroblast cells incubated with the cationic polymers was more than 75%.

The low average mass, high antimicrobial activity, and low cytotoxicity makes these cationic polymers highly attractive for a wide range of medical and household uses, including wound treatments, treatment of infections, antibiotic drugs, and disinfectants for household and hospital surfaces and medical instruments. In an embodiment, a medical composition for killing a microbe comprises one or more of the disclosed cationic polymers. The medical composition can be in the form of a solution, powder, pill, paste, or ointment. The medical composition can comprise water, wherein the concentration of the cationic polymer is below the critical micelle concentration of the cationic polymer. The medical composition can be injected and/or applied topically.

The following examples demonstrate the preparation and properties of the cationic polymers.

EXAMPLES

Materials used in the following examples are listed in Table 6.

TABLE 6

| ABBREVIATION | DESCRIPTION | SUPPLIER |
| --- | --- | --- |
| DBU | 1,8-Diazabicyclo[5,4,0]undec-7-ene | Sigma-Aldrich |
|  | p-Chloromethyl Benzyl Alcohol | Sigma-Aldrich |
| PROTON SPONGE | 1,8-Bis(dimethylamino)naphthalene; trademark of Sigma Aldrich | Sigma-Aldrich |
|  | Cholesterol | Sigma-Aldrich |
|  | 1,3-Propanediol | Sigma-Aldrich |
| MesCl | Mesyl chloride | Sigma-Aldrich |
| DCM | Dichloromethane | Sigma-Aldrich |
| TMA | Trimethylamine | Sigma-Aldrich |
| TMP | Trimethylphosphine | Sigma-Aldrich |
| TU | N-Bis-(3,5-Trifluoromethyl)Phenyl-N'-Cyclohexylthiourea | Prepared below |
| PFC | Bis-(Pentafluorophenyl) Carbonate | Sigma-Aldrich |
| MTT | 1-(4,5-Dimethylthiazol-2-yl)-3,5-Diphenylformazan | Sigma-Aldrich |

TABLE 6-continued

| ABBREVIATION | DESCRIPTION | SUPPLIER |
| --- | --- | --- |
| DMEM | Dulbecco's Modified Eagle Medium | Invitrogen |
| BnOH | Benzyl Alcohol, initiator for ROP | Sigma-Aldrich |
| 4-MeBnOH | 4-Methyl Benzyl Alcohol, initiator for ROP | Sigma-Aldrich |
| Chol-OH | Cholesterol | Sigma Aldrich |
| MeIm | Methyl Imidazole | Sigma-Aldrich |
| EtIm | Ethyl Imidazole | Sigma-Aldrich |
| TMA | Trimethyl Amine | Sigma-Aldrich |
|  | Ergocalciferol (Vitamin D2) | TCI |
|  | alpha-Tocopherol (one of the Vitamin E family) | Alfa Aesar |
|  | Dimethyl Butyl Amine | Sigma-Aldrich |
|  | Dimethyl Hexyl Amine | Sigma-Aldrich |
|  | Dimethyl Ethyl Amine | Sigma-Aldrich |
|  | Dimethyl Benzyl Amine | Sigma-Aldrich |
|  | Dimethyl Octyl Amine | TCI |
|  | Butyl Imidazole | Sigma-Aldrich |
|  | Dimethyl Cyclohexyl Amine | Sigma-Aldrich |

Herein, Mn is the number average molecular weight, Mw is the weight average molecular weight, and MW is the molecular weight of one molecule.

Unless specifically mentioned, all materials were purchased from Sigma-Aldrich, TCI or Merck. All solvents were of analytical grade, purchased from Fisher Scientific or J. T. Baker and used as received. Before transferring into the glove box, monomers and other reagents (e.g., initiator, monomer, etc.) were dried extensively by freeze-drying under high vacuum.

N-bis(3,5-trifluoromethyl)phenyl-N'-cyclohexylthiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over $CaH_2$, filtering, and removing solvent under vacuum.

1,8-Diazabicyclo[5,4,0]undec-7-ene (DBU) was stirred over $CaH_2$ and vacuum distilled before being transferred to a glove box.

Critical Micelle Concentration (CMC) Measurements.

The respective critical micelle concentrations (CMC) of the cationic polymers were estimated by fluorescence spectroscopy using pyrene as a probe. A series of polymer solutions containing 0.616 micromoles of pyrene was prepared at various concentrations (0.25-2000 mg/L) in MHB II containing 10% v/v water. Following an overnight incubation, excitation spectra of the solutions were recorded from 325 to 360 nm at room temperature, with an emission wavelength of 390 nm and bandwidth of 1 nm using a spectrofluorometer (Hitachi F-2500). The intensity ratios of $I_{339}$ to $I_{335}$ were plotted as a function of polymer concentration. The CMC value was taken from the intersection of the tangent to the curve at the inflection with the horizontal tangent of the points at low concentrations.

I. Monomer Synthesis

Preparation of MTC-OH (MW 160.1)

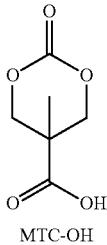

MTC-OH

MTC-OH can be prepared by the method of R. C. Pratt, et al., Chemical Communications, 2008, 114-116.

Preparation of MTC-C6H5 (MW 326.2)

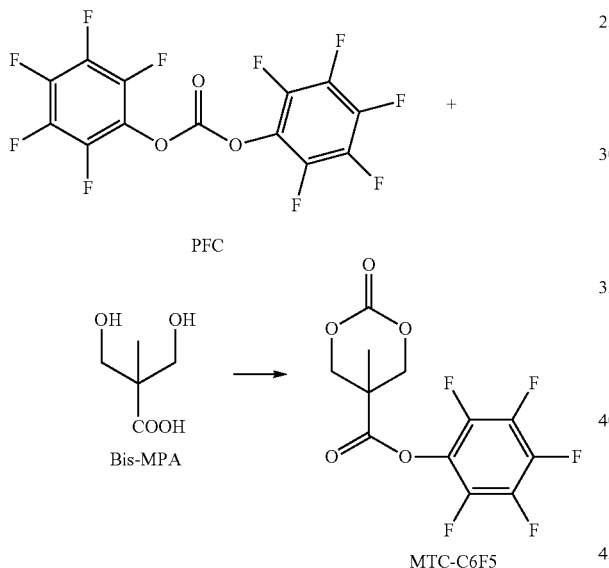

A 100 mL round bottom flask was charged with bis-MPA (5.00 g, 37 mmol, MW 134.1), bis-(pentafluorophenyl) carbonate (PFC, 31.00 g, 78 mmol, MW 394.1), and CsF (2.5 g, 16.4 mmol) rinsed with 70 mls of tetrahydrofuran (THF). Initially the reaction was heterogeneous, but after one hour a clear homogeneous solution was formed that was allowed to stir for 20 hours. The solvent was removed in vacuo and the residue was re-dissolved in methylene chloride. The solution was allowed to stand for approximately 10 minutes, at which time the pentafluorophenol byproduct precipitated and could be quantitatively recovered. This pentafluorophenol byproduct showed the characteristic 3 peaks in the $^{19}F$ NMR of pentafluorophenol and a single peak in the GCMS with a mass of 184. The filtrate was extracted with sodium bicarbonate, water and was dried with $MgSO_4$. The solvent was evaporated in vacuo and the product was recrystallized (ethyl acetate/hexane mixture) to give MTC-C6F5 as a white crystalline powder. The GCMS had a single peak with mass of 326 g/mol. The calculated molecular weight for $C_{12}H_7F_5O_5$ was consistent with the assigned structure. $^1$H-NMR (400 MHz in $CDCl_3$): delta 4.85 (d, J=10.8 Hz, 2H, $CH_aH_b$), 4.85 (d, J=10.8 Hz, 2H, $CH_aH_b$), 1.55 (s, 3H, $CCH_3$).

Preparation of MTC-BnCl (MW 298.7)

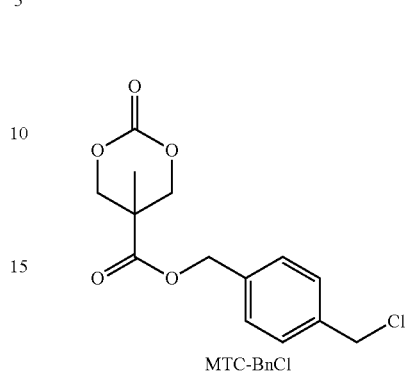

MTC-BnCl

A flask was charged with MTC-C6F5 (10 g, 30.6 mmol), p-chloromethyl benzyl alcohol (4.8 g, 30.6 mmol), PROTON SPONGE (2 g, 9.3 mmol) and THF (30 mL). The reaction mixture was stirred for 12 hours then added directly to a silica gel column. The product was isolated using diethyl ether as the eluent to yield 7.45 g (81%) white crystalline powder. $^1$H NMR (400 MHz, $CDCl_3$, 22° C.): delta 7.40 (dd, 4H, $C_6H_4$), 5.24 (s, 2H, $-OCH_2C_6H_4$), 4.73 (d, 2H, $-CH_2OCOO$), 4.60 (s, 2H, $-CH_2Cl$), 4.22 (d, 2H, $-CH_2OCOO$), 1.35 (s, 3H, $-CH_3$).

Preparation of MTC-PrCl (MW 236.65)

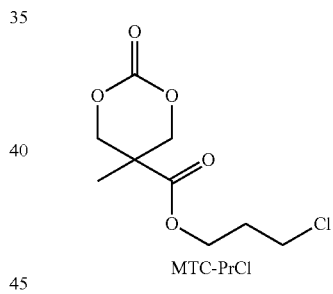

MTC-PrCl

MTCOH (8.82 g, 55 mmol) was converted to MTCOCl using standard procedures with oxalyl chloride. In a dry 250 mL round bottom flask equipped with a stir bar, the formed intermediate was dissolved in 150 mL of dry methylene chloride. Under nitrogen flow an addition funnel was attached to which 3-chloropropanol (4.94 g, 4.36 mL, 52.25 mmol), pyridine (3.95 g, 4.04 mL, 55 mmol), and dry methylene chloride (50 mL) were combined. The flask was cooled to 0° C. using an ice bath and the top solution was added drop-wise during a period of 30 minutes. The formed solution was stirred for an additional −30 minutes before the ice bath was removed and the solution was stirred for an additional 16 hours under nitrogen. The crude product MTC-PrCl was directly applied onto a silica gel column and the product was separated by eluting with 100% methylene chloride. The product fractions were removed and the solvent was evaporated, yielding the product as off-white oil, which crystallized upon standing. Yield 11 g (85%). $^1$H-NMR ($CDCl_3$) delta: 4.63 (d, 2H, $CH_2$), 4.32 (t, 2H, $CH_2$), 4.16 (d, 2H, $CH_2$), 3.55 (t, 2H, $CH_2$), 2.09 (m, 2H, $CH_2$), 1.25 (s, 3H, $CH_3$).

Preparation of 5-methyl-5-(3-bromopropyl)oxycarbonyl-1,3-dioxan-2-one, (MTC-PrBr), (MW 281.10)

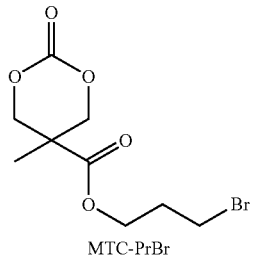

MTC-PrBr

MTCOPrBr was prepared by the procedure for MTCO-PrCl on a 45 mmol scale using 3-bromo-1-propanol as the alcohol. The product was purified by column chromatography, and subsequently recrystallized to yield white crystals (6.3 g, 49%). $^1$H NMR (400 MHz, CDCl$_3$): delta 4.69 (d, 2H; CH$_2$OCOO), 4.37 (t, 2H; OCH$_2$), 4.21 (d, 2H; CH$_2$OCOO), 3.45 (t, 2H; CH$_2$Br), 2.23 (m, 2H; CH$_2$), 1.33 (s, 3H; CH$_3$). $^{13}$C NMR (100 MHz, CDCl$_3$): delta 171.0, 147.3, 72.9, 63.9, 40.2, 31.0, 28.9, 17.3.

Preparation of MTC-C6Cl (MW 278.09)

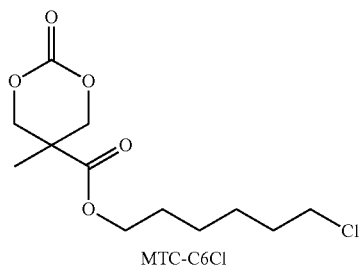 [SMILES: CC1(C(=O)OCCCCCCCl)COC(=O)OC1]

MTC-C6Cl

A flask was charged with MTC-C6F5 (6.6 g, 20.1 mmol), 6-chloro-1-hexanol (2.5 g, 18.3 mmol), PROTON SPONGE (3.9 g, 18.3 mmol) and tetrahydrofuran (THF) (8 mL). The reaction mixture was stirred for 12 hr and excess ammonium acetate was added. The reaction mixture was stirred for 3 additional hours and then added directly to a silica gel column. The product was isolated using hexane/ethyl acetate as the eluent to yield an oil (4.2 g, 57%). $^1$H NMR (400 MHz, CDCl$_3$, 22° C.): delta 4.72 (d, 2H, —CH$_2$OCOO), 4.23 (d, t 4H, —CH$_2$OCOO, —OCH$_2$CH$_2$), 3.57 (t, 2H, —OCH$_2$CH$_2$CH$_2$CH$_2$CH$_2$CH$_2$Cl), 1.84 (m, 2H, —OCH$_2$CH$_2$CH$_2$CH$_2$CH$_2$CH$_2$Cl), 1.76 (m, 2H, —OCH$_2$CH$_2$CH$_2$CH$_2$CH$_2$CH$_2$Cl), 1.45 (m, 2H, —OCH$_2$CH$_2$CH$_2$CH$_2$CH$_2$CH$_2$Cl), 1.39 (m, 2H, —OCH$_2$CH$_2$CH$_2$CH$_2$CH$_2$CH$_2$Cl), 1.35 (s, 3H, —CH$_3$).

Preparation of MTC-C8Cl (MW 306.12)

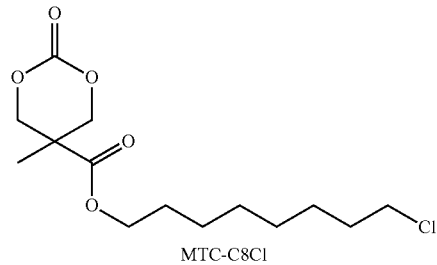 [SMILES: CC1(C(=O)OCCCCCCCCCl)COC(=O)OC1]

MTC-C8Cl

A flask was charged with MTC-C6F5 (6.6 g, 20.1 mmol), 6-chloro-1-octanol (2.5 g, 18.3 mmol), PROTON SPONGE (3.9 g, 18.3 mmol) and THF (8 mL). The reaction mixture was stirred for 12 hours and excess ammonium acetate was added. The reaction mixture was stirred for 3 additional hours and then added directly to a silica gel column. The product was isolated using hexane/ethyl acetate as the eluent to yield an oil (4.2 g, 57%). $^1$H NMR (400 MHz, CDCl$_3$, 22° C.): delta 4.72 (d, 2H, —CH$_2$OCOO), 4.23 (d, t 4H, —CH$_2$OCOO, —OCH$_2$CH$_2$), 3.57 (t, 2H, —OCH$_2$CH$_2$(CH$_2$)$_3$CH$_2$CH$_2$CH$_2$Cl), 1.84 (m, 2H, —OCH$_2$CH$_2$(CH$_2$)$_3$CH$_2$CH$_2$CH$_2$Cl), 1.76 (m, 2H, —OCH$_2$CH$_2$(CH$_2$)$_3$CH$_2$CH$_2$CH$_2$Cl), 1.45 (m, 2H, —OCH$_2$CH$_2$(CH$_2$)$_3$CH$_2$CH$_2$CH$_2$Cl), 1.35 (br, 9H, —CH$_3$, OCH$_2$CH$_2$(CH$_2$)$_3$CH$_2$CH$_2$CH$_2$Cl).

Preparation of Chol-MTC

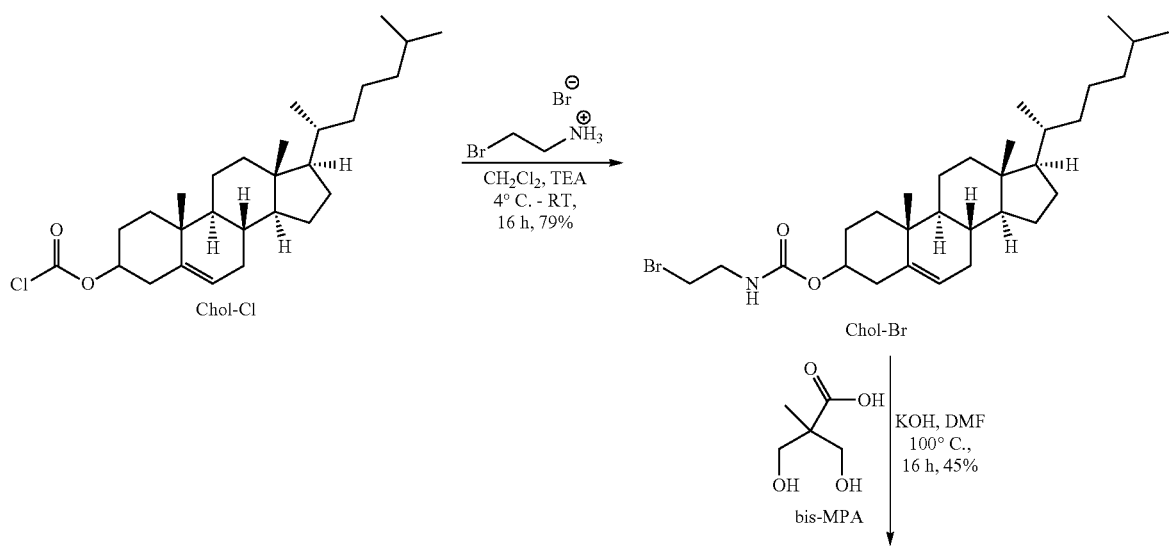

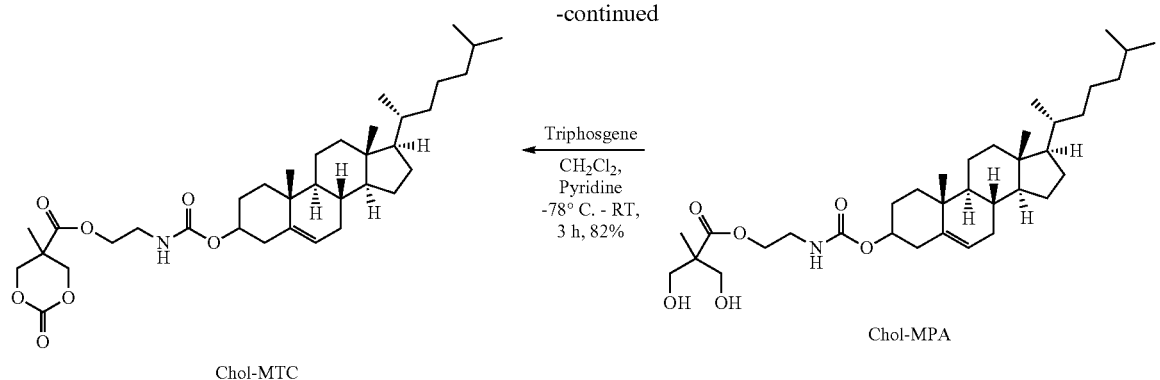

Chol-MTC                Chol-MPA

T

The preparation involves three steps: 1) reaction of the cholesteryl chloroformate Chol-Cl with 2-bromoethyl amine hydrobromide in dichloromethane with triethylamine (TEA) to form carbamate Chol-Br; 2) base-catalyzed reaction of Chol-Br with the acid diol bis-MPA in dimethylformamide (DMF)/KOH to form the diol ester Chol-MPA, and 3) triphosgene-mediated cyclization of Chol-MPa to form the cyclic carbonate monomer Chol-MTC, with overall yield of about 26%. Detailed procedures of each of the three steps are provided below. $^1$H and $^{13}$C NMR were used to confirm the structures of the intermediates and the cyclic carbonate monomer.

1) Preparation of Chol-Br. In a 500 mL round bottom flask, equipped with a magnetic stir bar, cholesterol chloroformate (25.0 g, 55.7 mmol, 1.0 equiv.) and 2-bromoethyl-amine hydrobromide (12.9 g, 63.0 mmol, 1.1 equiv.) were suspended in dichloromethane (200 mL) and the suspension was chilled in an ice-bath. To this suspension, a solution of triethylamine (TEA) (18.0 mL, 13.06 g, 129.1 mmol, 2.3 equiv.) in dichloromethane (100 mL) was added dropwise over 1 hour. The reaction mixture was maintained in the bath for an additional hour and was allowed to warm to room temperature. The reaction was then allowed to proceed for another 14 h, after which dichloromethane was removed under vacuo and the resultant solids were suspended in a 1:1 mixture of ethyl acetate and hexanes (300 mL). Organic layer was washed 2 times with a mixture of saturated brine (100 mL) and de-ionized water (50 mL), and one time with saturated brine (100 mL). The organic layer was dried over sodium sulfate and the solvents were removed under vacuo to yield a pale yellow solid (29.1 g, 97.4%). As the crude product was determined to have satisfactory purity by $^1$H NMR, no further purification was conducted. $^1$H NMR (400 MHz, CDCl$_3$, delta, ppm): 5.38 (CH=C in cholesterol), 5.03 (NHCOO of side-chain), 4.50 (CH—OCONH of cholesterol), 3.58 (BrCH$_2$CH$_2$NH), 2.45-0.6 (rest of the protons from cholesterol).

2) Synthesis of Chol-MPA. In a 500 mL round bottom flask with magnetic stir bar, a mixture of KOH (85%, 2.0 g, 30.3 mmol, 1.1 equiv.), bis-MPA (4.20 g, 31.3 mmol, 1.1 equiv.) and dimethylformamide (DMF) (200 mL) were heated to 100° C. for 1.5 hours. A homogenous solution was formed, and Chol-Br (15.0 g, 28.0 mmol, 1.0 equiv.) was added to the hot solution. Stirring was continued with heating for 16 hours and most of the DMF was removed under reduced pressure, to result in oily semisolid, which was then dissolved in 2:1 ethyl acetate:hexanes mixture (300 mL). The organic solution was washed with saturated brine (100 mL) and de-ionized water (100 mL) mixture. The resultant aqueous layer was extracted with ethyl acetate (3×100 mL) to recover Chol-MPA lost during the washing process. The combined organic layers were washed with saturated brine (80 mL) and de-ionized water (20 mL) mixture. The combined organic layer was dried with Na$_2$SO$_4$ and the solvent removed in vacuo to result in crude product as a pale white waxy solid (16.5 g). The crude product was purified by flash column chromatography using silica as the packing material and a gradient of hexanes to ethyl acetate as the eluent to result in the final product Chol-MPA as a waxy white solid (10.7 g, 64.8%). $^1$H NMR (400 MHz, CDCl$_3$, delta, ppm): 5.35 (CH=C in cholesterol and NHCOO of side-chain), 4.47 (CH—OCONH of cholesterol), 4.26 (CH$_2$CH$_2$NHCOO), 3.88 and 3.72 (CH$_2$OH) 3.45 (CH$_2$CH$_2$NHCOO), 3.34 (OH), 2.50-0.60 (rest of the protons from cholesterol and CH$_3$ from bis-MPA).

3) Preparation of Chol-MTC. In a 500 mL round bottom flask with magnetic stir bar, Chol-MPA (10.1 g, 17.1 mmol, 1.0 equiv.) was dissolved in anhydrous dichloromethane (150 mL). Pyridine (8.2 mL, 8.0 g, 101.5 mmol, 5.9 equiv.) was added and the solution was cooled in a dry ice-acetone bath (−78° C.). To this cooled reaction mixture, triphosgene (2.69 g, 9.06 mmol, 1.9 equivalents based on functional equivalents of triphosgene) solution (dissolved in 50 mL dichloromethane) was added dropwise over 1 hour. After 1 hour, from −78° C., the reaction mixture was allowed to warm up to room temperature, and after 2 hours, the reaction was quenched by adding saturated aqueous ammonium chloride solution (50 mL). The organic layer was washed twice with a mixture of 1.0 N HCl (20 mL) and saturated brine (80 mL), followed by a mixture of saturated brine (50 mL) and saturated NaHCO$_3$ (50 mL), dried using Na$_2$SO$_4$. Removal of solvent in vacuo resulted in crude product as a slightly yellowish solid. The crude product was further purified by flash column chromatography using silica as the packing material and a gradient of chloroform to chloroform:ethyl acetate (4:1) mixtures as the eluent, to result in the final product Chol-MTC as a waxy white solid (6.8 g, 65%). $^1$H NMR (400 MHz, CDCl$_3$, delta, ppm): 5.35 (CH=C in cholesterol), 4.95 (NHCOO), 4.86 and 4.27 (CH$_2$OCOOCH$_2$), 4.47 (CH—OCONH of cholesterol), 4.27 (CH$_2$CH$_2$NHCOO), 3.45 (CH$_2$CH$_2$NHCOO), 2.40-0.60 (rest of the protons from cholesterol and CH$_3$ in the cyclic carbonate monomer).

Preparation of MTC-VitD2

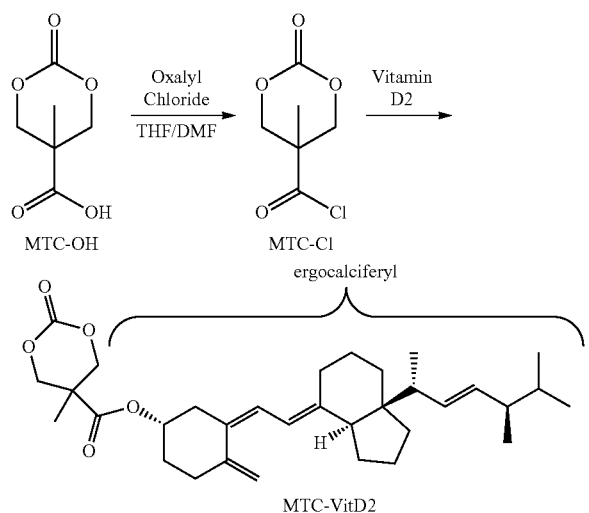

MTC-OH (3.08 g, 19.3 mmol) was dissolved in anhydrous THF (50 mL) with a few drops of DMF. Oxalyl chloride (3.3 mL, 39.4 mmol) was then added dropwise and the reaction mixture stirred under a flow of nitrogen for 1 hour before volatiles were removed under vacuum. The resultant off-white solid was heated to 65° C. for 2 to 3 min to remove any residual reagent and solvent, leaving the acyl chloride intermediate, MTC-Cl. The solid was redissolved in dry dichloromethane (50 mL) and chilled to 0° C. using an ice bath. A solution of ergocalciferol (Vitamin D2) (7.65 g, 19.3 mmol) and dry triethylamine (3 mL, 21.6 mmol) in dry dichloromethane (50 mL) was subsequently added dropwise over 30 min. The mixture was allowed to warm up to ambient temperature and stirred for an additional 18 hours. A crude solid was obtained after removal of solvent, and was subjected to purification by column chromatography using silica gel. Dichloromethane was initially used as the eluent before gently increasing the polarity to finally end with 5% ethyl acetate. The resultant solid was washed with MeOH in order to obtain the desired product in high purity as a white solid (5.20 g, 50%). $^1$H NMR (400 MHz, CDCl$_3$): delta 6.20 (d, 1H, J=11.2 Hz, VitD2-C=CH$_2$), 6.01 (d, 1H, J=11.2 Hz, VitD2-C=CH$_2$), 5.21 (t, 2H, J=6.0 Hz, VitD2-C=CH), 5.08 (overlapping peaks, broad s, 2H, VitD2-C=CH, CH(O-MTC)), 4.86 (s, 1H, VitD2-C=CH), 4.66 (d, 2H, J=12.4 Hz, MTC-CH$_2$), 4.17 (d, 2H, J=12.8 Hz, MTC-CH$_2$), 1.20-2.90 (overlapping peaks, 24H, VitD2), 1.02 (d, 3H, J=6.4 Hz, VitD2-CH$_3$), 0.91 (d, 3H, J=6.8 Hz, VitD2-CH$_3$), 0.84 (t, 6H, J=6.4 Hz, VitD2-CH$_3$), 0.55 (s, 3H, MTC-CH$_3$).

Preparation of MTC-VitE Monomer

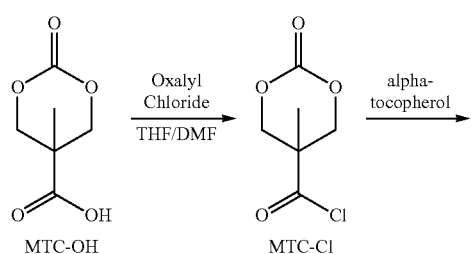

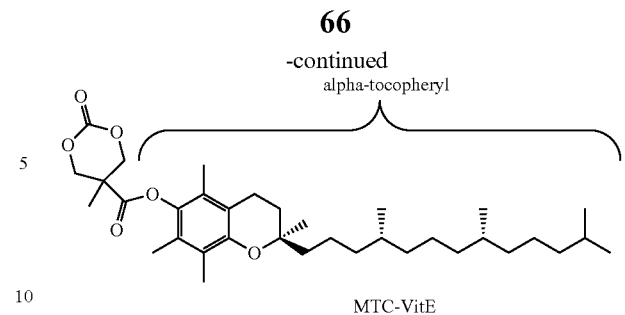

MTC-OH (3.08 g, 19.3 mmol) was dissolved in anhydrous THF (50 mL) with a few drops of DMF. Oxalyl chloride (3.3 mL, 39.4 mmol) was then added dropwise and the reaction mixture stirred under a flow of nitrogen for 1 h before volatiles were removed under vacuum. The resultant off-white solid was heated to 65° C. for 2 to 3 minutes to remove any residual reagent and solvent, leaving acyl chloride intermediate, MTC-Cl. The solid was redissolved in dry dichloromethane (50 mL) and chilled to 0° C. using an ice bath. A solution of alpha-tocopherol (8.30 g, 19.3 mmol) and dry triethylamine (3 mL, 21.6 mmol) in dry dichloromethane (50 mL) was subsequently added dropwise over 30 min. The mixture was allowed to warm up to ambient temperature and stirred for an additional 18 hours. A crude solid was obtained after removal of solvent, and was subjected to purification by column chromatography using silica gel. Hexane was initially used as the eluent before gently increasing the polarity to finally end with 50% ethyl acetate. A second chromatography separation was carried out using dichloromethane/ethyl acetate (4:1) in order to obtain the desired product in high purity as a white solid (6.05 g, 53%). $^1$H NMR (400 MHz, CDCl$_3$): delta 4.92 (d, 2H, J=10.8 Hz, MTC-CH$_2$), 4.34 (d, 2H, J=10.8 Hz, MTC-CH$_2$), 2.59 (d, 2H, J=6.7 Hz, tetrahydropyrano-CH$_2$), 2.09 (s, 3H, Ar—CH$_3$), 2.00 (s, 3H, Ar—CH$_3$), 1.96 (s, 3H, Ar—CH$_3$), 1.70-1.90 (m, 2H), 1.00-1.60 (overlapping peaks, 27H), 0.80-0.90 (m, 12H, 4×CH$_3$ on hydrophobic tail).

II. Initiator Synthesis

Preparation of Bn-MPA, a Diol Initiator

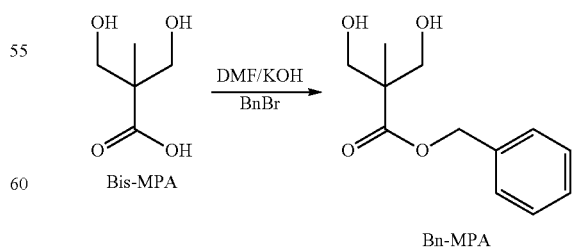

2,2-Bis(methylol)propionic acid (Bis-MPA), KOH, DMF, and benzylbromide (BnBr) were heated together at 100° C. for 15 hours to form the benzyl ester Bn-MPA in 62% yield.

Preparation of Chol-OMes Intermediate (MW 464.7)

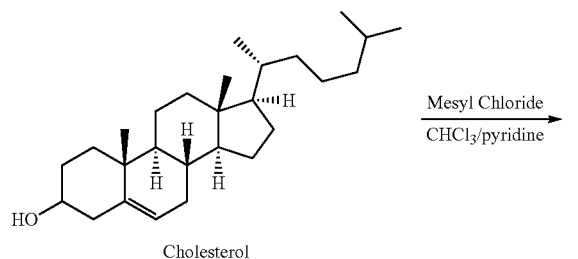

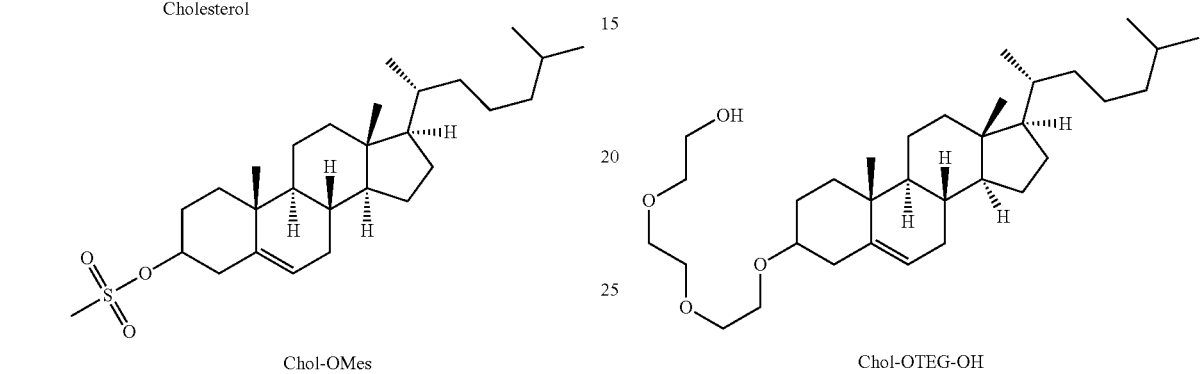

Cholesterol (10 g, 25.8 mmol, MW 386.35) was dissolved in dry chloroform (CHCl$_3$) (15 mL) and pyridine (15 mL). The reaction mixture was then purged with nitrogen and rapidly stirred. Mesyl chloride (3 mL, 38.8 mmol) was then added drop wise. The reaction mixture was stirred for 4 hours at ambient temperature followed by precipitation into MeOH (600 mL). The filtrate was collected via vacuum filtration to yield 9.6 g (80%) white powder.

Preparation of Chol-OPrOH (MW 444.7)

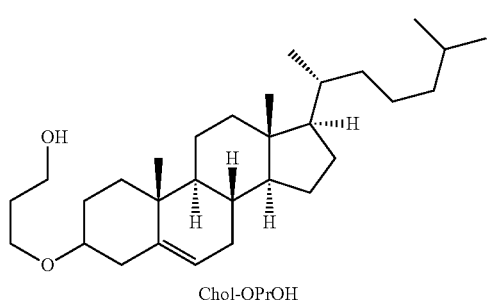

Chol-OMes (1 g, 2.15 mmol) was suspended in 1,4-dioxane (10 mL) and 1,3-propanediol (4 g, 53.8 mmol). The reaction mixture was degassed, purged with nitrogen and heated to 110° C. After 1 hour the reaction mixture was allowed to cool to ambient temperature and precipitated into MeOH/H$_2$O (4:1). The product was further purified using column chromatography producing 0.72 g (75%) of a waxy off-white material.

Preparation of Chol-OTEG-OH (MW 518.8)

Chol-OMes (1 g, 2.15 mmol) was suspended in 1,4-dioxane (10 mL) and triethylene glycol (8 g, 53.8 mmol). The reaction mixture was degassed, purged with nitrogen and heated to 110° C. After 1 hour the reaction mixture was allowed to cool to ambient temperature and precipitated into MeOH/H$_2$O (4:1). The product was further purified using column chromatography producing 0.92 g (83%) of a waxy light brown material.

III. Ring Opening Polymerizations

A. Preparation of Cationic Polymers Having Cholesteryl-Containing End Groups

In the reaction diagrams that follow, abbreviations $Z^1$ and $Z^2$ are used to represent the following steroid residues of the cationic polymers:

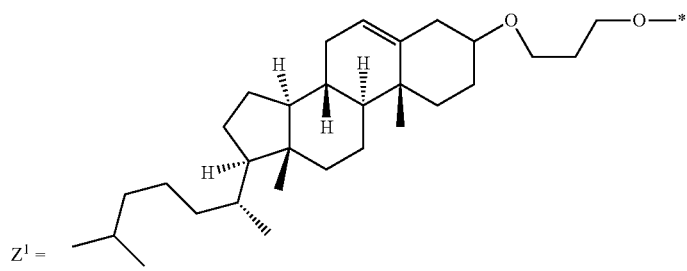

$Z^1 =$ $Z^2 =$ 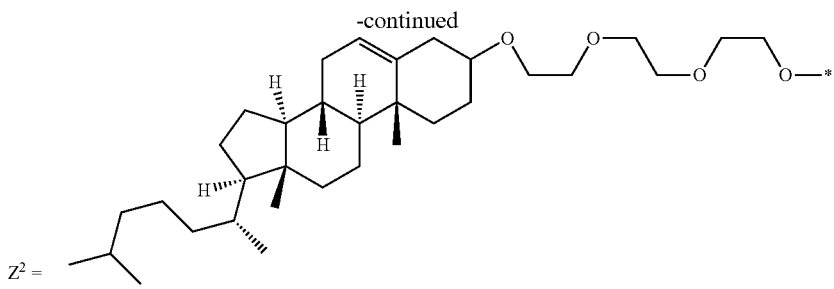

The starred bond indicates the attachment point to the cationic polymer backbone. The $Z^1$ and $Z^2$ residues are also residues of the initiator used to form the cationic polymers.

The preparation of Example 10 is representative. This cationic polymer was prepared according to the reaction sequence in Scheme 1.

was precipitated into isopropanol yielding 0.73 g (94%) white waxy polymer. The polymer was characterized using $^1$HNMR (CDCl$_3$) and GPC (THF, 37° C.). Complete polymerization was verified by the disappearance of a carbonate doublet (2H, —OCOOCH$_2$—, 4.7 ppm) with corresponding appearance of broad multiplet (6H, 4.2 ppm) encompassing Scheme 1.

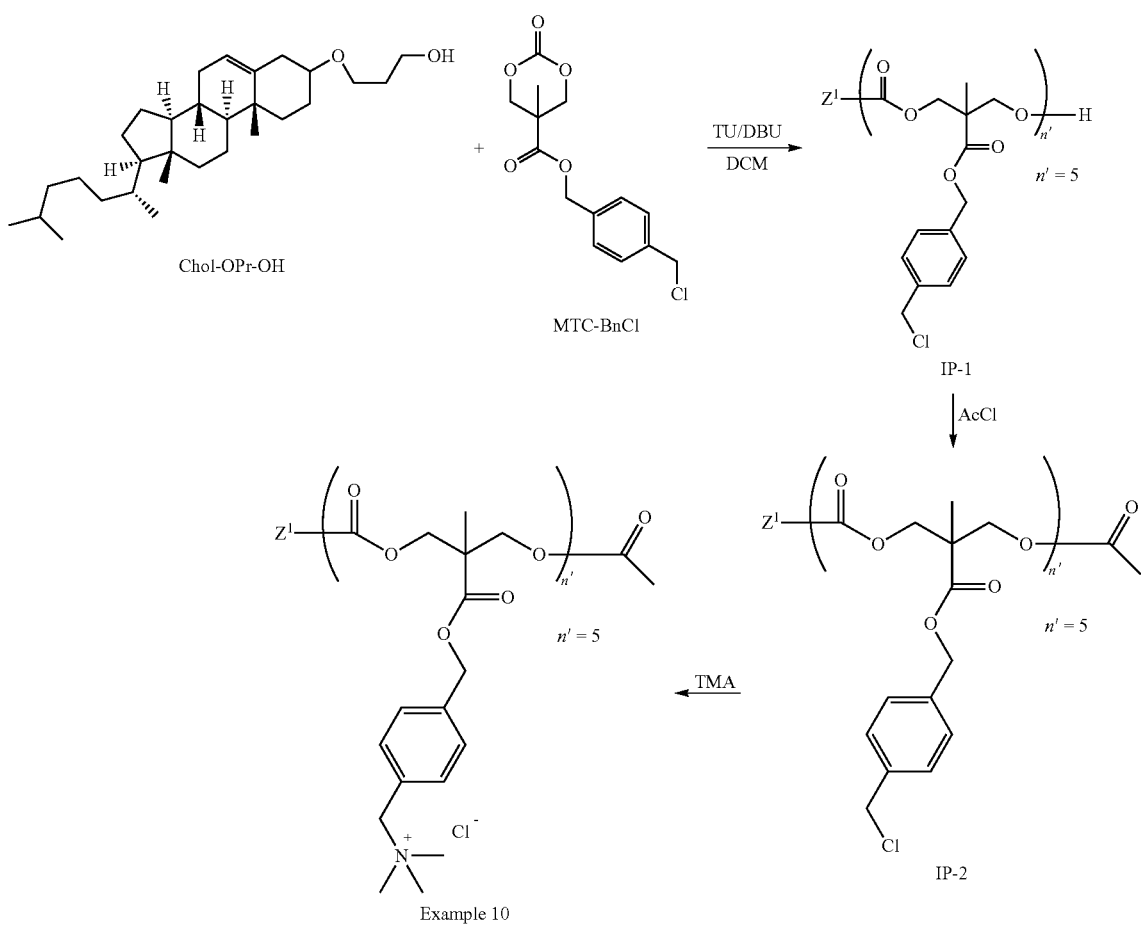

Example 10

Part 1. In an inert glovebox a vial was charged with Chol-OPr—OH (0.179 g, 0.4 mmol), TU (0.04 g, 0.1 mmol), MTC-BnCl (0.6 g, 2 mmol), dichloromethane (DCM) (3 g) and a stir bar. The reaction mixture was stirred and the polymerization started by the addition of DBU (20 microliters, 0.15 mmol). After 15 minutes excess acetyl chloride was added to quench the reaction and acetylate the IP-1 termini to form IP-2. Acetylated intermediate polymer IP-2 both newly formed linear carbonate methylenes (—CH$_2$OCOOCH$_2$—) and the benzyl ester. Molecular weight was verified by GPC and found to be 2.6 kDa with a PDI of 1.2. The average degree of polymerization (DP) was calculated by taking the ratio of cholesteryl methyl shift integration (3H, 0.87 ppm) against the benzyl chloride signal (2H, 5.0 ppm) which was in good agreement with GPC values.

Part 2. Quaternization of IP-2 with trimethylamine (TMA) to form CP-1. A vial was charged with acetylated intermediate polymer IP-2 (0.3 g, 0.15 mmol), acetonitrile (4 mL) and a stir bar. The reaction mixture was then placed in a dry ice/acetone bath (−78° C.) and excess TMA gas was bubbled through the stirred solution. The vial was then sealed and allowed to warm to ambient temperature with stirring. After 4 hours the diethyl ether (5 mL) was added to precipitate the product polymer. The reaction vial was then centrifuged for 10 minutes and the supernatant was decanted. The product was washed with excess diethyl ether and dried under high vacuum to yield 0.32 g (94%) translucent waxy material. The quaternization was verified using $^1$H NMR. A diagnostic chemical shift attributable to quaternized TMA (9H, 3.2 ppm) appeared and could be integrated against the benzyl ammonium signal (2H, 5.0 ppm) verifying complete conversion.

Quaternization of IP-2 with trimethylphosphine (TMP). to form Example 11 is representative.

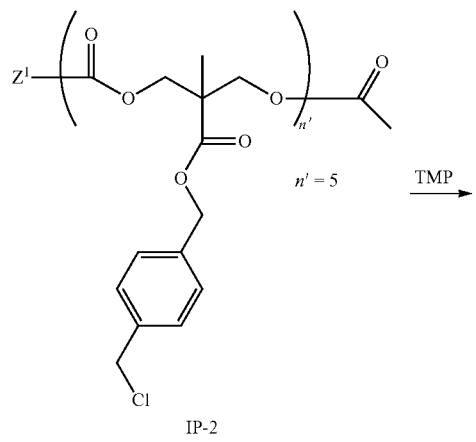

IP-2

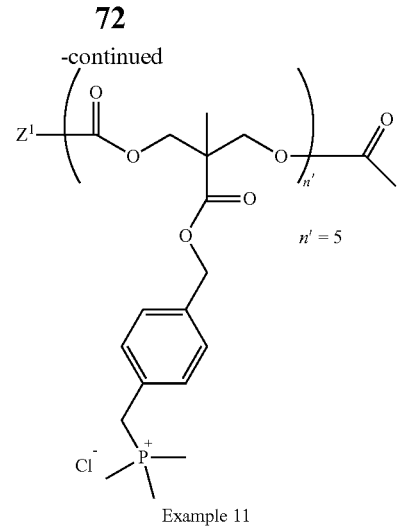

Example 11

A Schlenk tube was charged with IP-2 (0.3 g, 0.15 mmol), acetonitrile (4 mL) and a stir bar. The reaction mixture was then degassed via 3× freeze/pump/thaw cycles. Using a gastight syringe TMP (0.6 mL) was added and the solution was stirred at ambient temperature. After 4 hours the Schlenk tube was placed under house vacuum to remove excess TMP followed by the addition of ether (5 mL). The precipitate was collected, washed with excess ether and dried under high vacuum to yield 0.34 g (95%). The quaternization was verified using $^1$H NMR. A diagnostic chemical shift attributable to quaternized TMP (9H, 3.3 ppm) appeared and could be integrated against the benzyl ammonium signal (2H, 5.1 ppm) verifying complete conversion.

Examples 1 to 27. Cationic polymers were prepared according to the above general polymerization and quaternization procedures using either cholesterol (Chol-OH), Chol-OPr—OH or Chol-OTEG-OH as the steroid initiator for the ROP, either MTC-BnCl or MTC-PrCl as the cyclic carbonate monomer, and either TMA or TMP as the quaternizing agent.

Table 7 lists the cationic homopolymers prepared using the cholesteryl-based initiators, their degree of polymerization (DP), n', measured by $^1$H NMR, the critical micelle concentration (CMC), and the total carbons of the cationic side chain of the cationic repeat unit.

TABLE 7

| Ex. | Initiator | Endcap | Monomer | DP (n') | Quaternizing agent | CMC (mg/L) | Total cationic side chain carbons |
|---|---|---|---|---|---|---|---|
| 1 | Chol-OH | Acetyl | MTC-PrCl | 5 | TMA | 115.4 | 7 |
| 2 | Chol-OH | Acetyl | MTC-BnCl | 5 | TMA | 80.9 | 12 |
| 3 | Chol-OH | Acetyl | MTC-BnCl | 10 | TMA | 73.4 | 12 |
| 4 | Chol-OH | Acetyl | MTC-BnCl | 20 | TMA | 48.9 | 12 |
| 5 | Chol-OH | Acetyl | MTC-BnCl | 20 | TMP | 53.1 | 12 |
| 6 | Chol-OH | Acetyl | MTC-BnCl | 30 | TMA | 42.0 | 12 |
| 7 | Chol-OH | Acetyl | MTC-BnCl | 30 | TMP | 35.7 | 12 |
| 8 | Chol-OPr-OH | Acetyl | MTC-PrCl | 5 | TMA | 33.9 | 7 |
| 9 | Chol-OPr-OH | Acetyl | MTC-PrCl | 5 | TMP | 30.9 | 7 |
| 10 | Chol-OPr-OH | Acetyl | MTC-BnCl | 5 | TMA | 32.4 | 12 |
| 11 | Chol-OPr-OH | Acetyl | MTC-BnCl | 5 | TMP | 32.4 | 12 |
| 12 | Chol-OPr-OH | Acetyl | MTC-BnCl | 10 | TMA | 19.5 | 12 |
| 13 | Chol-OPr-OH | Acetyl | MTC-BnCl | 10 | TMP | 25.1 | 12 |
| 14 | Chol-OPr-OH | Acetyl | MTC-BnCl | 20 | TMA | 44.0 | 12 |
| 15 | Chol-OPr-OH | Acetyl | MTC-BnCl | 20 | TMP | 43.0 | 12 |
| 16 | Chol-OPr-OH | Acetyl | MTC-BnCl | 30 | TMA | 50.9 | 12 |
| 17 | Chol-OPr-OH | Acetyl | MTC-BnCl | 30 | TMP | 46.0 | 12 |
| 18 | Chol-OTEG-OH | Acetyl | MTC-PrCl | 5 | TMA | 33.1 | 7 |

TABLE 7-continued

| Ex. | Initiator | Endcap | Monomer | DP (n') | Quaternizing agent | CMC (mg/L) | Total cationic side chain carbons |
|---|---|---|---|---|---|---|---|
| 19 | Chol-OTEG-OH | Acetyl | MTC-PrCl | 5 | TMP | 38.9 | 7 |
| 20 | Chol-OTEG-OH | Acetyl | MTC-BnCl | 5 | TMA | 41.7 | 12 |
| 21 | Chol-OTEG-OH | Acetyl | MTC-BnCl | 5 | TMP | 30.9 | 12 |
| 22 | Chol-OTEG-OH | Acetyl | MTC-BnCl | 10 | TMA | 38.0 | 12 |
| 23 | Chol-OTEG-OH | Acetyl | MTC-BnCl | 10 | TMP | 28.2 | 12 |
| 24 | Chol-OTEG-OH | Acetyl | MTC-BnCl | 20 | TMA | 57.0 | 12 |
| 25 | Chol-OTEG-OH | Acetyl | MTC-BnCl | 20 | TMP | 56.2 | 12 |
| 26 | Chol-OTEG-OH | Acetyl | MTC-BnCl | 30 | TMA | 51.5 | 12 |
| 27 | Chol-OTEG-OH | Acetyl | MTC-BnCl | 30 | TMP | 44.0 | 12 |

B. Cationic Polymers Prepared with 4-Methyl Benzyl Alcohol Initiator

Examples 28 to 41. Cationic homopolymers were prepared according to the above general polymerization and quaternization procedures using 4-methyl benzyl alcohol (4-MeBnOH) as the initiator, either MTC-BnCl, MTC-PrCl, or MTC-PrBr as the cyclic carbonate monomer, and various amine quaternizing agents.

Table 8 lists the cationic homopolymers prepared using 4-MeBnOH initiator, their degree of polymerization (DP), the quaternizing agents, CMC, and the total number of carbons of each cationic repeat unit.

C. Cationic Random Copolymers Prepared with MTC-VitE Having a Side Chain Alpha-Tocopheryl Moiety Examples 42 to 50. Random cationic copolymers were prepared using MTC-PrBr and MTC-BnCl precursors for the cationic carbonate repeat units, MTC-VitE as the hydrophobic comonomer, benzyl alcohol (BnOH) initiator, and DBU/thiourea as catalysts. Quaternization was performed with trimethylamine or N-substituted imidazoles. The reaction sequence is shown in Scheme 2.

TABLE 8

| Ex. | Initiator | Endcap[a] | Monomer 1 | Feed Mole Ratio/DP[c] (n') | Quaternizing agent | CMC[b] | Total cationic side chain carbons |
|---|---|---|---|---|---|---|---|
| 28 | 4-MeBnOH | None | MTC-BnCl | 20/22.5 | TMA | N.D. | 12 |
| 29 | 4-MeBnOH | None | MTC-BnCl | 20/23.6 | Dimethyl ethylamine | N.D. | 13 |
| 30 | 4-MeBnOH | None | MTC-BnCl | 20/23.8 | Dimethyl butylamine | N.D. | 15 |
| 31 | 4-MeBnOH | None | MTC-BnCl | 20/26.0 | Dimethyl hexylamine | N.D. | 17 |
| 32 | 4-MeBnOH | None | MTC-BnCl | 20/20 | Dimethyl octylamine | N.D. | 19 |
| 33 | 4-MeBnOH | None | MTC-BnCl | 20/20.7 | Dimethyl benzylamine | N.D. | 18 |
| 34 | 4-MeBnOH | None | MTC-BnCl | 20/22.7 | Pyridine | N.D. | 14 |
| 35 | 4-MeBnOH | None | MTC-BnCl | 20/23.8 | Methyl imidazole | N.D. | 13 |
| 36 | 4-MeBnOH | None | MTC-BnCl | 20/20 | Butyl imidazole | N.D. | 16 |
| 37 | 4-MeBnOH | None | MTC-BnCl | 20/23 | Dimethyl butylamine/ Dimethyl benzylamine 50:50 | N.D. | 15/18 |
| 38 | 4-MeBnOH | None | MTC-BnCl | 20/20.5 | Dimethyl butylamine/ Dimethyl benzylamine 75:25 | N.D. | 15/18 |
| 39 | 4-MeBnOH | None | MTC-BnCl | 20/21.8 | TMA | N.D. | 12 |
| 40 | 4-MeBnOH | None | MTC-BnCl | 20/22.5 | TMA | N.D. | 12 |
| 41 | 4-MeBnOH | None | MTC-BnCl | 20/20 | Dimethyl cyclohexyl amine | N.D. | 17 |

[a]"None" means the terminal hydroxy group of the polycarbonate chain was not protected.
[b]N.D. means not determined.
[c]Actual, as determined by $^1$H NMR analysis

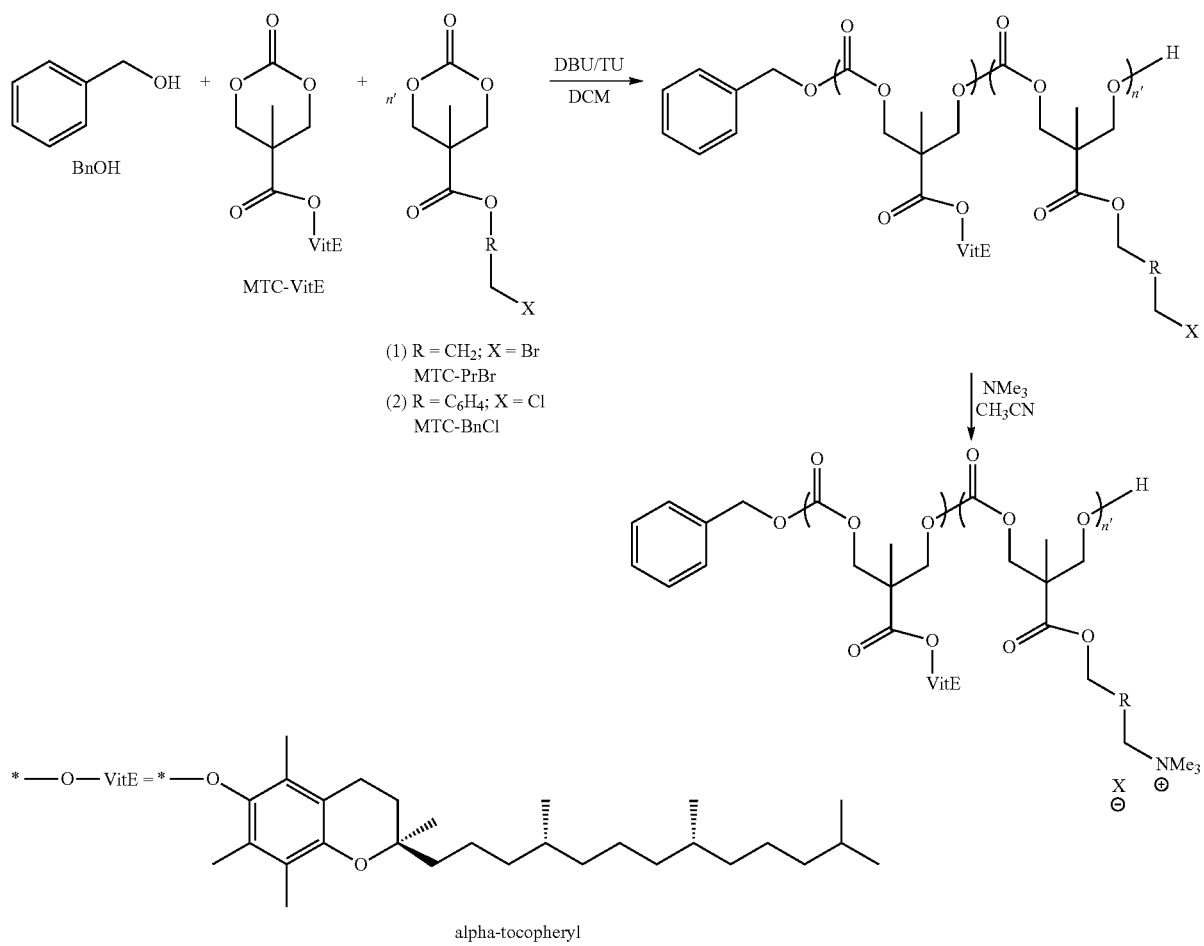

Scheme 2.

Example 50 is representative. In a 20 mL vial containing a magnetic stir bar in the glove box, MTC-BnCl (608.8 mg, 2.04 mmol, 30 equiv.), MTC-VitE (40.0 mg, 68 micromoles, 1.0 equiv.) and TU (25.2 mg, 68 micromoles, 1.0 equiv.) were dissolved in dichloromethane (3 mL). To this solution, BnOH (7.0 microliters, 68 micromoles, 1.0 equiv.) followed by DBU (10.2 microliters, 68 micromoles, 1.0 equiv.) were added to initiate polymerization. The reaction mixture was allowed to stir at room temperature for 20 min and quenched by the addition of excess (~20 mg) of benzoic acid. The mixture was then precipitated into ice-cold methanol (50 mL) and centrifuged at −5° C. for 30 minutes. The resultant semi-transparent oil was dried under vacuum until a foamy white solid was obtained. GPC analysis of the intermediate was carried out and the polymer was used without further purification. The polymer was subsequently dissolved in acetonitrile, transferred to a Teflon-plug sealable tube and chilled to 0° C. Trimethylamine was added to start the quaternization process. The reaction mixture was stirred at room temperature for 18 hours in the sealed tube. Precipitation of an oily material was observed during the course of reaction. The mixture was evacuated to dryness under vacuum and freeze-dried to finally yield a white crisp-foamy solid. The final polymer is characterized by 1H NMR to determine the final composition and purity.

Table 9 lists the cationic random copolymers prepared with MTC-VitE and BnOH initiator, their degree of polymerization (DP), quaternizing agent, CMC, and the total number of carbons of each cationic repeat unit.

TABLE 9

| Ex. | Initiator | Endcap[a] | Monomer 1/Monomer 2 | Feed Mole Ratio | DP[c] (n') | Quaternizing agent | CMC[b] (mg/L) | Total cationic side chain carbons |
|---|---|---|---|---|---|---|---|---|
| 42 | BnOH | None | MTC-PrBr | | 30 | 26 | TMA | N.D. | 7 |
| 43 | BnOH | None | MTC-BnCl | | 30 | 28 | TMA | N.D. | 12 |
| 44 | BnOH | None | MTC-VitE/ MTC-PrBr | 1:15 | 11 | TMA | N.D. | 7 |
| 45 | BnOH | None | MTC-VitE/ MTC-PrBr | 1:30 | 20 | TMA | 105 | 7 |

TABLE 9-continued

| Ex. | Initiator | Endcap[a] | Monomer 1/Monomer 2 | Feed Mole Ratio | DP[c] (n') | Quaternizing agent | CMC[b] (mg/L) | Total cationic side chain carbons |
|---|---|---|---|---|---|---|---|---|
| 46 | BnOH | None | MTC-VitE/MTC-PrBr | 1:45 | 35 | TMA | N.D. | 7 |
| 47 | BnOH | None | MTC-VitE/MTC-PrBr | 1:30 | 24 | MeIm | N.D. | 8 |
| 48 | BnOH | None | MTC-VitE/MTC-PrBr | 1:30 | 24 | EtIm | 52 | 9 |
| 49 | BnOH | None | MTC-VitE/MTC-BnCl | 1:10 | 8 | TMA | N.D. | 12 |
| 50 | BnOH | None | MTC-VitE/MTC-BnCl | 1:20 | 16 | TMA | N.D. | 12 |
| 51 | BnOH | None | MTC-VitE/MTC-BnCl | 1:30 | 23 | TMA | N.D. | 12 |

[a]"None" means the terminal hydroxy group of the polycarbonate chain was not protected.
[b]N.D. means not determined.
[c]Actual, as determined by $^1$H NMR analysis Table 10 lists the analytical properties of the cationic random copolymers prepared using MTC-VitE.

TABLE 10

| Ex. | Monomer 1/Monomer 2 | Selected $^1$H NMR peaks (intensity) | Added ratio | Actual ratio | GPC[a] |
|---|---|---|---|---|---|
| 42 | MTC-PrBr | 7.40 (s, 5H, initiator Ph), 5.15 (br, 2H, initiator CH$_2$Ph), 4.00-4.50 (overlapping peaks, 156H), 3.50 (m, 52H), 3.30-3.20 (m, 234H, N(CH$_3$)), 2.10 (m, 52H), 1.20 (s, 78H, CH$_3$) | 0:30 | 0:26 | 1.12 |
| 43 | MTC-BnCl | 7.30-7.70 (m, 117H, overlapping peaks of initiator Ph and Bn), 5.20 (s, 2H, CH$_2$Ph of initiator), 5.17 (m, 56H), 4.60-4.80 (m, 56H), 4.31 (m, 112H), 3.08 (m, 252H, N(CH$_3$)), 1.00-1.30 (m, 84H, CH$_3$) | 0:30 | 0:28 | 1.25 |
| 44 | MTC-VitE/MTC-PrBr | 7.10-7.60 (br, 5H, initiator Ph), 5.15 (br, 2H, initiator CH$_2$Ph), 4.00-4.50 (m, 66H), 3.55 (m, 22H), 3.30-3.20 (m, 99H, N(CH$_3$)), 2.10 (m, 22H), 1.00-2.00 (overlapping peaks, VitE), 0.70-0.90 (m, 12H, overlapping CH$_3$ on VitE) | 1:15 | 1:11 | 1.15 |
| 45 | MTC-VitE/MTC-PrBr | 7.10-7.60 (m, 5H, initiator Ph), 5.15 (m, 2H, initiator CH$_2$Ph), 4.00-4.50 (m, 120H), 3.46 (m, 40H), 3.30-3.20 (m, 180H, N(CH$_3$)), 2.10 (m, 40H), 1.00-2.00 (overlapping peaks, VitE), 0.70-0.90 (m, 12H, overlapping CH$_3$ on VitE) | 1:30 | 1:20 | 1.13 |
| 46 | MTC-VitE/MTC-PrBr | 7.10-7.60 (m, 5H, initiator Ph), 5.15 (m, 2H, initiator CH$_2$Ph), 4.00-4.50 (m, 120H), 3.46 (m, 70H), 3.30-3.20 (m, 315H, N(CH$_3$)), 2.10 (m, 70H), 1.00-2.00 (overlapping peaks, VitE), 0.70-0.90 (m, 12H, overlapping CH$_3$ on VitE) | 1:45 | 1:35 | 1.21 |
| 47 | MTC-VitE/MTC-PrBr | 9.00-9.50 (m, 24H, C—H Imdz), 7.50-8.00 (m, 48H, CH=CH Imdz), 4.00-4.50 (m, 192H, overlapping peaks), 3.80-4.00 (m, 72H, CH$_3$ Imdz), 2.20 (m, 48H), 1.00-2.00 (overlapping peaks, VitE), 0.80-0.90 (m, 12H, overlapping CH$_3$ on VitE) | 1:30 | 1:24 | 1.22 |
| 48 | MTC-VitE/MTC-PrBr | 9.00-9.50 (m, 24H, C—H Imdz), 7.70-8.00 (m, 48H, CH=CH Imdz), 4.00-4.50 (m, 240H, overlapping peaks), 2.20 (m, 48H), 1.45 (t, 72H, CH$_3$ Imdz), 1.00-2.00 (overlapping peaks, VitE), 0.80-0.90 (m, 12H, overlapping CH$_3$ on VitE) | 1:30 | 1:24 | 1.22 |
| 49 | MTC-VitE/MTC-BnCl | 7.10-7.60 (m, 40H, overlapping peaks of initiator Ph and Bn), 5.00-5.40 (m, 18H, overlapping peaks of initiator CH$_2$Ph and Bn), 4.60 (m, 16H), 4.28 (m, 32H), 3.06 (m, 72H, N(CH$_3$)), 1.00-2.00 (overlapping peaks, VitE), 0.70-0.90 (m, 12H, overlapping CH$_3$ on VitE) | 1:10 | 1:8 | 1.20 |

TABLE 10-continued

| Ex. | Monomer 1/ Monomer 2 | Selected $^1$H NMR peaks (intensity) | Added ratio | Actual ratio | GPC$^a$ |
|---|---|---|---|---|---|
| 50 | MTC-VitE/ MTC-BnCl | 7.10-7.70 (m, 69H, overlapping peaks of initiator Ph and Bn), 5.00-5.40 (m, 34H, overlapping peaks of initiator CH$_2$Ph and Bn), 4.68 (m, 32H), 4.29 (m, 64H), 3.07 (m, 144H, N(CH$_3$)), 1.00-2.00 (overlapping peaks, VitE), 0.70-0.90 (m, 12H, overlapping CH$_3$ on VitE) | 1:20 | 1:16 | 1.20 |
| 51 | MTC-VitE/ MTC-BnCl | 7.20-7.70 (m, 97H, overlapping peaks of initiator Ph and Bn), 5.00-5.40 (m, 48H, overlapping peaks of initiator CH$_2$Ph and Bn), 4.67 (m, 46H), 4.30 (m, 92H), 3.07 (m, 207H, N(CH$_3$)), 1.00-2.00 (overlapping peaks, VitE), 0.70-0.90 (m, 12H, overlapping CH$_3$ on VitE) | 1:30 | 1:23 | 1.21 |

$^a$GPC was performed on pre-quaternized polymers

C. Cationic Polymers Prepared with MTC-VitD2 Having a Side Chain Ergocalciferyl Moiety (Vitamin D2)

Examples 52 to 54. Example 54 is representative. In a 20 mL vial containing a magnetic stir bar in the glove box, MTC-BnCl (500.0 mg, 1.67 mmol, 3.0 equiv.), MTC-VitD2 (30.0 mg, 56 micromoles, 1.0 equivalent.) and TU (20.6 mg, 56 micromoles, 1.0 equiv.) were dissolved in dichloromethane (3 mL). To this solution, BnOH (5.8 microliters, 56 micromoles, 1.0 equivalent) followed by DBU (8.3 microliters, 56 micromoles, 1.0 equivalent) were added to initiate polymerization. The reaction mixture was allowed to stir at room temperature for 20 min and quenched by the addition of excess (~30 mg) of benzoic acid. The mixture was then precipitated into ice-cold methanol (50 mL) and centrifuged at −5° C. for 30 minutes. The resultant semi-transparent oil was dried under vacuum until a foamy white solid was obtained. GPC analysis of the intermediate polymer was carried out and the polymer was used without further purification. The polymer was subsequently dissolved in acetonitrile, transferred to a Teflon-plug sealable tube and chilled to 0° C. Trimethylamine was added to start the quaternization process. The reaction mixture was stirred at room temperature for 18 hours in the sealed tube. Precipitation of an oily material was observed during the course of reaction. The mixture was evacuated to dryness under vacuum and freeze-dried to finally yield a white crisp-foamy solid. The final polymer was characterized by $^1$H NMR to determine the final composition and purity.

Table 11 lists the cationic random copolymers prepared using MTC-VitD2, their degree of polymerization (DP), the quaternizing agents, CMC and the total number of carbons of each cationic repeat unit

TABLE 11

| Ex. | Initiator | Endcap$^a$ | Monomer 1/Monomer 2 | Feed Mole Ratio | DP$^c$ (n') | Quaternizing agent | CMC$^b$ (mg/L) | Total cationic side chain carbons |
|---|---|---|---|---|---|---|---|---|
| 52 | BnOH | None | MTC-VitD2/ MTC-BnCl | 1:10 | 9 | TMA | N.D. | 12 |
| 53 | BnOH | None | MTC-VitD2/ MTC-BnCl | 1:20 | 19 | TMA | N.D. | 12 |
| 54 | BnOH | None | MTC-VitD2/ MTC-BnCl | 1:30 | 28 | TMA | N.D. | 12 |

$^a$"None" means the terminal hydroxy group of the polycarbonate chain was not protected.
$^b$N.D. means not determined.
$^c$Actual, as determined by $^1$H NMR analysis Table 12 lists the analytical properties of the cationic random copolymers prepared using MTC-VitD2.

TABLE 12

| Ex. | Monomer 1/ Monomer 2 | Selected $^1$H NMR peaks (intensity) | Added ratio | Actual ratio | GPC$^a$ |
|---|---|---|---|---|---|
| 52 | MTC-VitD2/ MTC-BnCl | 7.20-7.70 (m, 41H, overlapping peaks of initiator Ph and Bn), 6.16 (d, 1H, J = 11.2 Hz, VitD2-C=CH$_2$), 5.90 (d, 1H, J = 11.2 Hz, VitD2-C=CH$_2$), 5.00-5.40 (m, 20H, overlapping peaks of initiator CH$_2$Ph and Bn), 4.64 (m, 18H), 4.28 (m, 36H), 3.06 (m, 81H, N(CH$_3$)), 0.90-2.40 (overlapping peaks, VitD2), 0.81 (t, 6H, J = 6.4 Hz, VitD2-CH$_3$) | 1:10 | 1:9 | 1.18 |

TABLE 12-continued

| Ex. | Monomer 1/ Monomer 2 | Selected $^1$H NMR peaks (intensity) | Added ratio | Actual ratio | GPC$^a$ |
|---|---|---|---|---|---|
| 53 | MTC-VitD2/ MTC-BnCl | 7.20-7.70 (m, 81H, overlapping peaks of initiator Ph and Bn), 6.16 (d, 1H, J = 11.2 Hz, VitD2-C=CH$_2$), 5.90 (d, 1H, J = 11.2 Hz, VitD2-C=CH$_2$), 5.00-5.50 (m, 40H, overlapping peaks of initiator CH$_2$Ph and Bn), 4.66 (m, 38H), 4.29 (m, 76H), 3.06 (m, 171H, N(CH$_3$)), 0.90-2.40 (overlapping peaks, VitD2), 0.81 (t, 6H, J = 6.4 Hz, VitD2-CH$_3$) | 1:20 | 1:19 | 1.19 |
| 54 | MTC-VitD2/ MTC-BnCl | 7.20-7.70 (m, 117H, overlapping peaks of initiator Ph and Bn), 6.16 (d, 1H, J = 11.2 Hz, VitD2-C=CH$_2$), 5.90 (d, 1H, J = 11.2 Hz, VitD2-C=CH$_2$), 5.00-5.40 (m, 58H, overlapping peaks of initiator CH$_2$Ph and Bn), 4.64 (m, 56H), 4.28 (m, 36H), 3.06 (m, 252H, N(CH$_3$)), 0.90-2.40 (overlapping peaks, VitD2), 0.81 (t, 6H, J = 6.4 Hz, VitD2-CH$_3$) | 1:30 | 1:28 | 1.21 |

$^a$GPC was performed on pre-quaternized polymers

Cationic Polymers Prepared with Diol Initiator Bn-MPA

Examples 55 to 63. A series of cationic polymers was prepared using Bn-MPA, a diol initiator. The preparation of Example 60 is representative.

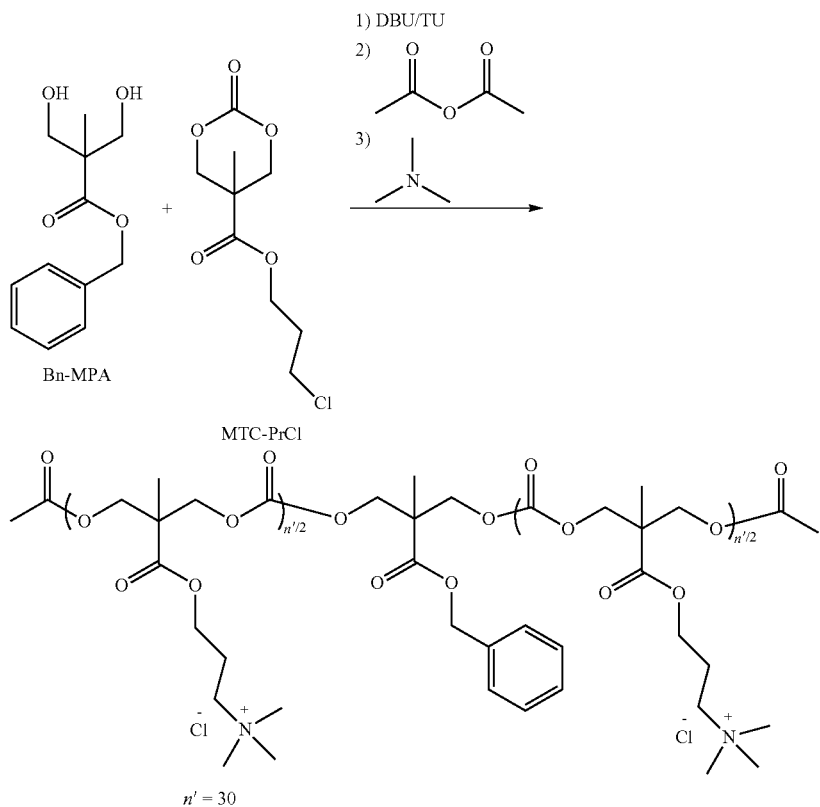

Example 56

MTCOPrCl (501 mg, 2.1 mmol), Bn-MPA (4.7 mg, 0.02 mmol, initiator), and TU (37.2 mg, 0.1 mmol) were dissolved in methylene chloride (1 mL), and this solution was transferred to a vial containing DBU (15.2 mg, 0.1 mmol) to start polymerization at room temperature ($[M]_0/[I]_0$=100). After 2 hours, acetic anhydride (72.4 mg, 0.71 mmol) was added into the mixture and the mixture was stirred for 48 hours (conversion ~95%). The solution was then precipitated into cold methanol twice and the precipitate was centrifuged and dried in vacuum. Yield: 466 mg (93%), GPC (THF): $M_n$ 12200 g/mol, PDI 1.17, $^1$H NMR (400 MHz, CDCl$_3$): delta 7.39-7.29 (m, 5H; Ph), 5.16 (s, 2H; PhCH$_2$), 4.38-4.19 (br, ~350H; CH$_2$OCOO, OCH$_2$ polymer), 3.64-3.55 (m, ~117H; CH$_2$Cl polymer), 2.15-2.07 (m, ~114H; CH$_2$ polymer), 2.06 (s, 6H; OCH$_3$ acetyl end), 1.27 (br, ~169H; CH$_3$ polymer). The initial polymer was added to a vial and dissolved in MeCN. The vial was then cooled to −78° C. and TMA gas was added. The vial was then heated to 50° C. and allowed to stir overnight or until reaction was complete. The reaction mixture was then precipitated into diethyl ether. The polymers were redissolved and precipitated into diethyl ether. Acetic anhydride can be substituted with acetyl chloride.

Table 13 lists the cationic copolymers prepared using Bn-MPA monomer, degree of polymerization (DP), quaternizing agent, CMC and the total number of carbons of each cationic repeat unit.

TABLE 13

| Ex. | Initiator | Endcap[a] | Monomer 1/ Monomer 2 | Feed Mole Ratio | DP[c] (n') | Quaternizing agent | CMC[b] (mg/L) | Total cationic side chain carbons |
|---|---|---|---|---|---|---|---|---|
| 55 | Bn-MPA | Acetyl | MTC-C8Cl | 100:0 | 15 | TMA | 79.4 | 12 |
| 56 | Bn-MPA | Acetyl | MTC-PrCl | 100:0 | 30 | TMA | 281.8 | 7 |
| 57 | Bn-MPA | Acetyl | MTC-C8Cl | 100:0 | 30 | TMA | 44.7 | 12 |
| 58 | Bn-MPA | Acetyl | MTC-C8Cl | 100:0 | 60 | TMA | 39.8 | 12 |
| 59 | Bn-PA | Acetyl | MTC-C8Cl/ MTC-PrCl | 75:25 | 30 | TMA | 56.2 | 12/7 |
| 60 | Bn-PA | Acetyl | MTC-C8Cl/ MTC-PrCl | 50:50 | 30 | TMA | 79.4 | 12/7 |
| 61 | Bn-PA | Acetyl | MTC-C8Cl/ MTC-PrCl | 25:75 | 30 | TMA | 158.5 | 12/7 |
| 62 | Bn-MPA | None | MTC-BnCl | 100:0 | 30 | TMA | | 12 |
| 63 | Bn-MPA | Acetyl | MTC-BnCl | 100:0 | 30 | TMA | | 12 |

[a]"None" means the terminal hydroxy group of the polycarbonate chain was not protected.
[b]N.D. means not observed.
[c]Actual, as determined by $^1$H NMR analysis; n' is the sum of all repeat units in both polycarbonate chains.

IV. Biological Measurements

Minimal Inhibitory Concentration (MIC) Measurements

Staphylococcus epidermidis (S. epidermidis) (ATCC No. 12228), Staphylococcus aureus (S. aureus) (ATCC No. 29737), Escherichia coli (E. coli) (ATCC No. 25922), Pseudomonas aeruginosa (P. aeruginosa) (ATCC No. 9027), and Candida albicans (C. albicans, a fungus) (ATCC No. 10231), Methicillin-resistant Staphylococcus aureus (MRSA) (clinically isolated, provided by Weimin Fan, Zhejiang University, China), Vancomycin-resistant Enterococcus (VRE) (clinically isolated, provided by Weimin Fan, Zhejiang University, China), Acinetobacter baumannii (A. baumannii) (clinically isolated, provided by Weimin Fan, Zhejiang University, China), Cryptococcus neoformans (C. neoformans) (clinically isolated, provided by Weimin Fan, Zhejiang University, China), and Klebsiella pneumoniae (K. pneumoniae) (clinically isolated, provided by Weimin Fan, Zhejiang University, China) were re-constituted from the lyophilized form. Bacterial samples were cultured in Mueller Hinton II broth (MHB II) at 37° C. under constant shaking of 300 rpm. The MICs of the polymers were measured using the broth microdilution method as reported previously. 100 microliters of MHB II or tryptic soy broth (TSB) containing a polymer at various concentrations was placed into each well of a 96-well tissue culture plate. An equal volume of bacterial suspension ($3 \times 10^5$ CFU/ml), where CFU means colony forming units, was added into each well. Prior to mixing, the bacterial sample was first inoculated overnight to enter its log growth phase. The concentration of bacterial solution was adjusted to give an initial optical density (O.D.) reading of approximately 0.07 at 600 nm wavelength on microplate reader (TECAN, Switzerland), which corresponds to the concentration of McFarland 1 solution ($3 \times 10^8$ CFU/ml). The bacterial solution was further diluted by 1000 times to achieve an initial loading of $3 \times 10^5$ CFU/ml. The 96-well plate was kept in an incubator at 37° C. under constant shaking of 300 rpm for 18 hours. The MIC was taken as the concentration of the antimicrobial polymer at which no microbial growth was observed with unaided eyes and microplate reader (TECAN, Switzerland) at the end of 18 hours incubation. Broth containing microbial cells alone was used as negative control, and each test was carried out in 6 replicates.

In the following tables, a lower MIC and a higher HC50 (or HC20) value are desirable. Bolded examples indicate the highest activity (lowest MIC values) against one or more of the microbes and the lowest toxicity to red blood cells (high HC50 values) in each series. The column labeled "Total cationic side chain carbons" is the number of carbons of the cationic side chain bearing the quaternary nitrogen or quaternary phosphorus groups of the cationic repeat unit.

Table 14 lists the MIC (mg/L) and HC50 (mg/L) values for the cholesteryl-initiated cationic polymers (Examples 1-27) against S. epidermidis, S. aureus, E. coli, P. aeruginosa, and C. albicans (fungus).

Table 15 lists the MIC and HC50 values for the 4-methyl benzyl alcohol initiated cationic polymers (Examples 28-41) against S. epidermidis, S. aureus, E. coli, P. aeruginosa, and C. albicans (fungus).

Table 16 is a continuation of the testing of (Examples 28-41) of Table 14, tested against methicillin-resistant Staphylococcus aureus (MRSA), vancomycin-resistant Enterococcus (VRE), Acinetobacter baumannii (A. baumannii), Cryptococcus neoformans (C. neoformans), and Klebsiella pneumoniae (K. pneumoniae).

Table 17 lists the MIC and HC20 values for the random cationic copolymers prepared with MTC-VitE comonomer (hydrophobic monomer having an alpha-tocopheryl side chain moiety) (Examples 42-51) against S. aureus, E. coli, P. aeruginosa, and C. albicans (fungus). Table 17 also lists the MIC and HC20 values for the random cationic copolymers prepared with MTC-VitD2 comonomer (hydrophobic monomer having a vitamin D2 side chain moiety) (Examples 52-54) against S. aureus and E. coli.

Table 18 lists the MIC and HC50 values for the diol initiated cationic polymers (Examples 55-63) against S. epidermidis, S. aureus, E. coli, P. aeruginosa, and C. albicans (fungus).

TABLE 14

| Example | Initiator | Endcap | Monomer 1 | DP (based on feed) | Quaternizing agent | Total cationic side chain carbons | MIC (mg/L), MHB[a] | | | | | HC$_{50}$ (mg/L) |
|---|---|---|---|---|---|---|---|---|---|---|---|---|
| | | | | | | | S. epidermidis | S. aureus | E. coli | P. aeruginosa | C. albicans | |
| 1 | Chol-OH | Acetyl | MTC-PrCl | 5 | TMA | 7 | 15.6 | 15.6 | 250 | >500 | 500 | |
| 2 | Chol-OH | Acetyl | MTC-BnCl | 5 | TMA | 12 | 3.9 | 15.6 | 31.3 | >500 | 250 | |
| 3 | Chol-OH | Acetyl | MTC-BnCl | 10 | TMA | 12 | 3.9 | 15.6 | 31.3 | >500 | 250 | |
| 4 | Chol-OH | Acetyl | MTC-BnCl | 20 | TMA | 12 | 15.6 | 31.3 | 62.5 | 62.5 | 250 | >500 |
| 5 | Chol-OH | Acetyl | MTC-BnCl | 20 | TMP | 12 | 15.6 | 31.3 | 31.3 | 250 | 250 | >500 |
| 6 | Chol-OH | Acetyl | MTC-BnCl | 30 | TMA | 12 | 7.8 | 31.3 | 62.5 | 62.5 | 250 | >500 |
| 7 | Chol-OH | Acetyl | MTC-BnCl | 30 | TMP | 12 | 7.8 | 31.3 | 62.5 | 62.5 | 250 | >500 |
| 8 | Chol-OPr-OH | Acetyl | MTC-PrCl | 5 | TMA | 7 | 31.3 | 125 | >500 | >500 | >500 | 120 |
| 9 | Chol-OPr-OH | Acetyl | MTC-PrCl | 5 | TMP | 7 | 62.5 | 62.5 | >500 | >500 | >500 | 300 |
| 10 | Chol-OPr-OH | Acetyl | MTC-BnCl | 5 | TMA | 12 | 31.3 | 31.3 | 125 | >500 | 250 | 170 |
| 11 | Chol-OPr-OH | Acetyl | MTC-BnCl | 5 | TMP | 12 | 7.8 | 15.6 | 31.3 | >500 | 250 | 100 |
| 12 | Chol-OPr-OH | Acetyl | MTC-BnCl | 10 | TMA | 12 | 15.6 | 31.3 | 125 | >500 | 500 | 380 |
| 13 | Chol-OPr-OH | Acetyl | MTC-BnCl | 10 | TMP | 12 | 7.8 | 7.8 | 31.3 | 125 | 125 | 400 |
| 14 | Chol-OPr-OH | Acetyl | MTC-BnCl | 20 | TMA | 12 | 7.8 | 15.6 | 62.5 | >500 | 125 | >500 |
| 15 | Chol-H OPr-OH | Acetyl | MTC-BnCl | 20 | TMP | 12 | 7.8 | 15.6 | 62.5 | >500 | 250 | >500 |
| 16 | Chol-OPr-OH | Acetyl | MTC-BnCl | 30 | TMA | 12 | 15.6 | 62.5 | 62.5 | >500 | 125 | >500 |
| 17 | Chol-H OPr-OH | Acetyl | MTC-BnCl | 30 | TMP | 12 | 7.8 | 62.5 | 31.3 | >500 | 250 | >500 |
| 18 | Chol-OTEG-OH | Acetyl | MTC-PrCl | 5 | TMA | 7 | 62.5 | 125 | >500 | >500 | 500 | 160 |
| 19 | Chol-OTEG-OH | Acetyl | MTC-PrCl | 5 | TMP | 7 | 62.5 | 31.3 | >500 | >500 | 500 | 420 |
| 20 | Chol-OTEG-OH | Acetyl | MTC-BnCl | 5 | TMA | 12 | 31.3 | 31.3 | 500 | >500 | 500 | 330 |
| 21 | Chol-OTEG-OH | Acetyl | MTC-BnCl | 5 | TMP | 12 | 7.8 | 15.6 | 31.3 | >500 | 250 | 140 |
| 22 | Chol-OTEG-OH | Acetyl | MTC-BnCl | 10 | TMA | 12 | 7.8 | 31.3 | 62.5 | >500 | 250 | 340 |
| 23 | Chol-OTEG-OH | Acetyl | MTC-BnCl | 10 | TMP | 12 | 3.9 | 15.6 | 31.3 | 125 | 125 | 400 |
| 24 | Chol-OTEG-OH | Acetyl | MTC-BnCl | 20 | TMA | 12 | 7.8 | 31.3 | 62.5 | 250 | 125 | >500 |
| 25 | Chol-OTEG-OH | Acetyl | MTC-BnCl | 20 | TMP | 12 | 15.6 | 31.3 | 31.3 | >500 | 125 | >500 |
| 26 | Chol-OTEG-OH | Acetyl | MTC-BnCl | 30 | TMA | 12 | 7.8 | 62.5 | 62.5 | 500 | 125 | >500 |
| 27 | Chol-OTEG-OH | Acetyl | MTC-BnCl | 30 | TMP | 12 | 7.8 | 31.3 | 31.3 | >500 | 250 | >500 |

[a]Mueller Hinton broth

TABLE 15

| Ex. | Initiator | Endcap | Monomer 1 | Feed Mole Ratio/DP (n') | Quaternizing agent 1/ Quaternizing agent 2 (mole ratio) | Total cationic side chain carbons | MIC (mg/L), TSB[a] | | | | | HC$_{50}$ (mg/L) |
|---|---|---|---|---|---|---|---|---|---|---|---|---|
| | | | | | | | S. epidermidis | S. aureus | E. coli | P. aeruginosa | C. albicans | |
| 28 | 4-MeBnOH | None | MTC-BnCl | 20/22.5 | TMA | 12 | 62.5 | 125 | >>500 | | | >4000 |
| 29 | 4-MeBnOH | None | MTC-BnCl | 20/23.6 | Dimethyl ethylamine | 13 | 31.3 | 125 | >>500 | | | >4000 |
| 30 | 4-MeBnOH | None | MTC-BnCl | 20/23.8 | Dimethyl butylamine | 15 | 3.9 | 15.6 | >>500 | | | >4000 |
| 31 | 4-MeBnOH | None | MTC-BnCl | 20/26.0 | Dimethyl hexylamine | 17 | 3.9 | 7.8 | 62.5 | | | 15.6 |
| 32 | 4-MeBnOH | None | MTC-BnCl | 20/20.7 | Dimethyl octylamine | 19 | 31.3 | 62.5 | 125 | | | 7.8 |
| 33 | 4-MeBnOH | None | MTC-BnCl | 20/20.7 | Dimethyl benzylamine | 18 | 7.8 | 15.6 | 125 | | | 250 |
| 34 | 4-MeBnOH | None | MTC-BnCl | 20/23.8 | Pyridine | 14 | | | | | | |
| 35 | 4-MeBnOH | None | MTC-BnCl | 20/20.0 | Methyl imidazole | 13 | 3.9 | 15.6 | >>500 | | | >1000 |
| 36 | 4-MeBnOH | None | MTC-BnCl | 20/23.0 | Butyl imidazole | 16 | 3.9 | 7.8 | 62.5 | | | 250 |
| 37 | 4-MeBnOH | None | MTC-BnCl | 20/20.5 | Dimethyl butylamine/ Dimethyl benzylamine (50:50) | 15/18 | 3.9 | 15.6 | 62.5 | | | >500 |
| 38 | 4-MeBnOH | None | MTC-BnCl | 20/21.8 | Dimethyl butylamine Dimethyl benzylamine (75:25) | 15/18 | 3.9 | 15.6 | 500 | | | |
| 39 | 4-MeBnOH | None | MTC-BnCl | 20/22.5 | TMA | 12 | 62.5 (MHB)[b] | 250 (MHB)[b] | >500 (MHB)[b] | | | |
| 40 | 4-MeBnOH | None | MTC-BnCl | 30/31.3 | TMA | 12 | 62.5 (MHB)[b] | 250 (MHB)[b] | >500 (MHB)[b] | | | |
| 41 | 4-MeBnOH | None | MTC-BnCl | 20/20 | Dimethyl cyclohexylamine | 17 | 7.8 | 15.6 | >>500 | | | 250 |

[a]tryptic soy broth
[b]Mueller Hinton broth

TABLE 16

Continuation of Examples 28-41 with different microbes

| Ex. | Initiator | Endcap | Monomer | Feed Mole Ratio/ DP (n') | Quaternizing agent 1/ Quaternizing agent 2 (mole ratio) | Total cationic side chain carbons | MIC (mg/L), MHB[a] | | | | | HC$_{50}$ (mg/L) |
|---|---|---|---|---|---|---|---|---|---|---|---|---|
| | | | | | | | MRSA | VRE | A. baumannii | C. neoformans | K. pneumoniae | |
| 28 | 4-MeBnOH | None | MTC-BnCl | 20/22.5 | TMA | 12 | 250 | 31.3 | 500 | 31.3 | >>500 | >4000 |
| 29 | 4-MeBnOH | None | MTC-BnCl | 20/23.6 | Dimethyl-ethylamine | 13 | | | | | | >4000 |
| 30 | 4-MeBnOH | None | MTC-BnCl | 20/23.8 | Dimethyl-butylamine | 15 | 7.8 | 3.9 | 62.5 | 31.3 | >>500 | >4000 |
| 31 | 4-MeBnOH | None | MTC-BnCl | 20/26.0 | Dimethyl-hexylamine | 17 | | | | | | 15.6 |
| 32 | 4-MeBnOH | None | MTC-BnCl | 20/20.7 | Dimethyl-octylamine | 19 | | | | | | 7.8 |
| 33 | 4-MeBnOH | None | MTC-BnCl | 20/20.7 | Dimethyl-benzylamine | 18 | 7.8 | 1.95 | 15.6 | 7.8 | 62.5 | 250 |
| 34 | 4-MeBnOH | None | MTC-BnCl | 20/23.8 | Pyridine | 14 | | | | | | |
| 35 | 4-MeBnOH | None | MTC-BnCl | 20/20.0 | Methyl-imidazole | 13 | | | | | | >1000 |
| 36 | 4-MeBnOH | None | MTC-BnCl | 20/23.0 | Butyl-imidazole | 16 | 3.9 | 1.95 | 15.6 | 7.8 | 62.5 | 250 |

TABLE 16-continued

Continuation of Examples 28-41 with different microbes

| Ex. | Initiator | Endcap | Monomer | Feed Mole Ratio/ DP (n') | Quaternizing agent 1/ Quaternizing agent 2 (mole ratio) | Total cationic side chain carbons | MIC (mg/L), MHB[a] | | | | | HC$_{50}$ (mg/L) |
|---|---|---|---|---|---|---|---|---|---|---|---|---|
| | | | | | | | MRSA | VRE | *A. baumannii* | *C. neoformans* | *K. pneumoniae* | |
| 37 | 4-MeBnOH | None | MTC-BnCl | 20/20.5 | Dimethyl-butylamine Dimethyl-benzylamine 50:50 | 15/18 | 3.9 | 3.9 | 31.3 | 7.8 | 250 | >500 |
| 38 | 4-MeBnOH | None | MTC-BnCl | 20/21.8 | Dimethyl-butylamine Dimethyl-benzylamine 75:25 | 15/18 | | | | | | |
| 39 | 4-MeBnOH | None | MTC-BnCl | 20/22.5 | TMA | 12 | | | | | | |
| 40 | 4-MeBnOH | None | MTC-BnCl | 30/31.3 | TMA | 12 | | | | | | |
| 41 | 4-MeBnOH | None | MTC-BnCl | 20/20 | Dimethyl-cyclohexylamine | 17 | | | | | | 250 |

[a]Mueller Hinton broth

TABLE 17

| Ex. | Initiator | Endcap | Monomer 1/ Monomer 2 | Feed Mole Ratio | DP (n') | Quaternizing agent | Total cationic side chain carbons | MIC (mg/L), TSB[a] | | | | | HC$_{50}$ (mg/L) |
|---|---|---|---|---|---|---|---|---|---|---|---|---|---|
| | | | | | | | | *S. epidermidis* | *S. aureus* | *E. coli* | *P. aeruginosa* | *C. albicans* | |
| 42 | BnOH | None | MTC-PrBr | 30 | 26 | TMA | 7 | | 500 | 1000 | >1000 | 500 | >1000 |
| 43 | BnOH | None | MTC-BnCl | 30 | 30 | TMA | 12 | | 125 | 125 | >1000 | 125 | >1000 |
| 44 | BnOH | None | MTC-VitE/ MTC-PrBr | 1:15 | 11 | TMA | 7 | | 63 | 125 | >1000 | 250 | >1000 |
| 45 | BnOH | None | MTC-VitE/ MTC-PrBr | 1:30 | 20 | TMA | 7 | | 63 | 250 | >1000 | 250 | >1000 |
| 46 | BnOH | None | MTC-VitE/ MTC-PrBr | 1:45 | 35 | TMA | 7 | | 63 | 250 | >1000 | 250 | >1000 |
| 47 | BnOH | None | MTC-VitE/ MTC-PrBr | 1:30 | 24 | Me-Imidazole | 8 | | 63 | 63 | 500 | 125 | 1000 |
| 48 | BnOH | None | MTC-VitE/ MTC-PrBr | 1:30 | 24 | Et-Imidazole | 9 | | 31 | 63 | >1000 | 250 | 500 |
| 49 | BnOH | None | MTC-VitE/ MTC-BnCl | 1:10 | 8 | TMA | 12 | | 31 | 63 | 1000 | 250 | 500 |
| 50 | BnOH | None | MTC-VitE/ MTC-BnCl | 1:20 | 16 | TMA | 12 | | 31 | 31 | 500 | 250 | 500 |
| 51 | BnOH | None | MTC-VitE/ MTC-BnCl | 1:30 | 23 | TMA | 12 | | 31 | 31 | 500 | 250 | 500 |
| 52 | BnOH | None | MTC-VitD2/ MTC-BnCl | 1:10 | 9 | TMA | 12 | | 31 | 63 | | | 1000 |
| 53 | BnOH | None | MTC-VitD2/ MTC-BnCl | 1:20 | 19 | TMA | 12 | | 31 | 63 | | | >1000 |
| 54 | BnOH | None | MTC-VitD2/ MTC-BnCl | 1:30 | 28 | TMA | 12 | | 31 | 63 | | | >1000 |

[a]tryptic soy broth

TABLE 18

| Ex. | Initiator | Endcap[a] | Feed Monomer 1/ Monomer 2 | Mole Ratio | DP[b] (n') | Quaternizing agent 1 | Total cationic side chain carbons | MIC (mg/L), TSB[c] S. epidermidis | S. aureus | E. coli | P. aeruginosa | C. albicans | HC$_{50}$ (mg/L) |
|---|---|---|---|---|---|---|---|---|---|---|---|---|---|
| 55 | Bn-MPA | Acetyl | MTC-C8Cl | 100:0 | 15 | TMA | 12 | 4 | 4 | 31 | 125 | 125 | 250-500 |
| 56 | Bn-MPA | Acetyl | MTC-PrCl | 100:0 | 30 | TMA | 7 | 16 | 500 | 1000 | >1000 | 500 | >1000 |
| 57 | Bn-MPA | Acetyl | MTC-C8Cl | 100:0 | 30 | TMA | 12 | 4 | 4 | 16 | 125 | 125 | 250 |
| 58 | Bn-MPA | Acetyl | MTC-C8Cl | 100:0 | 60 | TMA | 12 | 4 | 4 | 16 | 125 | 125 | 125-250 |
| 59 | Bn-MPA | Acetyl | MTC-C8Cl/ MTC-PrCl | 75:25 | 30 | TMA | 12/7 | 4 | 4 | 16 | 125 | 125 | 750 |
| 60 | Bn-MPA | Acetyl | MTC-C8Cl/ MTC-PrCl | 50:50 | 30 | TMA | 12/7 | 8 | 8 | 31 | 250 | 125 | >1000 |
| 61 | Bn-MPA | Acetyl | MTC-C8Cl/ MTC-PrCl | 25:75 | 30 | TMA | 12/7 | 16 | 31 | 63 | 1000 | 125 | >1000 |
| 62 | Bn-MPA | None | MTC-BnCl | 100:0 | 30 | TMA | 12 |  | 31.3 | 62.5 | >1000 | 125 | >1000 |
| 63 | Bn-MPA | Acetyl | MTC-BnCl | 100:0 | 30 | TMA | 12 | 4 | 125 | 125 | >1000 | 125 | >1000 |

[a] both polycarbonate chains were end capped
[b] sum of all polycarbonate repeat units of the cationic polymer
[c] tryptic soy broth Lower MIC (500 mg/L or less) and higher HC50 or HC20 (500 mg/L or more) represent preferred performance. HC20 is a more sensitive measure of red blood cell toxicity than HC50. That is, if the HC20 value is 1000, then the HC50 value will be even higher. An HC selectivity (HC50/MIC or HC20/MIC) value of 3 or more is also preferred.

With respect to cholesteryl-containing "all-cationic" polymers of Table 14, those formed with TMP quaternizing agent were generally more active than cationic polymers formed with TMA, other features being the same (e.g., compare Example 20 with Example 21, and Example 12 with Example 13). Higher activity was also observed with cationic polymers formed with cyclic carbonate monomer MTC-BnCl compared to MTC-PrCl, other features being the same (e.g., compare Example 8 with Example 10, and Example 9 with Example 11). A degree of polymerization (DP) of 20 to 30 was generally favored over a DP of 5 to 10. P. aeruginosa was generally resistant, but responded well to cationic polymers having a DP of 20 or 30 having a cholesteryl end group (Examples 4 to 7, which were initiated with cholesterol).

The positive effects of the cholesteryl-containing end group on antimicrobial activity is further evidenced by comparing Examples 4 and 6 (Table 14) with Examples 28 and 40 (Table 15) and Examples 42 and 43 (Table 17). Examples 28 and 40 have a 4-methyl benzyloxy end group (formed from 4-MeBnOH initiator), and Examples 42 and 43 have a benzyloxy end group (formed from BnOH initiator).

The examples of Table 15 show that the generally weaker antimicrobial activity of the cationic polymers having smaller end groups (i.e., end groups having less than 15 carbons) can be compensated for using bulkier Q' substituents ($R^a$ groups). In this instance Q' is nitrogen. Example 37 is representative. Example 37 is a homopolymer of MTC-BnCl initiated with 4-MeBnOH and quaternized with a mixture of dimethyl butyl amine (6 carbons) and dimethyl benzylamine (9 carbons) in a 1:1 molar ratio. Example 37 has high activity and high HC50, comparable to or better than a cholesteryl-containing polymer, other features being the same (compare Example 37 with Example 24 of Table 14). The HC50 selectivity (HC50/MIC) of Example 37 is also excellent, from >8 against P. aeruginosa to >128 against S. aureus) The dimethyl butyl amine/dimethyl benzylamine mixture produces cationic carbonate repeat units having a total of 15 and 18 carbons, respectively. Example 37 was also highly active against MRSA, VRE, A. baumannii, C. neoformans, and K. pneumoniae (Table 16).

Smaller end groups can also be compensated for using a hydrophobic comonomer and, optionally, a bulky quaternizing agent (e.g., one in which the $R^a$ groups of quaternary ammonium group have a combined total of more than 3 carbons). This can be seen by comparing in Table 17 Examples 42 (MTC-PrCBr, DP 30, no hydrophobic comonomer) with Examples 45, 47 and 48 (MTC-PrBr plus about 3 mol % to about 5 mol % of MTC-VitE, DP 30). A similar trend is shown for MTC-BnCl with and without MTC-VitE or MTC-VitD (compare Example 43 with Examples 51 and 54). The molecular formula of alpha-tocopherol is $C_{29}H_{50}O_2$, and the molecular formula of ergocalciferol is $C_{28}H_{44}O$, suggesting that hydrophobic comonomers, particularly those comprising a bound form of a biologically active/compatible material comprising 20 or more carbons, can be used in small amounts to control antimicrobial activity and/or red blood cell toxicity.

Killing Efficiency of Cholesteryl-Containing Polymers

Similar to MIC testing, 100 microliters of MHB II containing a polymer at various concentrations (0, MIC and 2.0MIC) was placed into each well of a 96-well tissue culture plate. An equal volume of bacterial suspension (3×10$^5$ CFU/ml), where CFU means colony forming units, was added into each well. Prior to mixing, the bacterial sample was first inoculated overnight to enter its log growth phase. The concentration of bacterial solution was adjusted to give an initial optical density (O.D.) reading of approximately 0.07 at 600 nm wavelength on microplate reader (TECAN, Switzerland), which corresponds to the concentration of McFarland 1 solution (3×10$^8$ CFU/ml). The bacterial solution was further diluted by 1000 times to achieve an initial loading of 3×10$^5$ CFU/ml. The 96-well plate was kept in an incubator at 37° C. under constant shaking of 300 rpm for 18 hours. The respective samples were then subjected to a series of ten-fold dilutions and plated onto lysogeny broth (LB) agar plates. The plates were then incubated overnight and counted for colony-forming units. A sample containing microbes treated with broth containing 10% v/v water was used as a control.

Figure 1B:
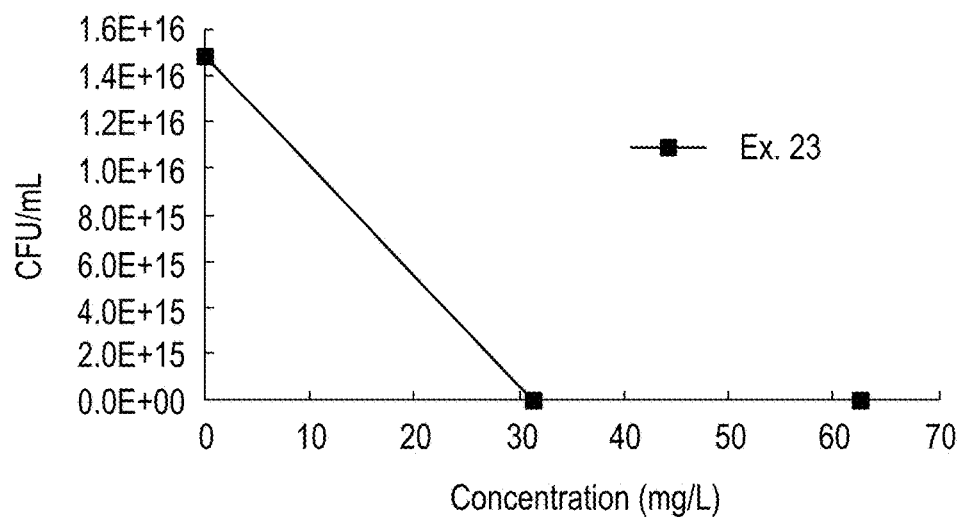

FIGS. 1A and 1B are graphs showing the relationship between colony forming units/mL of S. aureus as a function of concentration of Example 13 and Example 23 (Table 14), respectively. In both cases, the CFU count was zero at a cationic polymer concentration of 31 mg/L.

Hemolytic Activity Testing of Cholesteryl-Containing Polymers

Fresh rabbit blood cells or rat blood cells were subjected to 25× dilution with phosphate buffered saline (PBS) to obtain an approximate 4% v/v suspension for use in this experiment. Red blood cell suspension (300 microliters) was added to each tube containing an equal volume (300 microliters) of polymer solution in PBS (with final polymer concentrations ranging from 3.9-500 mg/L). The tubes were then incubated at 37° C. for 1 hour before they were centrifuged at 1000×g for 5 min. Aliquots (100 microliters) of supernatant were transferred to each well of a 96-well plate and analyzed for hemoglobin release at 576 nm using a microplate reader (TECAN, Switzerland). Red blood cells suspension incubated with PBS was used as negative control. Absorbance of red blood cells lyzed with 0.1% v/v Triton X-100 was used as the positive control and taken to be 100% hemolytic. Percentage of hemolysis was calculated using the following formula:

Hemolysis (%)=[(O.D.$_{576\,nm}$ of treated sample−O.D.$_{576\,nm}$ of negative control)/(O.D.$_{576\,nm}$ of positive control−O.D.$_{576\,nm}$ of negative control)]×100.

Data are expressed as mean±standard deviations of 4 replicates.

Figure 2A:
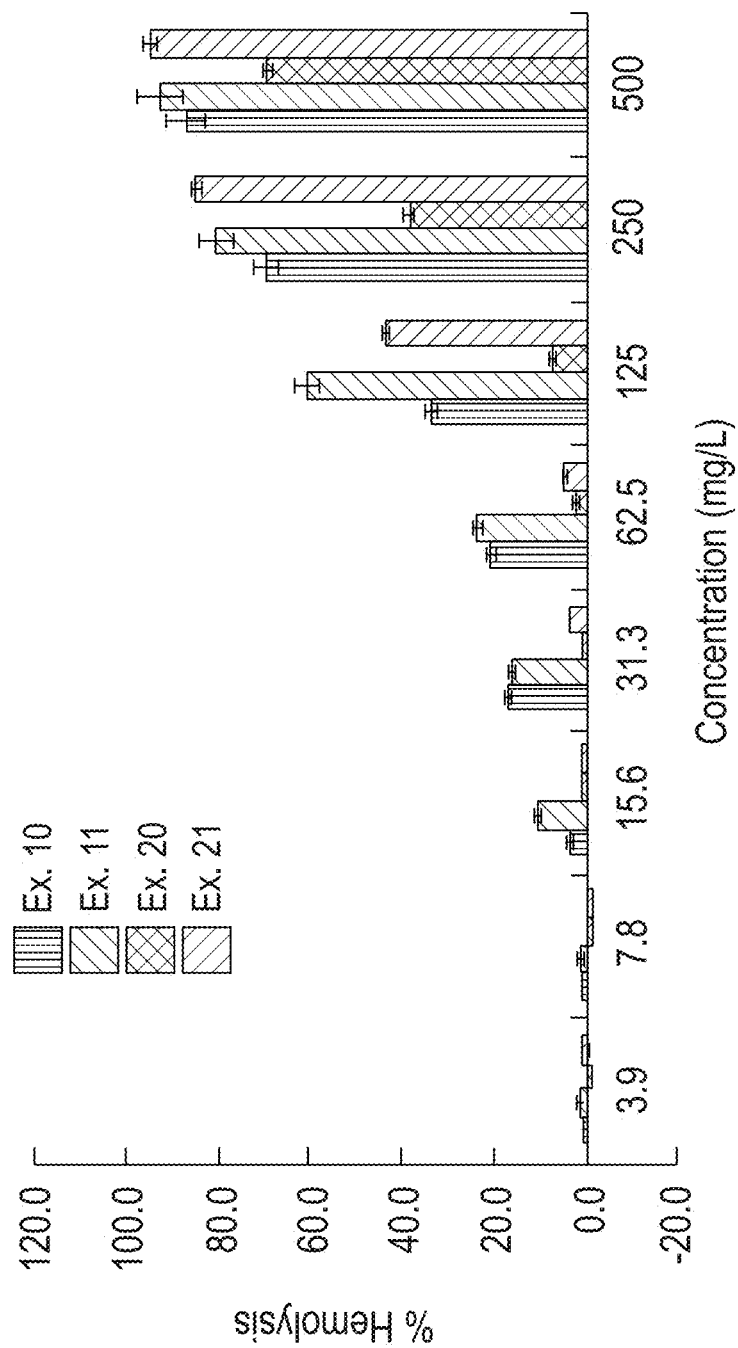
FIG. 2A-2C are graphs showing the % hemolysis of rabbit red blood cells as a function of concentration of cationic polymer Examples 10, 11, 20, 21 (FIG. 2A), Examples 8, 9, 18, 19 (FIG. 2B), and Examples 12, 13, 22, 23 (FIG. 2C).
Figure 2B:
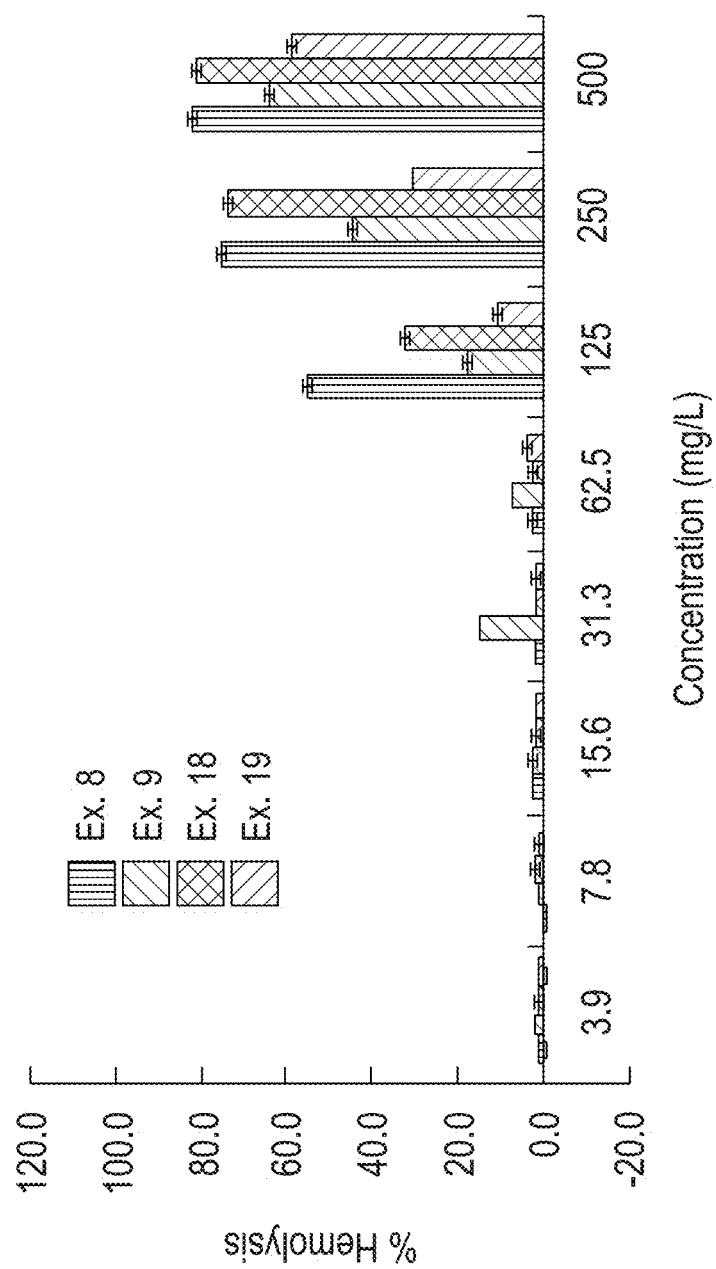
Figure 2C:
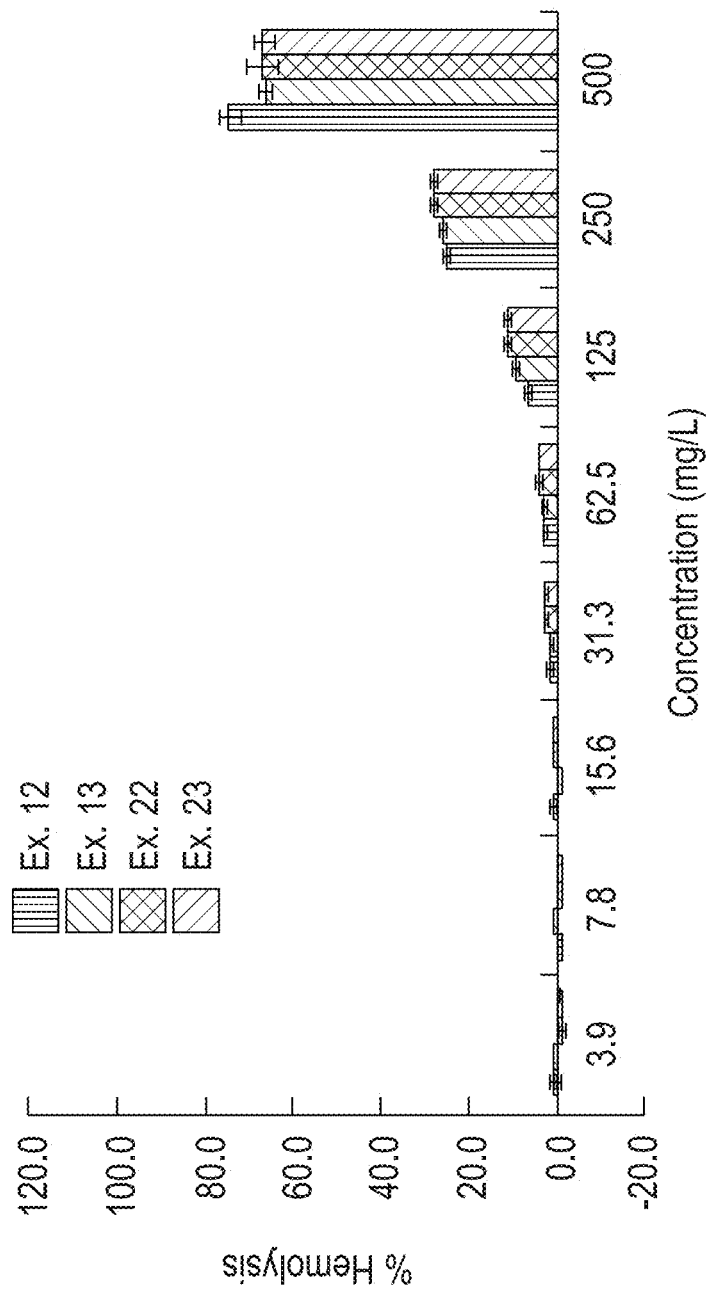

FIG. 2A to 2C are graphs showing the % hemolysis of rabbit red blood cells as a function of concentration (mg/L) of the cholesterol-containing cationic polymer Examples 10, 11, 20, 21 (FIG. 2A), Examples 8, 9, 18, 19 (FIG. 2B), and Examples 12, 13, 22, 23 (FIG. 2C). A smaller % hemolysis is preferred. The % hemolysis of cationic polymers having DP 5 (FIGS. 2A and 2B) was less than 25% at concentrations of 3.9 mg/L to 62.5 mg/L. Comparing Examples 10, 11, 20, and 21 of FIG. 2A at 62.4 mg/L, less hemolysis was observed with cationic polymers having the -OTEG-O- group compared to the —OPr—O— group in the initiator residue. Comparing FIGS. 2A and 2B with FIG. 2C, a lower % hemolysis was also observed with cationic polymers having DP 10 compared to DP 5. For cationic polymers of DP 10, less than about 15% hemolysis was observed up to a concentrations of about 125 mg/L (FIG. 2C). Changing the quaternizing agent from TMA to TMP in Examples 12, 13, 22, and 23 (FIG. 2C) did not significantly alter the hemolytic activity of the cationic polymers.

Cytotoxicity Testing of Cholesteryl-Containing Polymers

Human dermal fibroblast (HDF) cells were maintained in DMEM growth medium supplemented with 10% fetal bovine serum (FBS), sodium pyruvate, 100 U/mL penicillin and 100 mg/mL streptomycin and cultured at 37° C. under an atmosphere of 5% $CO_2$ and 95% humidified air. The cytotoxicity of the polymers was studied using the standard MTT assay protocol. HDF cells were seeded onto 96-well plates at a density of $1.5\times10^4$ cells per well and allowed to adhere overnight. The polymers were first dissolved in high pressure liquid chromatography (HPLC) grade water and serially diluted using Dulbecco's Modified Eagle Medium (DMEM) growth medium to achieve polymer concentrations ranging from 3.9 to 500 mg/L with water concentration fixed at 10% v/v for each condition. 100 microliters of polymer solution was added to the cells in each well and the plate was allowed to incubate for 18 hours at 37° C. Subsequently, 100 microliters of growth media and 10 microliters of MTT solution (5 mg/ml in PBS) were added to each well and the cells were incubated for 4 hours at 37° C. according to the manufacturer's directions. Resultant formazan crystals formed in each well were solubilized using 150 microliters of dimethylsulfoxide (DMSO) upon removal of growth media and the absorbance was determined using a microplate spectrophotometer at wavelengths of 550 nm and 690 nm. Relative cell viability was expressed as [($A_{550}$-$A_{690}$)sample/($A_{550}$-$A_{690}$)control]×100%. Data are expressed as mean±standard deviations of 3-4 replicates per polymer concentration.

Figure 3A:
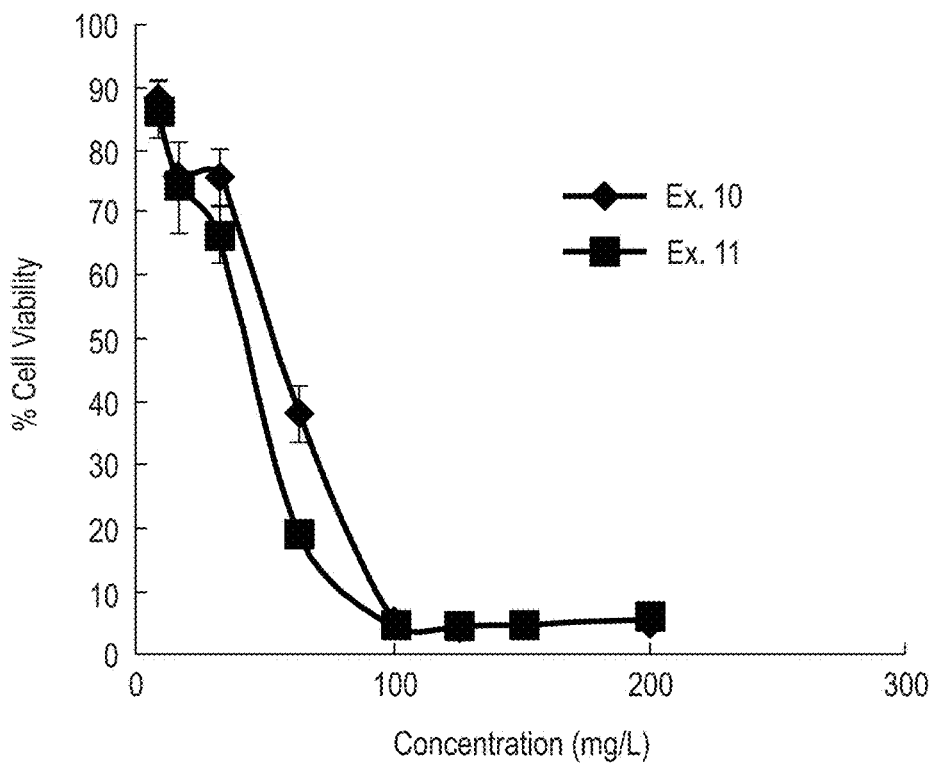
FIG. 3A-3F are graphs showing % cell viability of human dermal fibroblast (HDF) cells treated with various concentrations of cationic polymers.
Figure 3B:
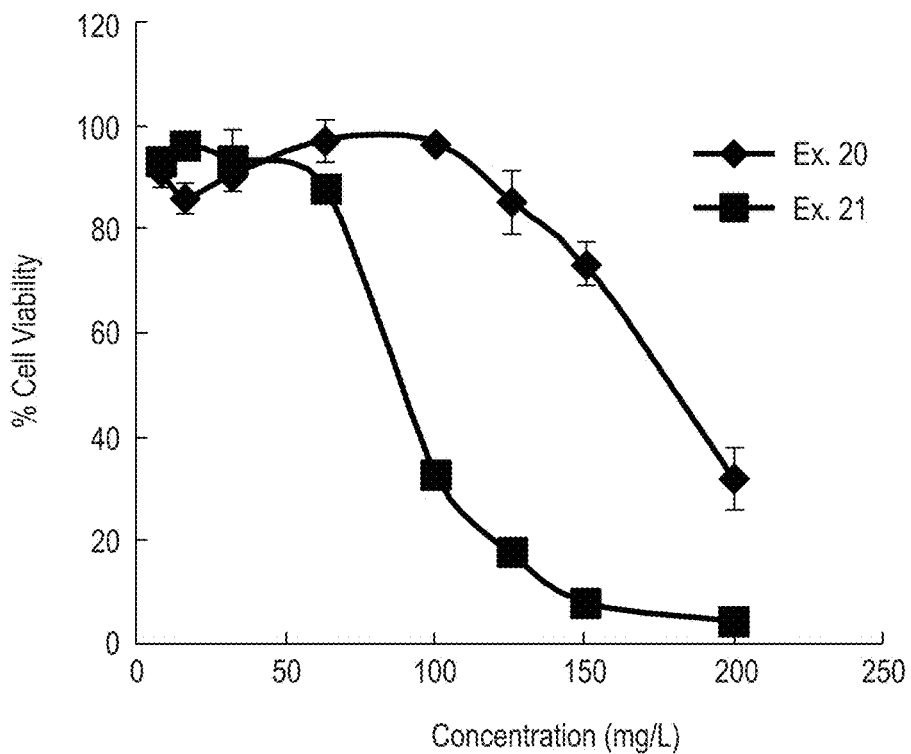
Figure 3C:
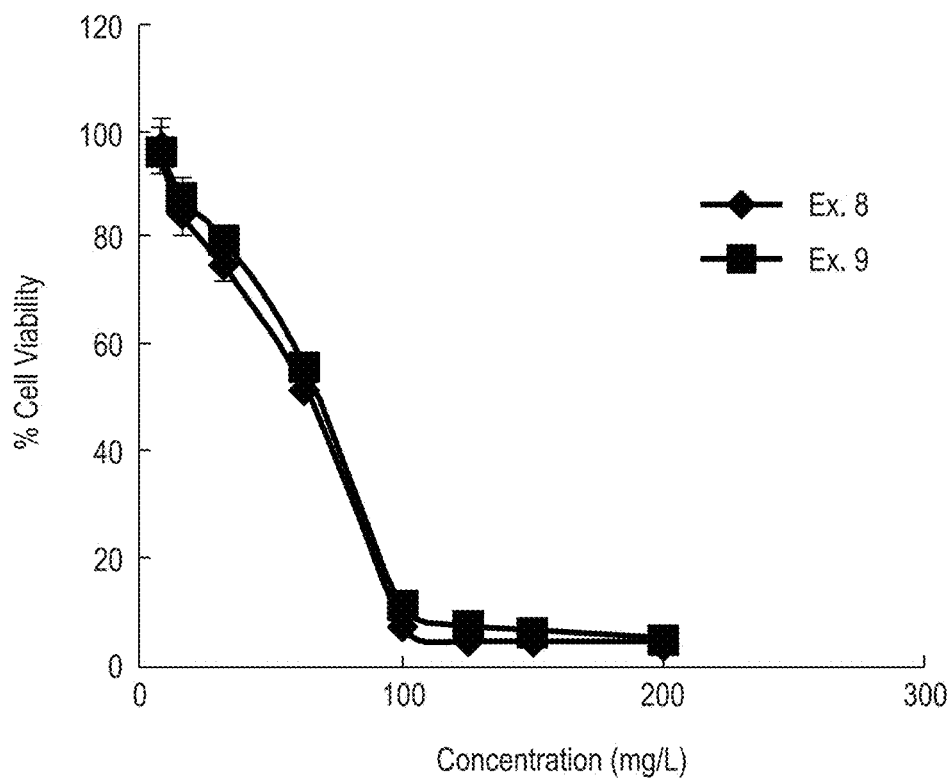
Figure 3D:
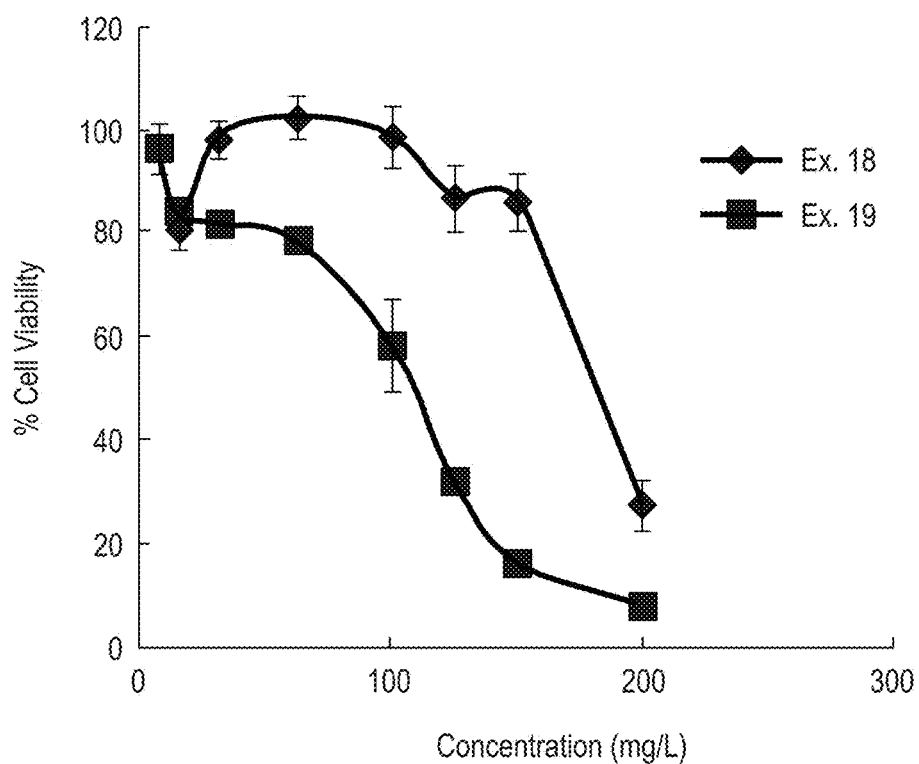
Figure 3E:
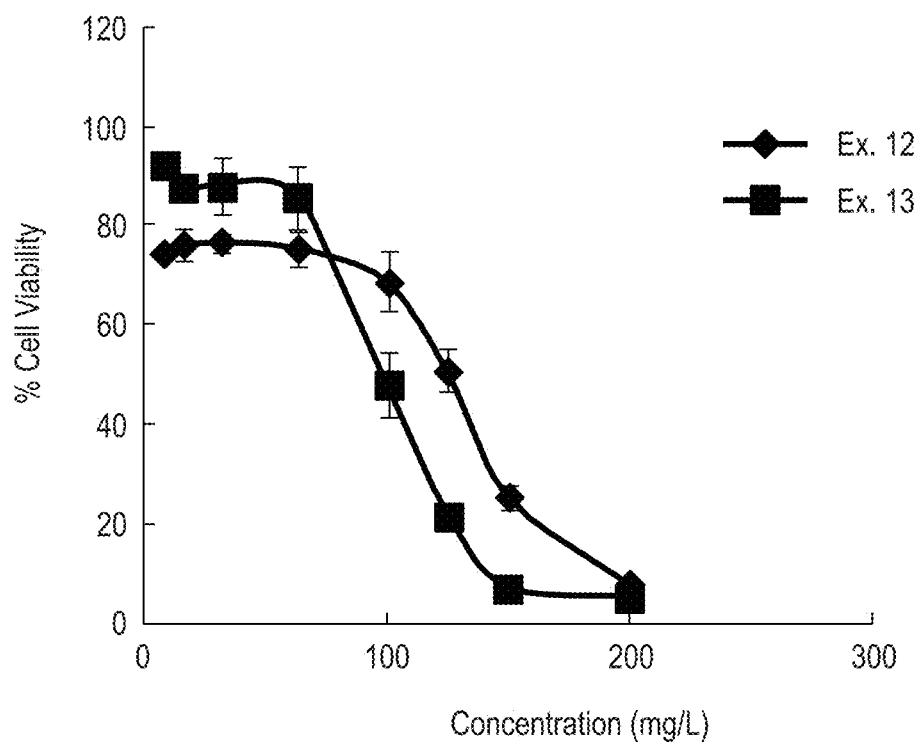
Figure 3F:
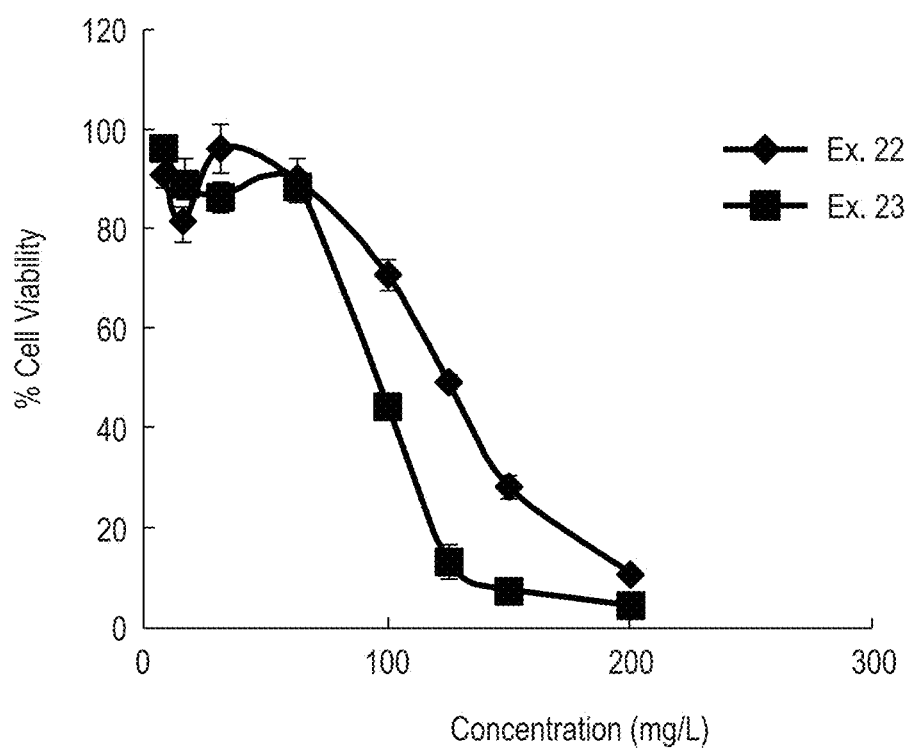

FIGS. 3A to 3F are graphs showing the percent cell viability of HDF cells as a function of cholesterol-containing cationic polymer concentration. Higher percent cell viability values are desirable at a given concentration. Comparing the various curves in this series, it can be seen that cell viability is favored by the use of TMA over TMP (compare Example 10 with Example 11 of FIG. 3A, Example 20 with Example 21 in FIG. 3B, and Example 18 with Example 19 in FIG. 3D). Higher percent cell viability was also favored by the use of Chol-OTEG-OH over Chol-OPr—OH. This can be seen by comparing Example 10 (FIG. 3A) with Example 20 (FIG. 3B), and Example 8 (FIG. 3C) with Example 18 (FIG. 3D). Higher percent cell viability was also favored by DP 10 over DP5. This can be seen by comparing Example 10 (FIG. 3A) with Example 12 (FIG. 3E), and Example 11 (FIG. 3A) with Example 13 (FIG. 3E). Example 20 (FIG. 3B) and Example 18 (FIG. 3D) had the highest cell viabilities over the widest concentration range (more the 80% viability up to about 125 mg/L and 150 mg/L, respectively.

Antimicrobial and Hemolysis Studies of Alpha-Tocopherol and Ergocalciferol (Vitamin D2) Functionalized Polymers Cationic polymers comprising a vitamin E moiety (prepared with MTC-VitE) were tested against various strains of bacteria in solution as shown above. Table 17 summarizes the antimicrobial, selectivity and hemolysis results. In general, incorporation of an alpha-tocopheryl moiety increases the inhibition efficiency against most bacteria. For cationic copolymers prepared with MTC-MTC-PrBr and quaternized with trimethylamine (TMA), MIC values decreased against *S. aureus* and *E. coli* with addition of MTC-VitE (compare Example 42 with Examples 44 to 46). The selectivity for *S. aureus* over rat red blood cells (RBCs), as measured by the MIC/HC20 values, was greater than 16 for Example 45 (>1000/63). When the quaternizing agent was changed from trimethylamine to methyl imidazole (Example 47) or ethyl imidazole (Example 48), MIC values for *E. coli* decreased to 63 mg/L (from 1000 for Example 42). Although Example 48 has a higher hemolytic toxicity against mammalian RBCs compared to Example 47, it does not induce significant hemolysis at its therapeutic concentrations. All the MTC-VitE polymers display significant activity towards *C. albicans*, especially Example 47 quaternized with methyl imidazole.

For cationic polymers prepared with MTC/VitE/MTC-BnCl (Examples 49 to 51), effectiveness against *S. aureus* and *E. coli* was more pronounced. The MIC of Examples 49 to 51 against *S. aureus* was 31 mg/L, whereas the control polymer (Example 43, no MTC-VitE) had a MIC of 125 mg/L against *S. aureus*. In this instance, the degree of polymerization (DP) seemingly did not give rise to significant differences in terms of bacteria inhibition. However, against *E. coli*, Example 51 (MTC-VitE/MTC-BnCl ratio of 1:30, MIC=31 mg/L) was more efficient than Example 49 (MTC-VitE/MTC-BnCl ratio of 1:10, MIC=63 mg/L).

The activity against the fungus *C. albicans* increased for the vitamin E-containing cationic polymers prepared with MTC-PrBr (Examples 44-48) compared to the control sample without a vitamin E moiety (Example 42). However, the activity against the fungus *C. albicans* decreased for vitamin E-containing cationic polymers prepared with MTC-BnCl (Examples 49-51) compared to the control sample having no vitamin E moiety (Example 43). This might be due to limited solubility of the vitamin E-containing polymers in the yeast broth. Otherwise, the polymers were potent inhibitors against *S. aureus* and *E. coli*. Most of the polymers also showed good selectivity. HC20/MIC values were in a range of about 4 to about 30 for *S. aureus* and *E. coli*.

Figure 4:
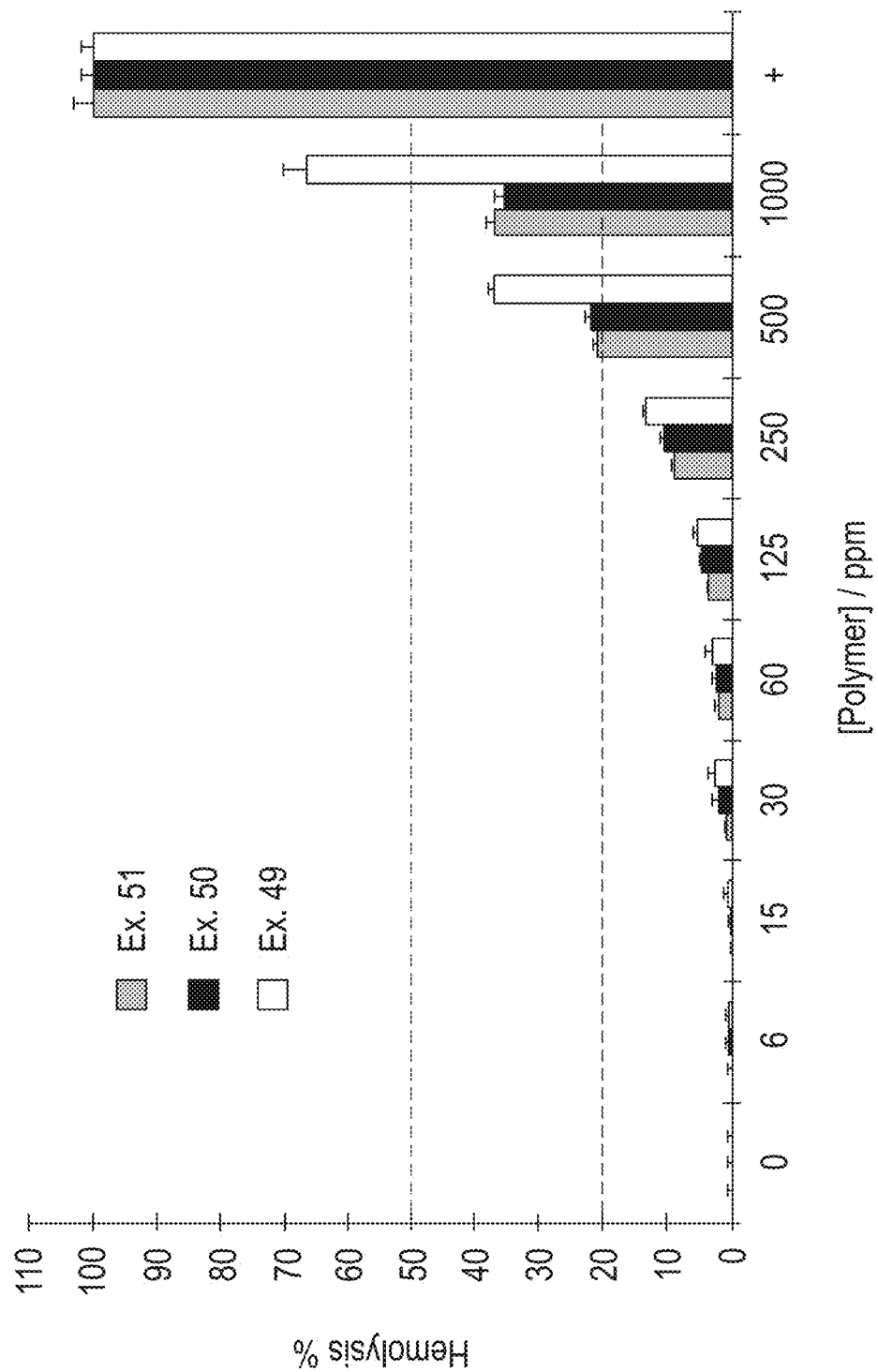
FIG. 4 is a graph showing the hemolysis activity against rat red blood cells of Examples 49 to 51 containing a pendant alpha-tocopheryl moiety.

The hemolysis activity of vitamin E-containing cationic polymers Examples 49 to 51 (prepared with MTC-BnCl) is shown in FIG. 4 (bar chart). Hemolysis assays using rat RBCs were used to examine the toxicity of these cationic antimicrobial polymers in solution. Toxicities were low, all polymers having HC50 values greater than 500 ppm. Hence, the more relevant HC20 values are presented in Table 17. As seen in Table 17, the cationic polymers prepared with MTC-PrBr (quaternized with TMA) show negligible hemolytic toxicity towards rat RBCs while the cationic polymers prepared with MTC-BnCl displayed greater hemolysis. In both series of polymers, an increase in hydrophobic monomer content gives rise to an increase in hemolysis generally. That is, the % hemolysis of Example 44>Example 45>Example 46 (not shown in the figures), and the % hemolysis of Example 49>Example 50>Example 51 (FIG. 4). This trend is also seen in the polymers prepared from MTC-PrBr and quaternized with imidazoles (Examples 47 and 48, not shown in the figures). Example 47 (quaternized with methyl imidazole) is less toxic in comparison to its ethyl analogue, Example 48 (not shown in figures). This observation is consistent with previous findings where increased toxicity is associated with higher proportion of hydrophobicity.

Figure 5:
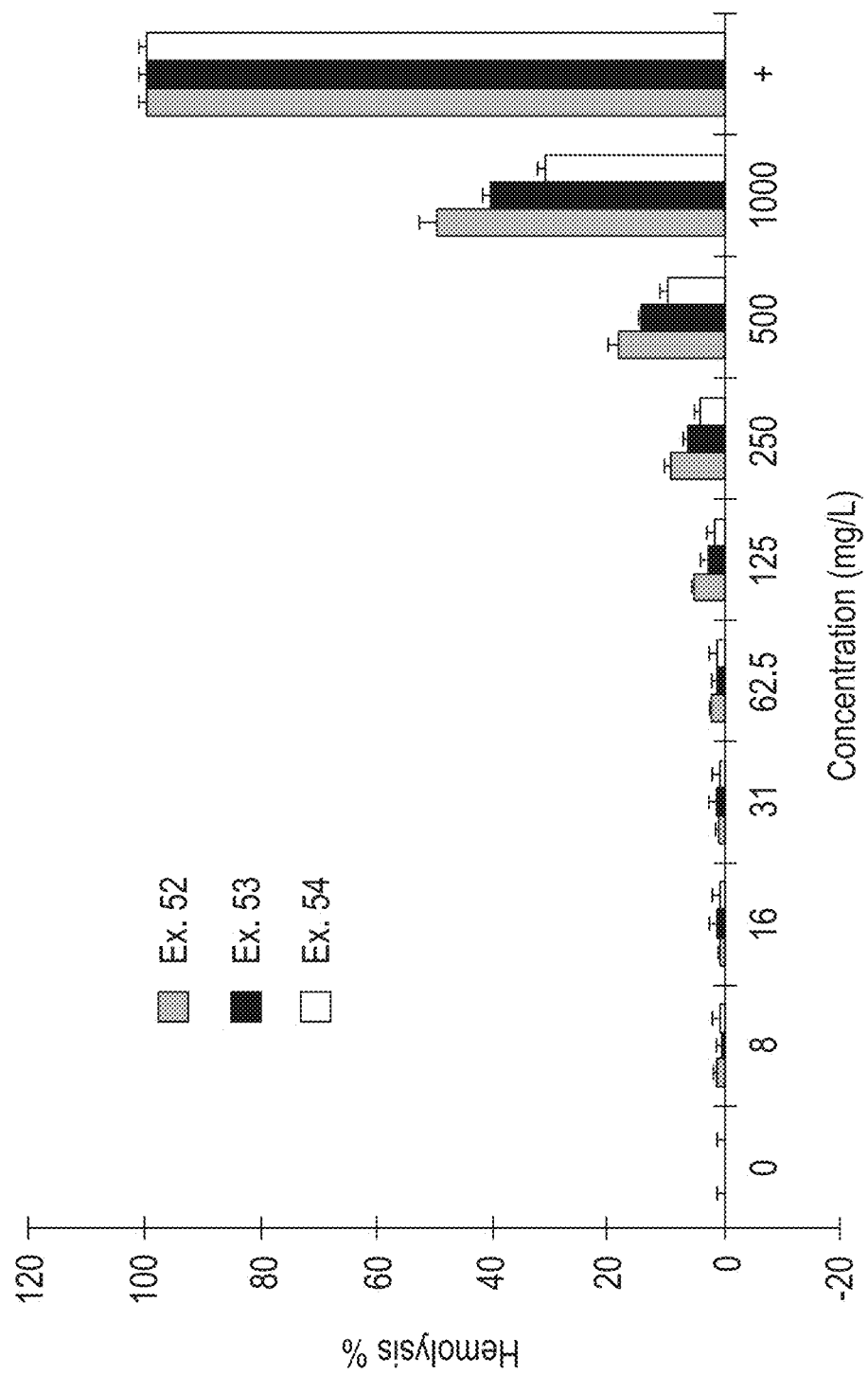
FIG. 5 is a graph showing the hemolysis activity against rat red blood cells of Examples 52 to 54 containing a pendant vitamin D2 moiety.

The hemolysis activity of Examples 52 to 54, which contain a pendant vitamin D2 moiety, is shown in FIG. 5 (bar chart). These polymers were also non-hemolytic (HC20 values were 1000 mg/L or more).

Time-Kill Studies of Vitamin E Functionalized Polymers

Figure 6A:
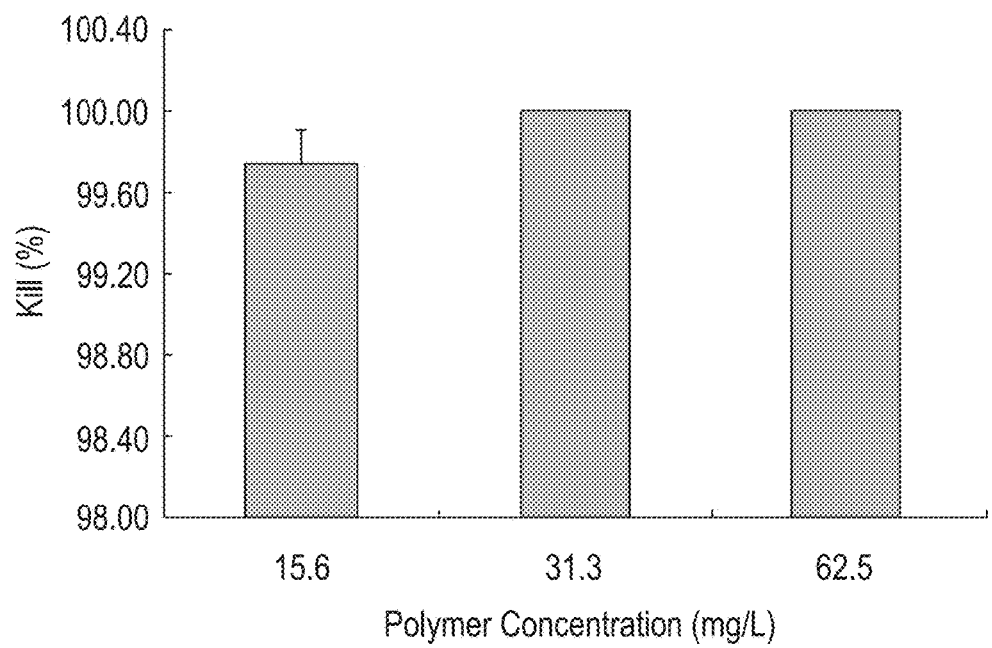
FIGS. 6A and 6B are bar charts showing viable bacterial colony-forming units (CFU) (as percent killed) after 18 hours incubation of bacteria *S. aureus* (FIG. 6A) and *Escherichia. coli* (*E. coli*) (FIG. 6B) treated with various concentrations (0, 0.5 MIC, MIC, 2 MIC) of cationic polymer Example 51.
Figure 6B:
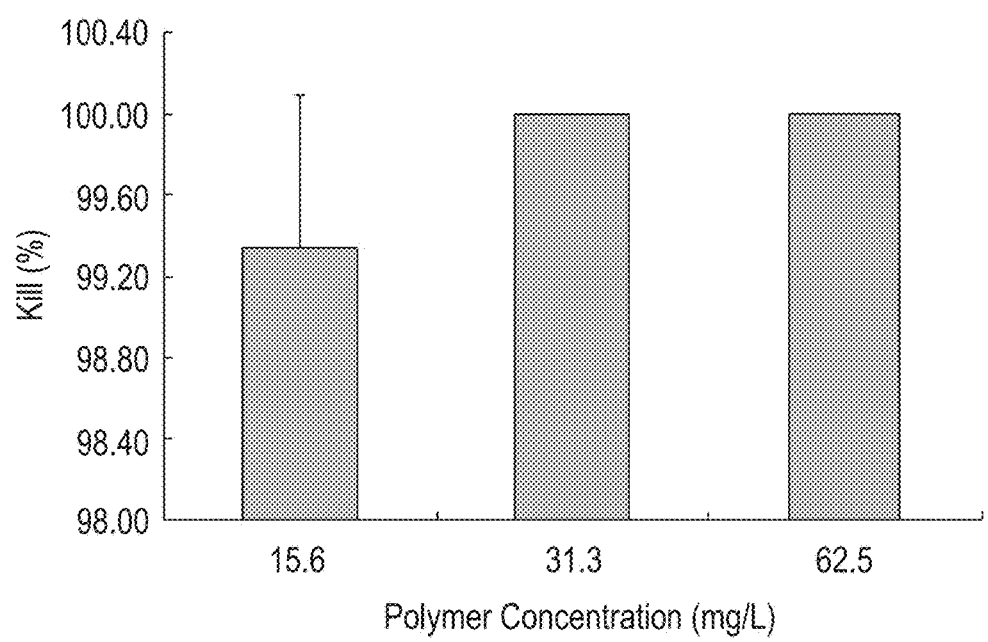

*S. aureus* and *E. coli* were treated with Example 51 (MTC-VitE/MTC-BnCl ratio of 1:30) in order to investigate the mechanism of antimicrobial properties. Colony counting assays were performed using *S. aureus* and *E. coli*. As can be seen in the bar charts of FIG. 6A and FIG. 6B, about 100% killing efficiency of each of the bacterial strains was achieved at MIC concentration after 18 hours treatment, which support the bactericidal mechanism.

Figure 7A:
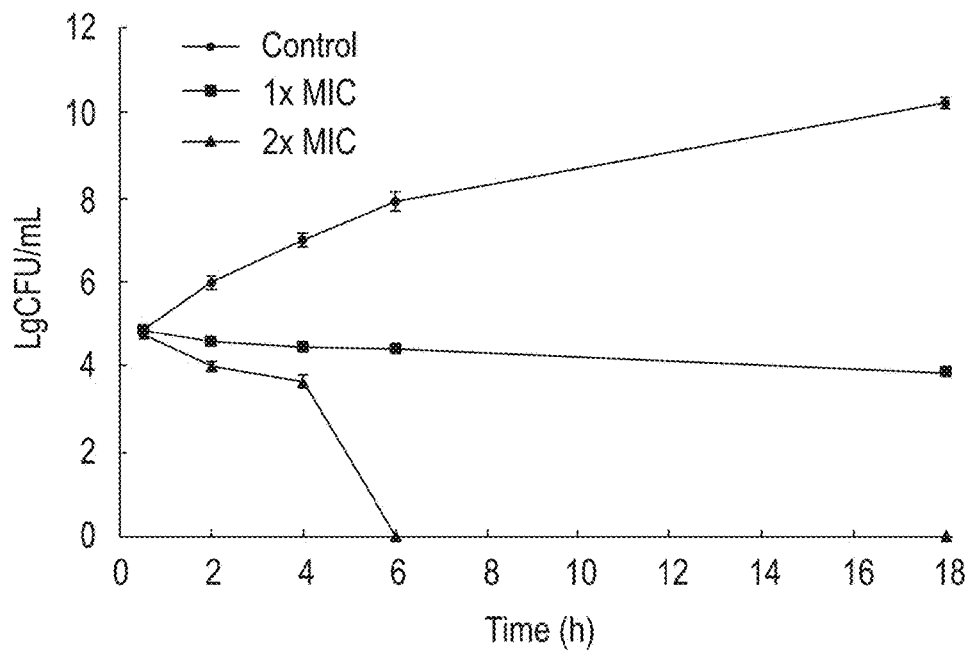
FIGS. 7A and 7B are graphs plotting viable bacterial colony-forming units (CFU) at different time points during an 18 hour incubation of bacteria *S. aureus* (FIG. 6A) and Escherichia. coli (E. coli) (FIG. 6B) treated with various concentrations (0, 0.5 MIC, MIC, 2 MIC) of cationic polymer Example 51.
Figure 7B:
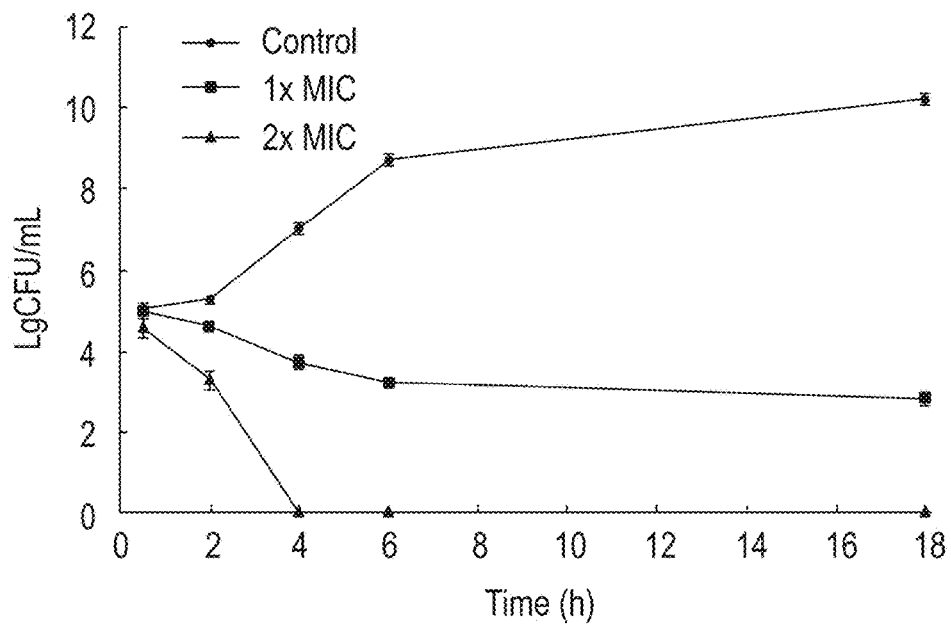

Time-kill kinetic experiments were performed also to confirm the mechanism. *S. aureus* and *E. coli* were treated with phosphate buffered saline (PBS) or Example 51 at MIC or 2.0MIC concentration. The viable colonies were counted at different time points during an 18 hour period. As shown in the graphs of FIG. 7A and FIG. 7B, after treatment with Example 51 at MIC concentration for 18 hours, the viable colonies of *S. aureus* and *E. coli* were few. At the lethal polymer concentration (2.0MIC), no viable colony was observed after 6 hours for *S. aureus* and after 4 hours for *E. coli*. These results indicate that the cationic polymers effectively kill bacteria instead of inhibiting their growth.

Figure 8:
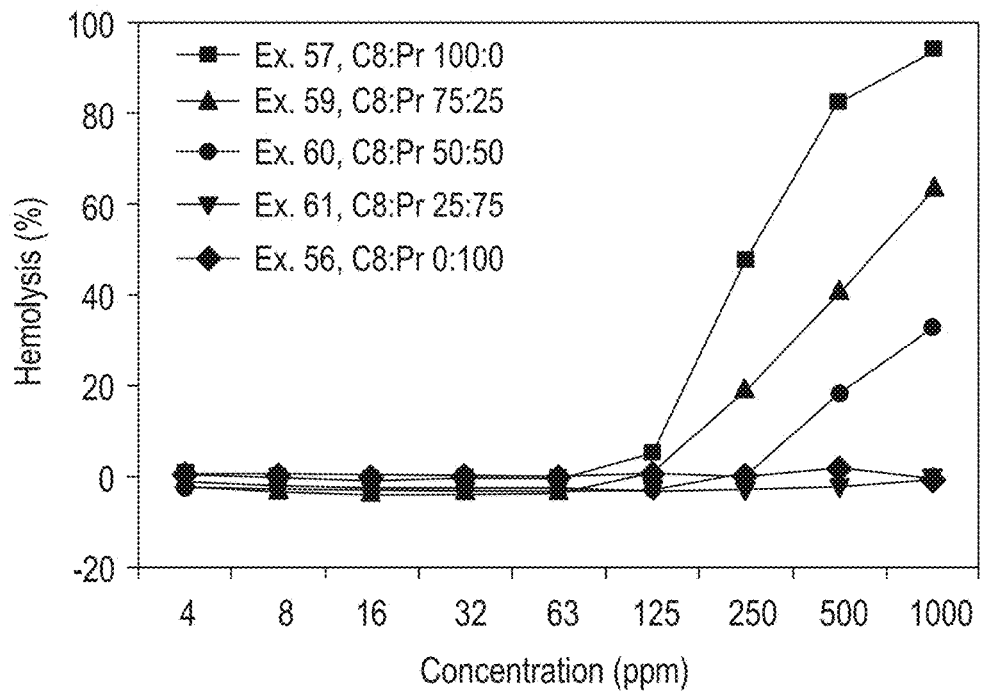
FIG. 8 is a graph showing the % hemolysis of rat blood cells as a function of concentration of Examples 58, 61, and 68-70.
Figure 9:
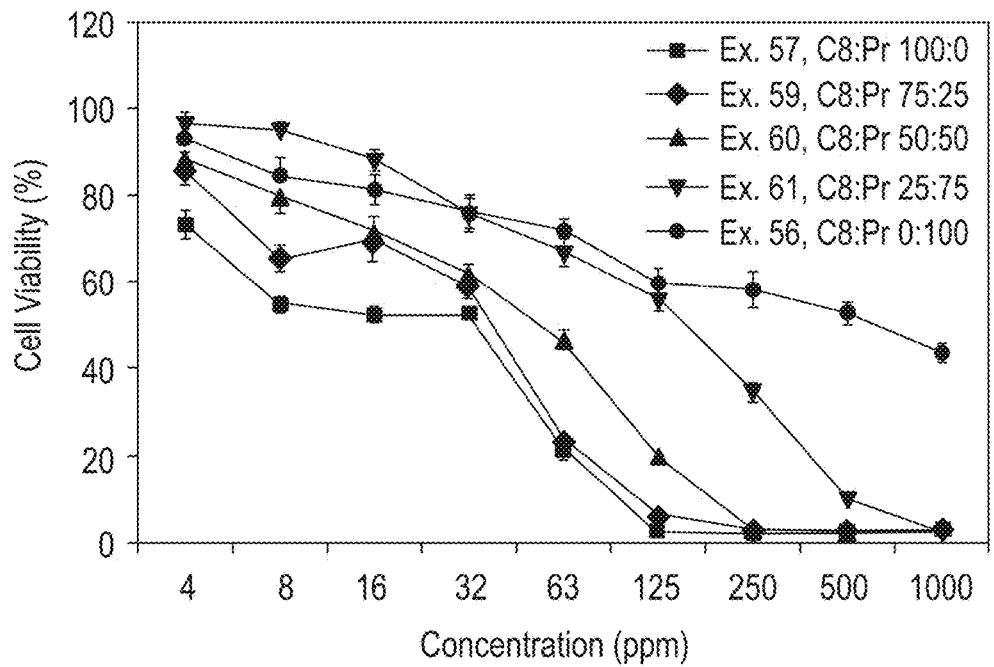
FIG. 9 is a graph showing human dermal fibroblast cell viability (%) as a function of concentration of cationic polymer Examples 58, 61, and 68-70.

Antimicrobial and Hemolytic Activity of Diol Initiated (BnMPA) Cationic Polymers With respect to the polymers formed using the di-nucleophilic initiator BnMPA (Table 18), the more hydrophobic MTC-C8Cl based cationic polymers (Examples 55, 57, and 58) in general exhibited more antimicrobial activity but greater red blood cell toxicity (lower HC50 values). The less hydrophobic MTC-PrCl based cationic polymer (Example 56) had lower antimicrobial activity and lower hemolytic activity (higher HC50 value). Diluting the cationic polymers prepared using a mixture of MTC-C8Cl with MTC-PrCl (Examples 59 to 61) resulted in comparable antimicrobial activity and higher HC50 values even up to 75 mol % MTC-PrCl compared to the MTC-C8Cl homopolymer (Example 57, Table 18). Examples 59 to 61 also exhibited lower hemolytic activity (FIG. 8, graph) and lower cytotoxicity (FIG. 9, graph) relative to the MTC-C8Cl homopolymer. Moreover, the MIC values of Examples 59 to 61 were lower than the CMC (Table 13) for S. *Epidermidis*, S. *Aureus*, and *E. Coli*. This observation indicates that a CMC is not necessary for antimicrobial activity. This method of balancing charge and hydrophobicity leads to cationic polymers having high antimicrobial activity and minimal mammalian cell cytotoxicity.

Mechanism of Antimicrobial Properties

Figure 10:
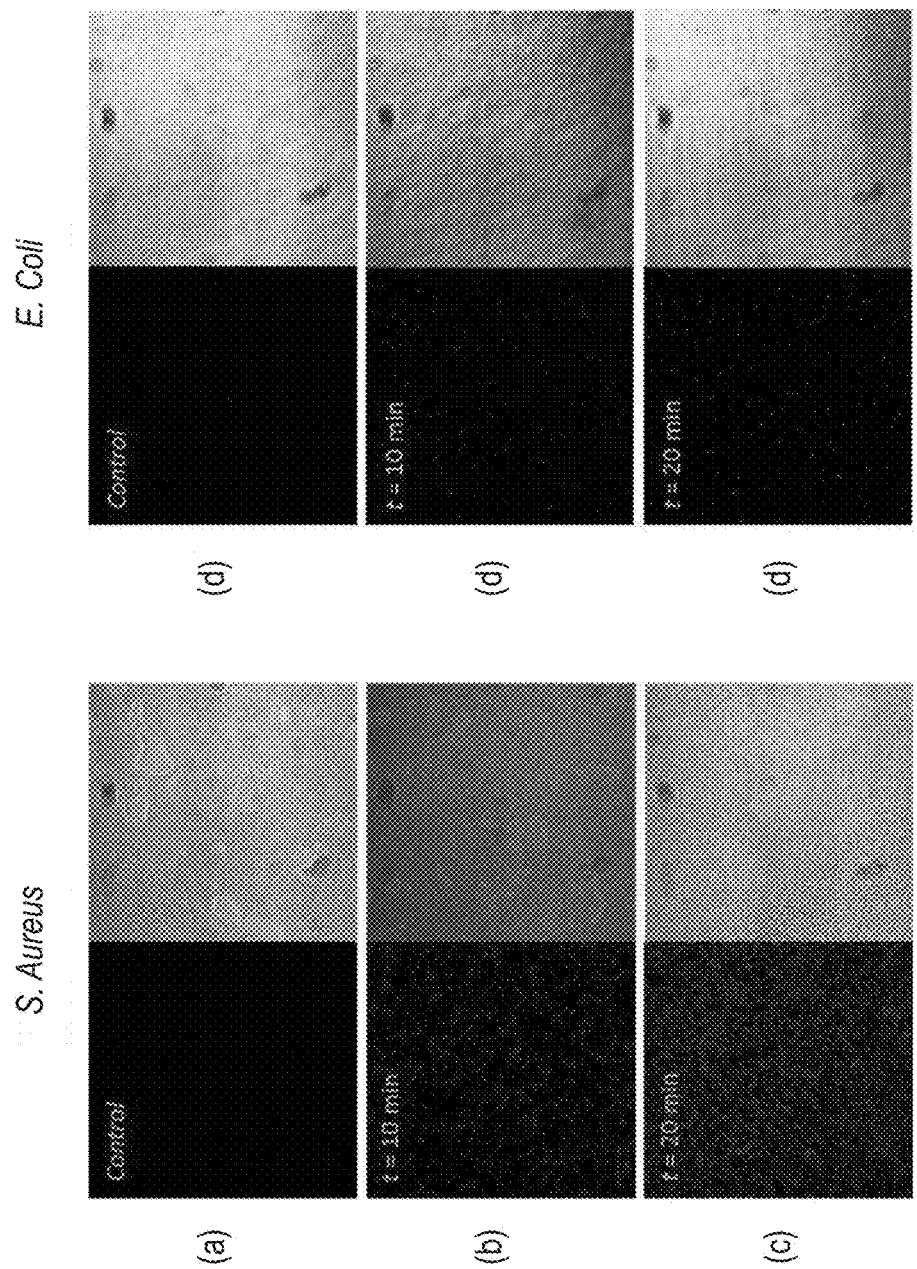
FIG. 10 is a confocal microscope image of S. aureus (left side) incubated with fluorescein isothiocyanate labeled (FITC-labeled) dextran in the absence (a) or presence of Example 51 for 10 min (b) and 20 min (c), and images of E. coli (right side) incubated with FITC-labeled dextran in the absence (d) or presence of Example 51 for 10 min (e) and 20 min (f). Scale bar: 10 micrometers.
Figure 11:
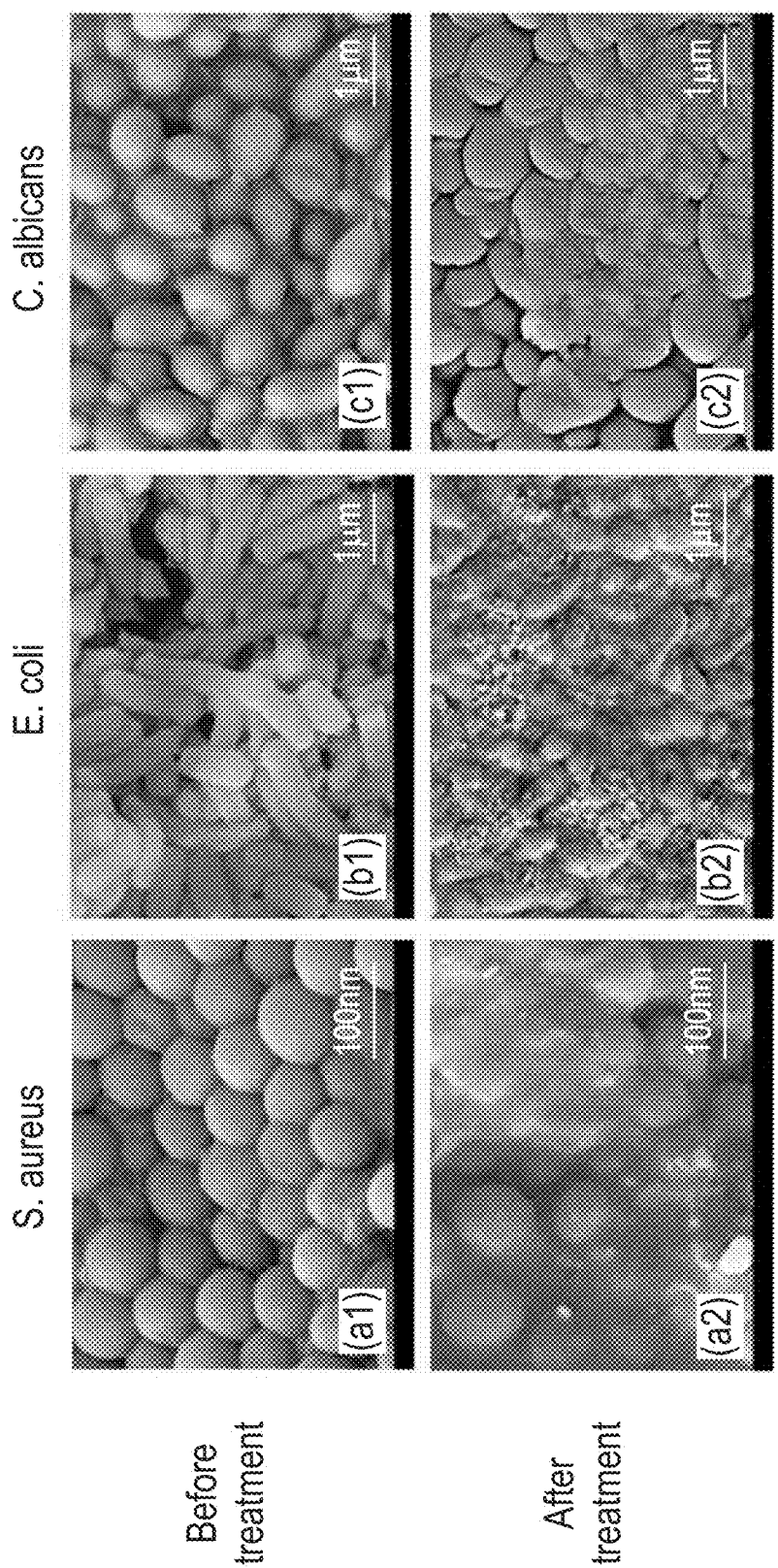
FIG. 11 is a series of scanning electron microscopic (SEM) images of S. aureus (a1, a2), E. coli (b1, b2), and before and after 2 hour incubation with cationic polymer Example 51, and Candida albicans (C. albicans) (c1, c2) before and after 2 hour incubation with cationic polymer Example 47. All experiments were carried out using a lethal dose (1.5×MIC) of the respective polymers.

The mechanism of cationic polymer microbial toxicity was further studied by using confocal microscopy and field emission scanning electron microscopy (FE-SEM). *S. aureus* and *E. coli* were treated with cationic polymer Example 51 (MTC-VitE/MTC-BnCl (1:30) quaternized with TMA) for a short-term (0 min, 10 min and 20 min) in the presence of FITC-labeled 100 K dextran, and then observed by using confocal microscopy after drying. As shown in the photograph of FIG. 10, in the absence of Example 51, no green fluorescence was observed in bacterial cells. However, after treating with the cationic polymer for 10 minutes, the uptake of fluorescein isothiocyanate labeled (FITC-labeled) dextran molecules in both the *S. aureus* and *E. coli* cells was seen clearly, suggesting pore formations in the bacterial membrane. The uptake of FITC-labeled dextran was much clearer in *S. aureus* and *E. coli* cells upon 20 min incubation, which suggests more severe membrane damage after prolonged membrane interactions with the cationic polymer. The morphological changes of the bacterial cells were observed by FE-SEM after treatment with the cationic polymer for a longer time scale (2 hours). As can be seen in the scanning electron microscope (SEM) images of FIG. 11, treatment with Example 51 at a lethal concentration (100 mg/L) for 2 hours results in significant membrane damage to *S. aureus* (FIG. 11 left side, a1 and a2) and *E. coli* (FIG. 11 middle, b1 and b2) when compared with the negative PBS control. And the similar phenomena was also observed with *C. albicans* (FIG. 11 right side, c1 and c2) after treatment with 500 mg/L Example 47 (MTC-VitE/MTC-PrBr (1:30), quaternized with methyl imidazole). These results indicated that the cationic polymer interacts with the membrane of bacterial and yeast cells by forming pores and eventually leads to disruption of the bacterial and yeast membranes.

Comparison of Diol Initiated Cationic Polymers (Bn-MPA) to Monol Initiated Cationic Polymers (BnOH and 4-MeBnOH)

The effect of diol initiator versus monol initiator, and endcapping, on cationic polymers prepared with MTC-BnCl can be seen by comparing the properties of Examples 43 (monol initiator BnOH, Table 17) and Examples 62 and 63 (diol initiator Bn-MPA, Table 18), reproduced below in Table 19. Examples 42 and 56, prepared from MTC-PrBr and MTC-PrCl, respectively, are also reproduced in Table 19.

TABLE 19

| Ex. | Initiator | Endcap | Cyclic Monomer | DP[b] (n') | Quaternizing agent | Total cationic side chain carbons | MIC (mg/L), TSB[a] | | | | HC$_{50}$ (mg/L) |
| | | | | | | | S. epidermidis | S. aureus | E. coli | P. aeruginosa | C. albicans | |
|---|---|---|---|---|---|---|---|---|---|---|---|---|
| 42 | BnOH | None | MTC-PrBr | 30 | TMA | 7 | | 500 | 1000 | >1000 | 500 | >1000 |
| 56 | Bn-MPA | Acetyl | MTC-PrCl | 30 | TMA | 7 | 16 | 500 | 1000 | >1000 | 500 | >1000 |
| 43 | BnOH | None | MTC-BnCl | 30 | TMA | 12 | | 125 | 125 | >1000 | 125 | >1000 |
| 62 | Bn-MPA | None | MTC-BnCl | 30 | TMA | 12 | | 31.3 | 62.5 | >1000 | 125 | >1000 |
| 63 | Bn-MPA | Acetyl | MTC-BnCl | 30 | TMA | 12 | 4 | 125 | 125 | >1000 | 125 | >1000 |

[a] tryptic soy broth.
[b] DP is based on feed.

Comparing Examples 43 and 62, diol (Bn-MPA) initiated cationic polymer 62 was more active against *S. aureus* and *E. coli* compared to monol (BnOH) initiated cationic polymer Example 43, other features of the polymers being the same. Neither polymer was effective against *P. aeruginosa*. The two polymers were equally effective against *C. albicans*. Each polymer was non-toxic to red blood cells.

Comparing cationic polymers differing only in endcap groups (Examples 62 and 63), the endcapped polymer Example 63 was less active than the non-endcapped polymer Example 62 against *S. aureus* and *E. coli*. Neither polymer was effective against *P. aeruginosa*. Both polymers were equally effective against *C. albicans*. Each polymer was non-toxic to red blood cells.

Each of the cationic polymers prepared using MTC-PrCl/Br (Examples 42 and 56) were weakly active or inactive against *S. aureus, E. coli, P. aeruginosa*, and *C. albicans* (MIC 500 mg/L or more for each microbe) and each cationic polymer was non-toxic to red blood cells (HC>1000 mg/L).

Another difference was observed between the monol and diol initiated cationic polymers with respect to RBC toxicity dependence on the degree of polymerization (DP). The diol initiated cationic polymers prepared using MTC-C8Cl exhibited increasing HC50 values (decreasing RBC toxicity) with decreasing DP. This can be seen by comparing Example 55 (HC50 250-500, DP 15), Example 57 (HC50 250, DP 30), and Example 58 (HC50 125-250, DP 60) of Table 18. The antimicrobial activity of these diol initiated polymers did not appear to be sensitive to DP. By comparison, the monol-initiated cationic polymers generally exhibited increasing HC50 values (lower RBC toxicity) with increasing DP from 5 to 30. This can be seen by comparing Examples 10, 12, 14, and 16 of Table 14, and Examples 20, 22, 24, and 26 of Table 14. These results indicate that the position and type of initiator fragment has an influence on the antimicrobial and/or selectivity properties of the cationic polymer, allowing potentially for monol-initiated and diol-initiated cationic polymers sharing the same number and type of cationic carbonate repeat units to have usefully distinct and beneficial antimicrobial properties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

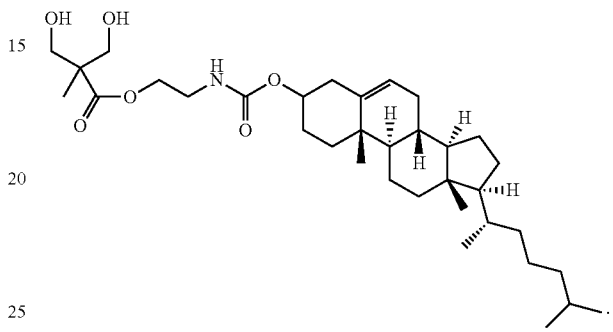

What is claimed is:
1. An antimicrobial cationic polymer of formula (12):

$$Z^c-P^b-C'-P^b-Z^c \qquad (12),$$

wherein
C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur,
each $Z^c$ is an independent monovalent end group selected from the group consisting of hydrogen and $C_1$-$C_{15}$ moieties,
each polymer chain $P^b$ consists essentially of cationic carbonate repeat units, wherein i) the cationic polymer comprises a total of 5 to about 45 cationic carbonate repeat units, ii) each of the cationic carbonate repeat units comprises a) a backbone portion of the polymer chain comprising an aliphatic carbonate group, and b) a cationic side chain linked to the backbone portion, and iii) the cationic side chain comprises a positive-charged heteroatom Q' of a quaternary ammonium group and/or quaternary phosphonium group,
about 25% to 100% of all the cationic carbonate repeat units of the cationic polymer, designated first cationic carbonate repeat units, have a structure selected from the group consisting of

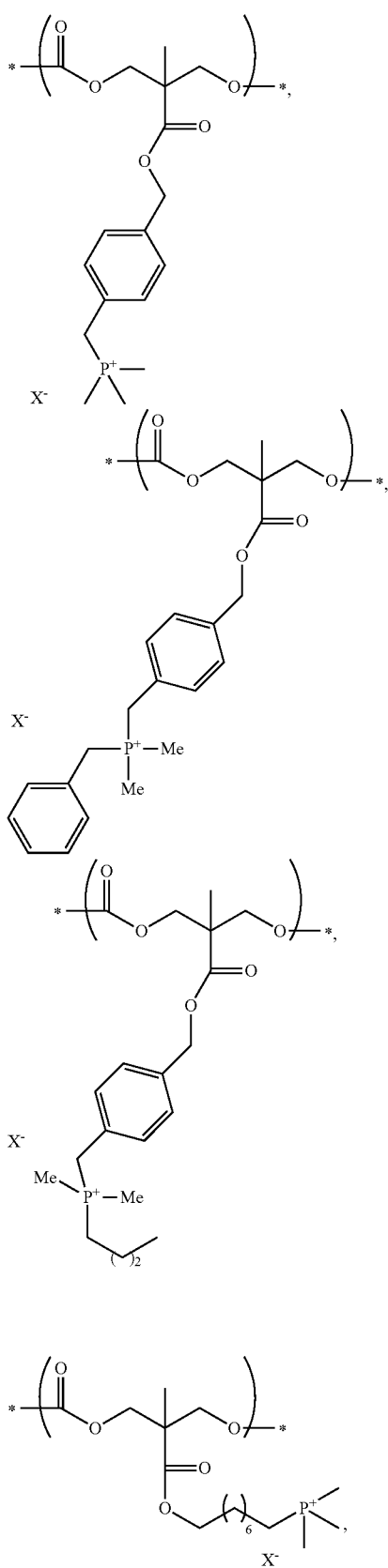

and combinations thereof, wherein X⁻ is a negative-charged ion, and

0% to about 75% of the cationic carbonate repeat units of the cationic polymer, designated second cationic carbonate repeat units, have a cationic side chain comprising 6 to 9 carbons.

2. The cationic polymer of claim 1, wherein the second cationic carbonate repeat units have a cationic side chain comprising 6 to 12 carbons.

3. The cationic polymer of claim 1, wherein the first cationic repeat units have the structure

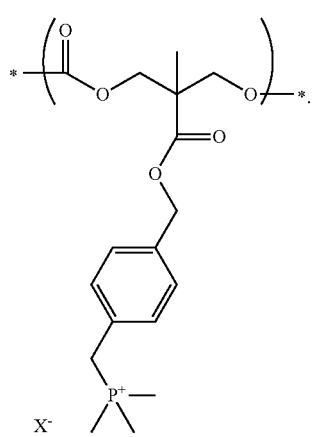

4. The cationic polymer of claim 1, wherein the first cationic repeat units have the structure

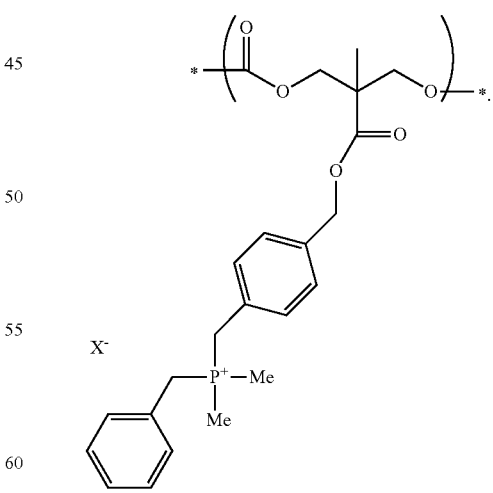

5. The cationic polymer of claim 1, wherein the first cationic carbonate repeat units have the structure

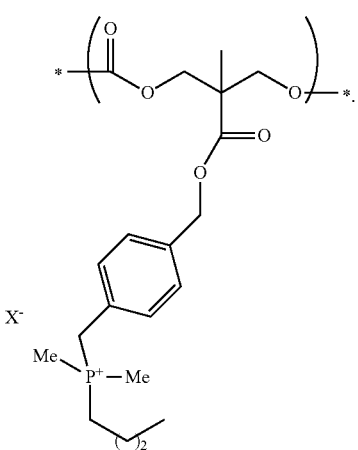

6. The cationic polymer of claim 1, wherein the first cationic repeat units have the structure

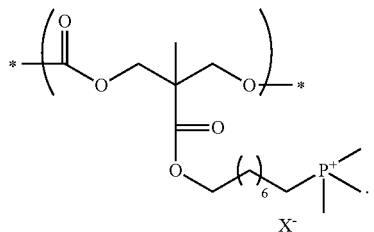

7. The cationic polymer of claim 1, wherein the cationic polymer is effective in killing a microbe selected from the group consisting of *Staphylococcus epidermidis* (*S. epidermidis*), *Staphylococcus aureus* (*S. aureus*), *Escherichia coli* (*E. coli*), *Pseudomonas aeruginosa* (*P. aeruginosa*), *Candida albicans* (*C. albicans*), Methicillin-resistant *Staphylococcus aureus* (MRSA), Vancomycin-resistant *Enterococcus* (VRE), *Acinetobacter baumannii* (*A. baumannii*), *Cryptococcus neoformans* (*C. neoformans*), *Klebsiella pneumoniae* (*K. pneumoniae*), and combinations thereof.

8. An antimicrobial cationic polymer of formula (14):

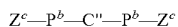 (14), wherein
- C" is a divalent linking group joining polymer chains $P^b$, wherein C" comprises i) a first heteroatom linked to a first polymer chain $P^b$, wherein the first heteroatom is selected from the group consisting of nitrogen, oxygen, and sulfur, ii) a second heteroatom linked to a second polymer chain $P^b$, wherein the second heteroatom is selected from the group consisting of nitrogen, oxygen, and sulfur, and iii) a covalently bound form of a compound selected from the group consisting of steroids, non-steroid hormones, vitamins, and drugs,
- each $Z^c$ is an independent monovalent end group selected from the group consisting of hydrogen and $C_1$-$C_{15}$ moieties,
- each polymer chain $P^b$ consists essentially of cationic carbonate repeat units, wherein i) the cationic polymer comprises a total of 5 to about 45 cationic carbonate repeat units, ii) each of the cationic carbonate repeat units comprises a) a backbone portion of the polymer chain comprising an aliphatic carbonate group, and b) a $C_6$-$C_{25}$ cationic side chain linked to the backbone portion, and iii) the cationic side chain comprises a positive-charged heteroatom Q' of a quaternary ammonium group and/or quaternary phosphonium group, about 25% to 100% of the cationic carbonate repeat units of the cationic polymer, designated first cationic carbonate repeat units, have a structure selected from the group consisting of

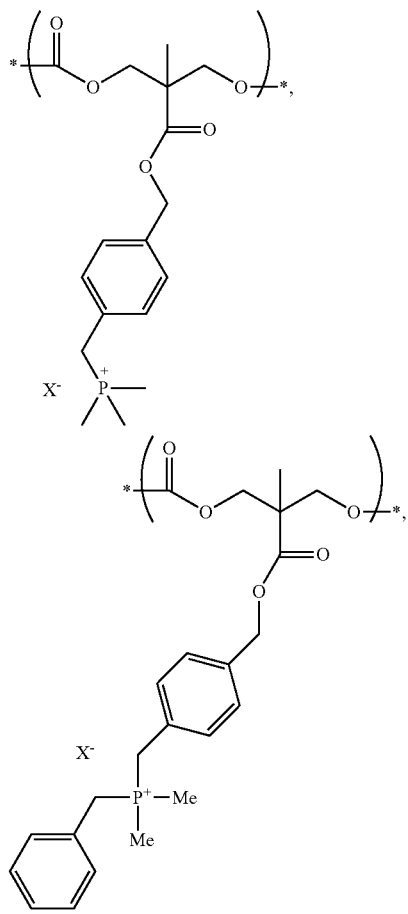

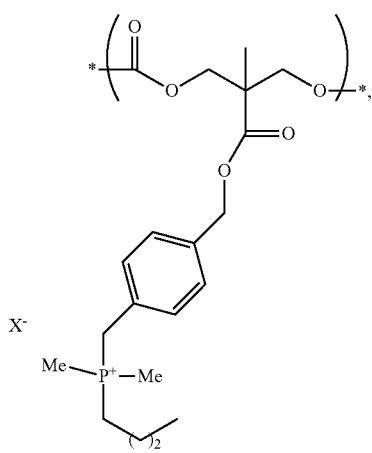

103

-continued

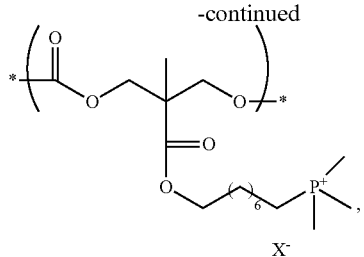

and combinations thereof, wherein X⁻ is a negative-charged ion, and

0% to about 75% of the cationic carbonate repeat units of the cationic polymer, designated second cationic carbonate repeat units, have a cationic side chain group comprising 6 to 9 carbons.

9. The cationic polymer of claim 8, wherein C" comprises a cholesteryl group.

10. The cationic polymer of claim 8, wherein C" comprises a covalently bound form of vitamin.

11. The cationic polymer of claim 8, wherein the vitamin is selected from the group consisting of vitamin E compounds, vitamin D compounds, and combinations thereof.

12. An antimicrobial cationic random copolymer of formula (16):

$$Z^c—P^c—C'—P^c—Z^c \quad (16),$$

wherein

C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, each $Z^c$ is an independent monovalent end group selected from the group consisting of hydrogen and $C_1$-$C_{15}$ moieties, each $P^c$ is a polymer chain consisting essentially of I) about 85 mol % to 99.9 mol % of cationic carbonate repeat units, and II) 0.1 mol % to about 15 mol % of a carbonate repeat unit comprising a covalently bound form of a steroid and/or a vitamin compound, designated H', wherein i) the cationic polymer has a total number of repeat units of about 5 to about 45, ii) each of the cationic carbonate repeat units comprises a) a polymer backbone portion comprising an aliphatic carbonate group, and b) a $C_6$-$C_{25}$ cationic side chain portion linked to the polymer backbone portion, and iii) each cationic side chain portion comprises a positive-charged heteroatom Q' of a quaternary ammonium group and/or quaternary phosphonium group, about 25% to 100% of the cationic carbonate repeat units of the cationic polymer, designated first cationic carbonate repeat units, have a structure selected from the group consisting of

104

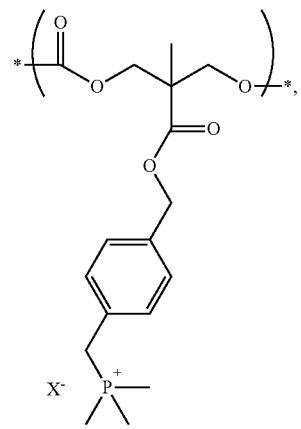

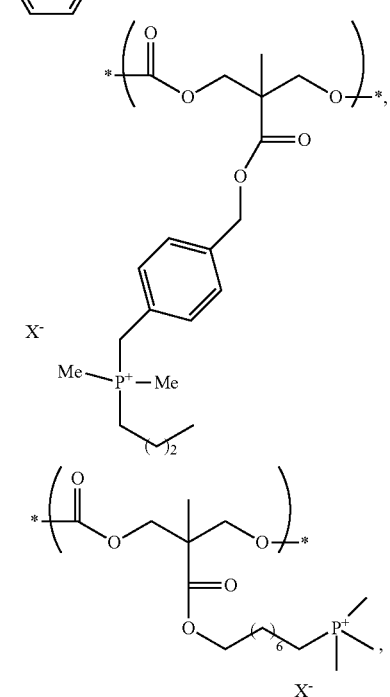

and combinations thereof, wherein X⁻ is a negative-charged ion, and

0% to about 75% of the cationic carbonate repeat units of the cationic polymer, designated second cationic carbonate repeat units, have a cationic side chain group comprising 6 to 9 carbons.

13. The random copolymer of claim 12, wherein H' is a covalently bound form of alpha-tocopherol.

14. The random copolymer of claim 12, wherein H' is a covalently bound form of ergocalciferol.

15. An antimicrobial cationic polymer has a structure in accordance with formula (18):

wherein

C' is a $C_2$-$C_{15}$ divalent linking group joining polymer chains $P^b$, wherein C' comprises i) a first heteroatom linked to a first polymer chain $P^b$, wherein the first heteroatom is selected from the group consisting of nitrogen, oxygen, and sulfur, and ii) a second heteroatom linked to a second polymer chain $P^b$, wherein the second heteroatom is selected from the group consisting of nitrogen, oxygen, and sulfur, $Y^c$ is an independent monovalent first end group selected from the group consisting of hydrogen, groups comprising a covalently bound form of a steroid, and groups comprising a covalently bound form of a vitamin, $Y^d$ is an independent monovalent second end group selected from the group consisting of hydrogen, groups comprising a covalently bound form of a steroid, and groups comprising a covalently bound form of a vitamin, each polymer chain $P^b$ consists essentially of cationic carbonate repeat units, wherein i) the cationic polymer comprises a total of 5 to about 45 cationic carbonate repeat units, ii) each of the cationic carbonate repeat units comprises a) a backbone portion of the polymer chain comprising an aliphatic carbonate group, and b) a cationic side chain linked to the backbone portion, and iii) the cationic side chain comprises a positive-charged heteroatom Q' of a quaternary ammonium group and/or quaternary phosphonium group, about 25% to 100% of all the cationic carbonate repeat units of the cationic polymer, designated first cationic carbonate repeat units, have a structure selected from the group consisting of

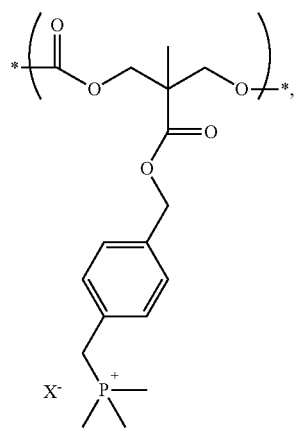

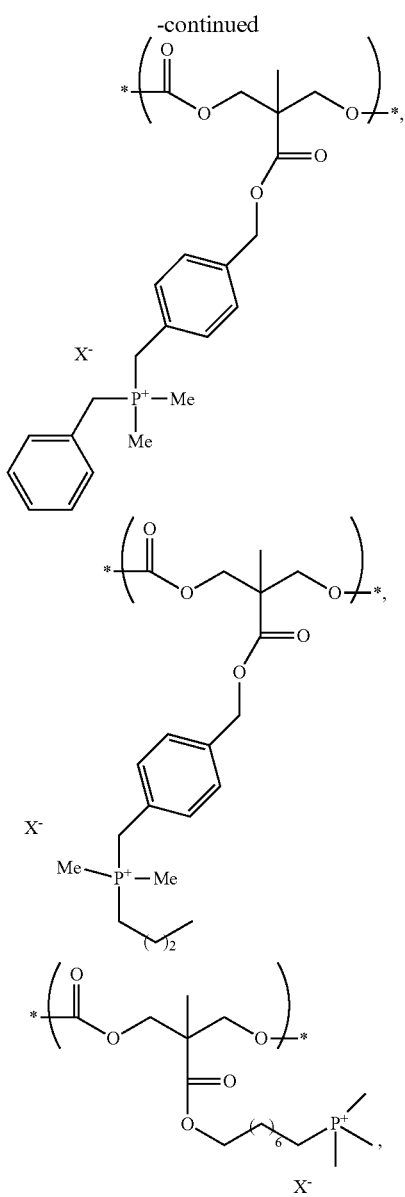

and combinations thereof, wherein $X^-$ is a negative-charged ion, and

0% to about 75% of the cationic carbonate repeat units of the cationic polymer, designated second cationic carbonate repeat units, have a cationic side chain comprising 6 to 9 carbons.

16. An aqueous composition for killing a microbe, the composition comprising the cationic polymer of claim 1.

17. The composition of claim 16, wherein the composition can be administered by injection.

18. The composition of claim 16, wherein the cationic polymer has a critical micelle concentration, and the concentration of the cationic polymer is below the critical micelle concentration of the cationic polymer.

19. A method of killing a microbe, comprising contacting the microbe with the cationic polymer of claim 1.

20. A method of forming the cationic polymer of claim 8, comprising, forming a polycarbonate by an organocatalyzed ring opening polymerization (ROP) of a cyclic carbonate monomer, wherein the ROP is initiated by a di-nucleophilic compound selected from the group consisting of steroids, vitamins, compounds comprising a covalently bound form of the foregoing steroids and vitamins, and combinations thereof;

optionally endcapping the polycarbonate; and treating the polycarbonate with a quaternizing agent, thereby forming the cationic polymer, wherein the cyclic carbonate monomer has a structure selected from the group consisting of

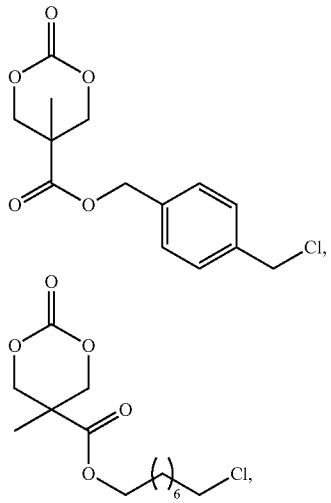

and combinations thereof.

21. The method of claim 20, wherein the quaternizing agent is a tertiary amine selected from the group consisting of N-butylimidazole, trimethylamine, dimethylbenzylamine, dimethylbutylamine, and combinations thereof.

22. The method of claim 20, wherein the quaternizing agent is dimethylbenzylamine.

23. The method of claim 20, wherein the initiator is Chol-MPA: